(12) United States Patent
Polyakov et al.

(10) Patent No.: US 11,173,193 B2
(45) Date of Patent: Nov. 16, 2021

(54) IMMUNOBIOLOGICAL PRODUCTS

(71) Applicants: Igor Polyakov, Ulm (DE); Liudmila Ivanova, Ulm (DE)

(72) Inventors: Igor Polyakov, Ulm (DE); Liudmila Ivanova, Ulm (DE)

( * ) Notice: Subject to any disclaimer, the term of this patent is extended or adjusted under 35 U.S.C. 154(b) by 325 days.

(21) Appl. No.: 16/085,033

(22) PCT Filed: Mar. 15, 2017

(86) PCT No.: PCT/EP2017/056146
§ 371 (c)(1),
(2) Date: Sep. 14, 2018

(87) PCT Pub. No.: WO2017/158040
PCT Pub. Date: Sep. 21, 2017

(65) Prior Publication Data
US 2019/0125846 A1 May 2, 2019

(30) Foreign Application Priority Data
Mar. 15, 2016 (EP) .................................... 16160534

(51) Int. Cl.
*A61K 31/722* (2006.01)
*A61K 39/00* (2006.01)
*A61K 39/04* (2006.01)
*C08B 37/08* (2006.01)

(52) U.S. Cl.
CPC ........ *A61K 39/0002* (2013.01); *A61K 31/722* (2013.01); *C08B 37/003* (2013.01)

(58) Field of Classification Search
CPC .. A61K 31/722; A61K 39/00; A61K 39/0002; C08B 37/003
USPC .................................................. 536/20, 124
See application file for complete search history.

(56) References Cited

FOREIGN PATENT DOCUMENTS

| CN | 102727887 A | 10/2012 |
|---|---|---|
| WO | WO 1997/007232 A1 | 2/1997 |
| WO | WO 1998/015284 A2 | 4/1998 |
| WO | WO 2013/033400 A2 | 3/2013 |
| WO | WO 2017/158040 | 9/2017 |

OTHER PUBLICATIONS

Shamov et al. (Journal of Colloid and Interface Science, 249:316-321, 2002).*
International Search Report and Written Report for PCT/EP2017/056146 dated May 10, 2017.
Lee, Kuen Yong, Wan Shik Ha, and Won Ho Park. "Blood compatibility and biodegradability of partially N-acylated chitosan derivatives." *Biomaterials* 16.16 (1995): 1211-1216.
Seferian. Peter G., and Mitzi L. Martinez. "Immune stimulating activity of two new chitosan containing adjuvant formulations." *Vaccine* 19.6 (2000): 661-668.
Wang, Huadong, et al. "An adjuvanted inactivated murine cytomegalovirus (MCMV) vaccine induces potent and long-term protective immunity against a lethal challenge with virulent MCMV." *BMC Infectious Diseases* 14.1 (2014): 195.

* cited by examiner

*Primary Examiner* — Rodney P Swartz
(74) *Attorney, Agent, or Firm* — Parker Highlander PLLC

(57) ABSTRACT

The invention relates to a method comprising the step of incubating chitosan in an aqueous solution of an organic carboxylic acid or a salt thereof, a modified chitosan obtainable by the method of the present invention, a hydro colloid, a compound of formula [X]n, a composition comprising the modified chitosan, the hydro colloid or compound according to the present invention, the modified chitosan, the hydro colloid, the compound or composition according to the present invention for use in human and/or veterinary medicine and the modified chitosan, the hydro colloid, the compound or composition according to the present invention for use in a method of treating and/or preventing mastitis, preferably latent mastitis and/or acute mastitis, endometritis, preferably chronic, acute and/or purulent-catarrhal endometritis, hoof- and claw diseases, lameness, lesions in the interdigital space, digital dermatitis, interdigital dermatitis, interdigital phlegmon, trichophytosis, microsporosis, mycosis of skin, allergies, as well as diseases complicated by allergies, in particular allergic obstructive pulmonary disease, allergic skin diseases, allergic ear erythema, allergic rhinitis, allergic conjunctivitis, acute allergic contact dermatitis, chronic allergic contact eczema or atopic eczema, obstructive pulmonary disease, in particular chronic obstructive pulmonary disease, skin diseases, in particular dermatitis, ear erythema, rhinitis, conjunctivitis, dermatophytosis or warts, in particular Common warts, in a subject and for modulating the immune response in a subject and/or for enhancing reproduction efficiency, preferably reproduction efficiency in animal breeding.

20 Claims, 4 Drawing Sheets

Days of clinical observation

Day of clinical observations

Day of clinical observations

IMMUNOBIOLOGICAL PRODUCTS

Figure 1:
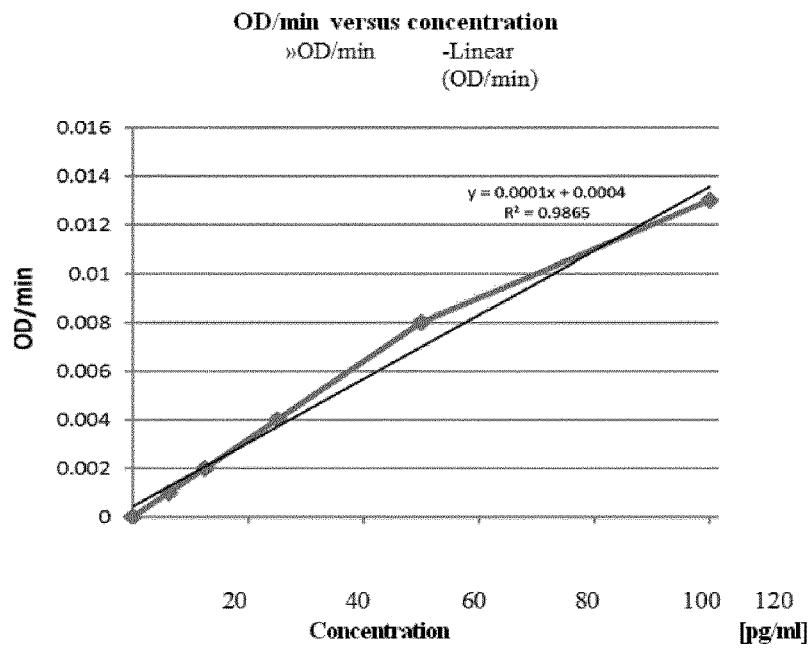

This application is a national phase application under 35 U.S.C. § 371 of International Application No. PCT/EP2017/056146, filed Mar. 15, 2017, which claims priority to European Patent Application No. 16160534.0, filed Mar. 15, 2016. The entire text of each of the above referenced disclosures is specifically incorporated herein by reference.

The invention relates to a method comprising the step of incubating chitosan in an aqueous solution of an organic carboxylic acid or a salt thereof, a modified chitosan obtainable by the method of the present invention, a hydro colloid, a compound of formula [X]n, a composition comprising the modified chitosan, the hydro colloid or compound according to the present invention, the modified chitosan, the hydro colloid, the compound or composition according to the present invention for use in human and/or veterinary medicine and the modified chitosan, the hydro colloid, the compound or composition according to the present invention for use in a method of treating and/or preventing mastitis, preferably latent mastitis and/or acute mastitis, endometritis, preferably chronic, acute and/or purulent-catarrhal endometritis, hoof- and claw diseases, lameness, lesions in the interdigital space, digital dermatitis, interdigital dermatitis, interdigital phlegmon, trichophytosis, microsporosis, mycosis of skin, allergies, as well as diseases complicated by allergies, in particular allergic obstructive pulmonary disease, allergic skin diseases, allergic ear erythema, allergic rhinitis, allergic conjunctivitis, acute allergic contact dermatitis, chronic allergic contact eczema or atopic eczema, obstructive pulmonary disease, in particular chronic obstructive pulmonary disease, skin diseases, in particular dermatitis, ear erythema, rhinitis, conjunctivitis, dermatophytosis or warts, in particular Common warts, in a subject and for modulating the immune response in a subject and/or for enhancing reproduction efficiency, preferably reproduction efficiency in animal breeding.

Mastitis of cattle is distributed worldwide and causes extensive economic damage in agriculture. The damage caused by mastitis is caused in particular by a reduced milk yield and reduced milk quality. Mastitis causes hypogalactia and agalactia in animals. The loss of parts of secretory epithelial cells results in regeneration of connective tissue and to atrophy of the affected part of the udder.

Endometritis is the inflammation of a mucous membrane of the uterus, which is followed by a more or less significant change of the endometria and an increased activity of the healthy or regenerated uterine glands. The uteritis is most frequently followed by reproduction of polymorphic microflora. Chronic endometritis is a very widespread gynecological disease: it is registered at 12-40% of infertile cows.

About 15-25% of cows suffer from clinically apparent and hidden mastitis and in particular cattle with a very high milk production are most exposed to this illness. Milk failure of convalescent cows makes up to 20% of the general milk yield on a farm. The existing control methods and treatments of mastitis inevitably lead to high losses of animals and milk. Postpartum diseases of cows comprising endometritis as the most common disease bring about huge economic damages. There are various reasons for endometritis. The treatment by veterinary physicians is time and cost consuming.

The most common form of mastitis is the hidden (subclinical) mastitis. The hidden mastitis of cows is followed by a softly proceeding inflammatory process with only few or no clinical signs of mastitis. Treatment of animals with this form of mastitis is complicated. This form is very common on large dairy units and is usually only diagnosed during monthly performed examinations for the hidden form of mastitis of the milking herd. About 15% of the lactating cows are affected by the latent mastitis during machine milking. The reasons of the hidden mastitis developing are manifold. The hidden mastitis mostly appears due to non-compliance with veterinary health regulations by operators of machine milking, due to the wrong start and non-compliance with a course of the mastitis animal treatment. At the same time chronic endometritis is a very common gynecological disease: it is registered at 12-40% of infertile cows.

An objective indicator for a healthy cow udder is the quantity of the contained somatic cells in the milk. Somatic cells in cow milk are presented by leukocytes and epithelium of mammary glands. Epithelial cells are dominated in the milk secretion from a healthy cow. The epithelial cells are formed in udder tissues during the process of natural aging and regeneration of tissues. During mastitis the migration of leukocytes increases in the inflammation area that finally leads to an acute increase of somatic cells in the milk. 1 ml milk from clinically healthy cows contains 200-250 thousand somatic cells. During mastitis their quantity increases up to 900 thousand and more.

The milk from cows affected with the hidden form of mastitis has hypoacidity since there is comprises an increased content of chlorides, albumin and globulins. The quantity of cell elements increases several times, especially the quantity of leukocytes. At the same time the content of solids (casein, lactose, calcium and phosphorus) is reduced. When milk from cows affected with the hidden form of mastitis is combined with milk of healthy cows the overall quality of the milk is reduced. It cannot be used for cheese preparation and sour milk products and has an extreme adverse effect on human health.

Currently, antibiotics, sulfanilamide preparations or mixtures thereof are used for treating the various forms of mastitis and endometritis. Also extracts of plants comprising essential oils with antimicrobic effect are used. In recent years enzyme preparations and immunobiological products comprising probiotics and interferon were used.

There are a lot of methods and agents for treating mastitis with clinical signs, but treatment of the hidden forms of mastitis is complicated and the distribution of this form of mastitis is much higher than other forms. There are known methods of treating subclinical mastitis by physical therapy (applications of ozokerite, paraffin, warming bandages, compresses, warming by lamps solux, infrared radiation on an udder) and also the use of laser devices of various modifications are applied. The course of treatment consists of 3-4 sessions, wherein only one session is performed per day. The efficiency of these methods is between 60-85%, but they are very time and cost consuming. Known is also a method of intramuscular administration of antibiotics: A dose of 8-10 ml of Tilozin 200 once a day over three days, a dose of 0.5 ml/10 kg body weight of Bilozin 200 twice a day (milk can't be used for food purposes during 7 days), a subcutaneous dose of 1 ml/50 kg body weight of Efikur during 2-3 days. When using antibiotics there is a need to check preliminary the activators from the affected quarter of an udder on sensitivity to antibiotics. Moreover, milk and products of slaughter from the treated animals can't be used within several days or week. Known is also a method of an intramammary application of the preparation Mastiyet-forte in a plastic syringe which contains oxytetracycline, Neomycin, bacitracin and Prednisolone. The preparation is very effective but milk and products of slaughter from the treated animals can't be used within several days. Known is also a way of treating subclinical mastitis by a procaine blockade of an udder according to D. D. Logvinov. Injections of 0.5% solution of procaine are carried out every 48 hours. Using this method recovery lasts 3-5 days. Disadvantages of this method are that it is labor intensive and that it bears the risk of microbial contamination by injection. Also known is a way of treating sick cows by using 1% solution of collargol and preparations comprising silver. Preparations are injected into the abdominal aorta. If necessary, the injection is repeated after 48 hours. Preparations comprising silver have high anti-bacterial activity and can be used in the treatment of any etiology mastitis.

However, this method labor intensive. Also known is a method of using intramammary introduction of the pair milk containing large amounts of lysozyme (received from healthy cows) 1-2 times a day during 2-3 days. The method is not very effective, but milk and products of slaughter can be used after this treatment without any restriction. Also known is a method of treatment of subclinical mastitis using preparations on the basis of probiotics comprising a culture of *Str. thermophilus* and other bifido-lactobacilli. These drugs are injected intracisternally 1-2 times per day. At the hidden mastitis recovery begins after 1-2 injections for 2-3 days. Disadvantages of this method are an accident bacterial contamination of milk, appearing of new irritation of parenchymatous tissue of lactiferous gland, and as a consequence and potential exacerbation of the pathologic process. Also known is a method of treating mastitis of cows by using interferon solutions. These solutions increase the protective function of leukocytes which are present in a large amount in milk of animals with mastitis. The solutions contain at least 1000 units of recombinant bovine interferon which is packed in 10 g injectors. The solutions are used intracisternally twice a day with an interval of 8-14 hours for 3 days or until complete recovery. Recovery time is 4-12 days. The advantages of this method is the absence any limits for the use of milk and meat from treated animals, it doesn't lead to resistance of pathogenic organisms and it has no locally-irritating and resportive-toxic properties. The disadvantages of this method are the necessity of repeated application of the preparation and the presence of protein components that can provoke allergic reactions.

Digital dermatitis (DD), interdigital dermatitis (ID) and interdigital phlegmone (IP), which are the most common infectious hoof and claw diseases, are sporadically distributed worldwide but may be endemic in particular in intensive beef or dairy cattle production units. The incidence depends amongst other on weather, season of year, grazing periods, and housing system. DD usually leads to lameness and to a significant decrease in body weight, loss of fertility and decrease of milk production. The incidence can be between 5% and 30%. In the first epidemic cases about 30% to 80% animals can show clinical sings of the disease. However, on an average IP accounts only for up to 15% of the claw diseases.

It was surprising that a lot of researchers suggest that the etiological factors of DD, ID and IP are the same microorganisms, such as *Dichelobacter nodosus, Fusobacterium necroforun* and *Fusobacterium*, spp which first destroy the epidermis and allow the spirochetes from *Treponema* spp such as *T. phagedenis, T. vincentii*, and *T. denticola* to gain entrance into deeper tissues for developing the clinical sings of DD. Other bacterial species isolated from pathological material from tissues affected with DD, ID and IP are *Campylobacter* spp, *Staphylococcus aureus, Escherichia coli, Arcanobacterium pyogenes*, and *Prevotella* spp. Also, it was suggested that a virus plays an important role in the pathogenesis of the diseases.

The typical treatment strategy for DD, ID and IP is the application of antibiotics, antibacterial preparations and topical applications pads with antibiotics, antiseptics and astringent solutions. All known vaccines often fail to elicit a sufficient immune response and to protect the animals against interdigital dermatitis and interdigital phlegmone. There are no effective vaccines against digital dermatitis.

Many treatments of allergy are known and depend on the clinical picture of the allergy. For the treatment of acute allergic contact dermatitis, chronic allergic contact eczema and/or atopic eczema usually lipophilic creams comprising glucocorticosteroids, anti-microbial substances, anti-inflammatory drugs and/or calcium are used. For the treatment of other allergic dermatitis various compounds have been applied locally or parenterally, for example steroid preparations, salicylates, oils or peptides isolated from microorganisms. All of the above methods only treated the symptoms and not the causes of allergy. Also known are agents for treating allergy comprising antigenic material from keratinophilic fungi and yeasts as described in WO 97/07232. The antigenic material disclosed in WO 97/07232 comprises polysaccharides and/or glycopeptides obtained from keratinophilic fungi and yeasts. The antigenic preparations can be used as pharmaceutical compositions as well as vaccines for the treatment of animals and humans, especially for the treatment of allergies and for modulating the immune response. They can be of immunological as well as of pharmacological utility.

The object of the present invention is the provision of a more effective immunobiological product/preparation. It is also an object of the present invention to provide a new agent for use in veterinary and/or human medicine. Another object of the present invention is the provision of new agents for treating and/or preventing mastitis, preferably latent mastitis and/or acute mastitis, endometritis, preferably chronic, acute and/or purulent-catarrhal endometritis, hoof- and claw diseases, lameness, lesions in the interdigital space, digital dermatitis, interdigital dermatitis, interdigital phlegmon, trichophytosis, microsporosis, mycosis of skin, allergies, as well as diseases complicated by allergies, in particular allergic obstructive pulmonary disease, allergic skin diseases, allergic ear erythema, allergic rhinitis, allergic conjunctivitis, acute allergic contact dermatitis, chronic allergic contact eczema or atopic eczema, obstructive pulmonary disease, in particular chronic obstructive pulmonary disease, skin diseases, in particular dermatitis, ear erythema, rhinitis, conjunctivitis, dermatophytosis or warts, in particular Common warts, in a subject and for modulating the immune response in a subject and/or for enhancing reproduction efficiency, preferably reproduction efficiency in animal breeding.

These objects are solved by the subject matter defined in the claims.

The following figures serve to illustrate the invention.

FIG. 1 illustrates a standard curve for 1,3-ß-D-Glucan quantification. Shown is the mean rate of optical density change plotted over known concentrations [pg/ml] of 1,3-ß-D-Glucan Standard Solutions. For Standard curve generation 1,3-ß-D-Glucan Solutions of 100 pg/ml, 50 pg/ml, 25 pg/ml, 12.5 pg/ml and 6.25 pg/ml were prepared as recommended by the manufacturer. The measured curve was linear over the entire range and meets the quality control acceptance criteria ($R^2 > 0.980$).

Figure 2:
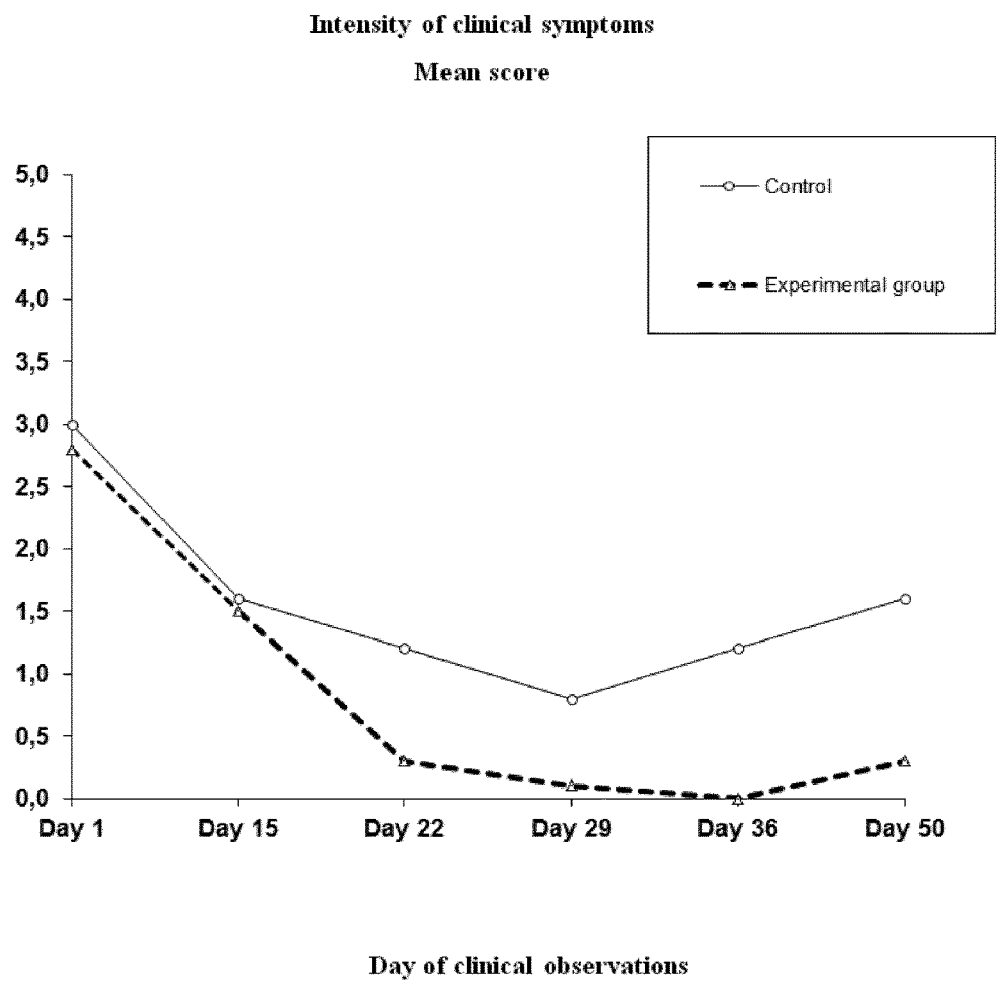

FIG. 2 illustrates the dynamics of the intensity of the clinical symptoms of allergic bronchitis in horses after application of the composition prepared according to example 41 (experimental group) and without vaccination (control group). The composition was injected 3 times with an interval of 4 days. The score of clinical symptoms is as follows: 0=no symptoms; 1=weak wheeze, without coughing; 2=weak wheeze, with coughing; 3=expressed wheeze; 4=expressed wheeze with clinical symptoms of depression.

Figure 3:
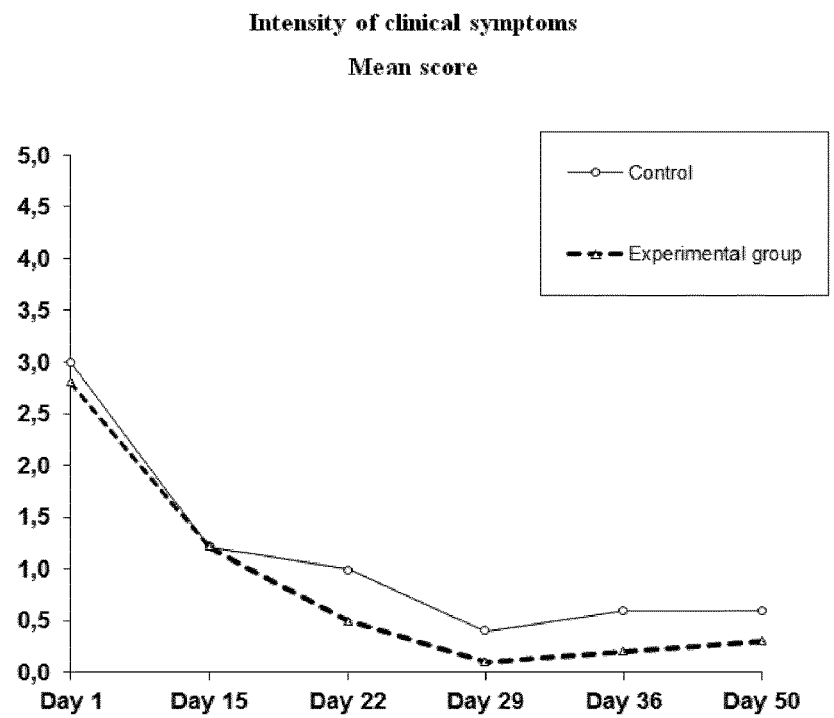

FIG. 3 illustrates the dynamics of the intensity of the clinical symptoms of chronic obstructive pulmonary disease in horses after application of the composition prepared according to example 41 (experimental group) and without vaccination (control group). The composition was injected 3 times with an interval of 4 days. The score of clinical symptoms is as follows: 0=no symptoms; 1=weak wheeze, without coughing; 2=weak wheeze, with coughing; 3=expressed wheeze; 4=expressed wheeze with clinical symptoms of depression.

Figure 4:
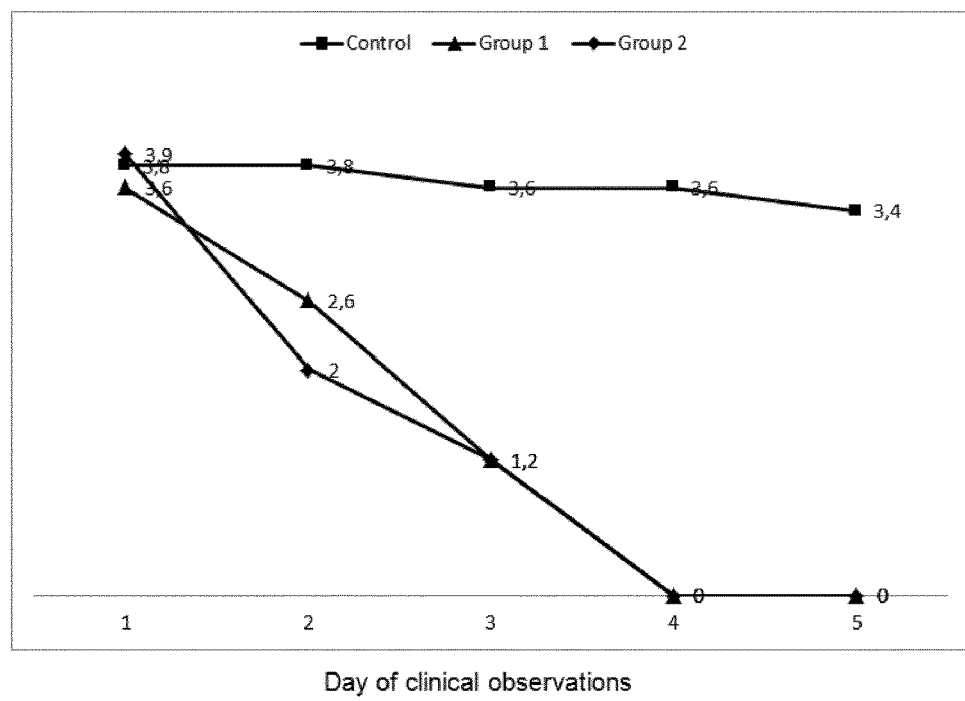

FIG. 4 illustrates the dynamics of clinical signs of skin diseases in dogs immunized with the composition according to Example 42 in doses of 0.5 ml and 1.0 ml (Mean score of clinical symptoms in each group was shown; n=10). The composition was injected 3 times with an interval of 7 days. The score of clinical symptoms is as follows: 0=no symptoms; 1=hair growth, active rejection of crusts or excessive flaking; 2=alopecia, no hair growth, rejection of crusts; 3=desquamation, swelling or swelling with crust, crust not rejected; 4=desquamation or swelling, pain on palpation; 5=inflammatory response, necrotic crust.

Figure 5:
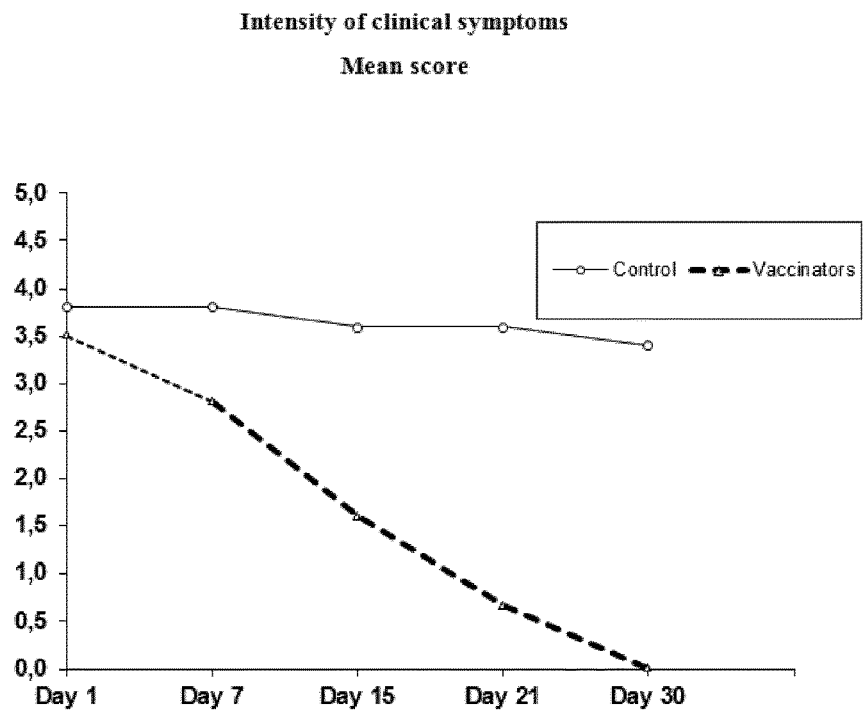

FIG. 5 illustrates the dynamics of clinical signs of skin diseases in dogs immunized with the composition according to Example 50 in doses of 0.5 ml. (Mean score of clinical symptoms in each group was shown; in vaccinators n=15 and in control group n=15). The composition was injected 3 times with an interval of 3 to 4 days. The score of clinical symptoms is as follows: 0=no symptoms; 1=hair growth, active rejection of crusts or excessive flaking; 2=alopecia, no hair growth, rejection of crusts; 3=desquamation, swelling or swelling with crust, crust not rejected; 4=desquamation or swelling, pain on palpation; 5=inflammatory response, necrotic crust.

Figure 6:
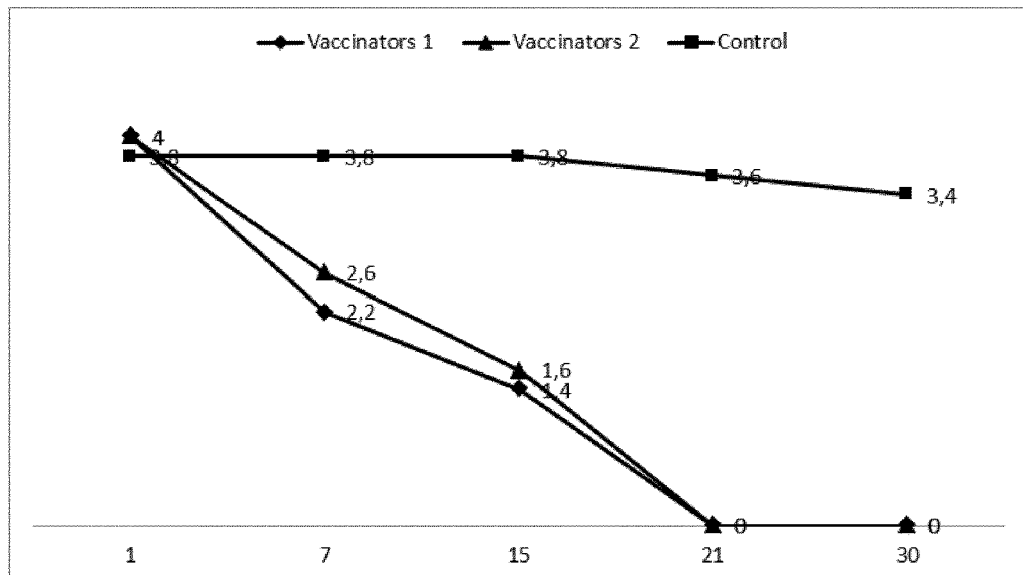

FIG. 6 illustrates the dynamics of clinical signs of skin diseases in dogs immunized with composition according to Examples 41 and 43 in a dose of 0.5 ml (Mean score of clinical symptoms in each group was shown; n=10). The score of clinical symptoms is as follows: 0=no symptoms; 1=hair growth, active rejection of crusts or excessive flaking; 2=alopecia, no hair growth, rejection of crusts; 3=desquamation, swelling or swelling with crust, crust not rejected; 4=desquamation or swelling, pain on palpation; 5=inflammatory response, necrotic crust.

Figure 7:
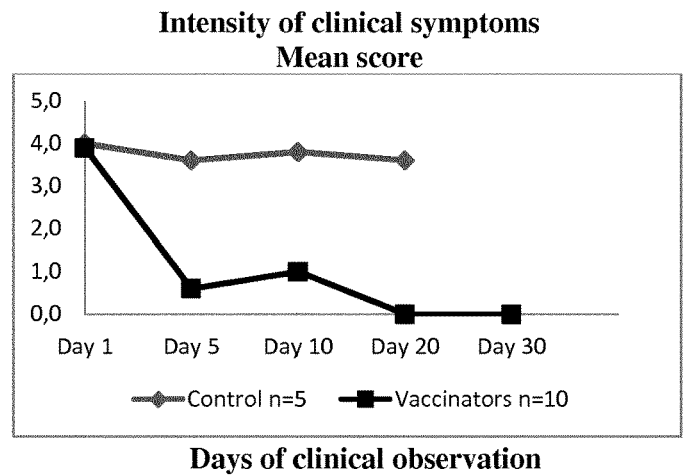

FIG. 7 illustrates the dynamics of clinical signs of rhinitis in cats treated with the composition prepared according to Example 42. Experimental group of cats was treated with the composition. Two courses according to study protocol every day with 1-2 drops into the nose were done. The score of symptoms is as follows: 0=no symptoms; 1=hyperemia and/or swelling of the mucous membranes of the nasal passages; 2=slight discharge from the nose; 3=hyperemia and/or swelling of the mucous membranes of the nasal passages discharge from the nose; 4=difficulty breathing, hyperemia and swelling of the mucous membranes of the nasal passages, heavy discharge from the nose; 5=death of animals.

Figure 8:
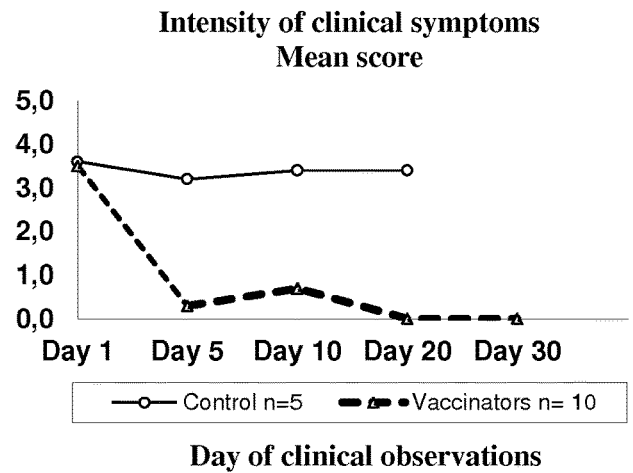
Figure 9:
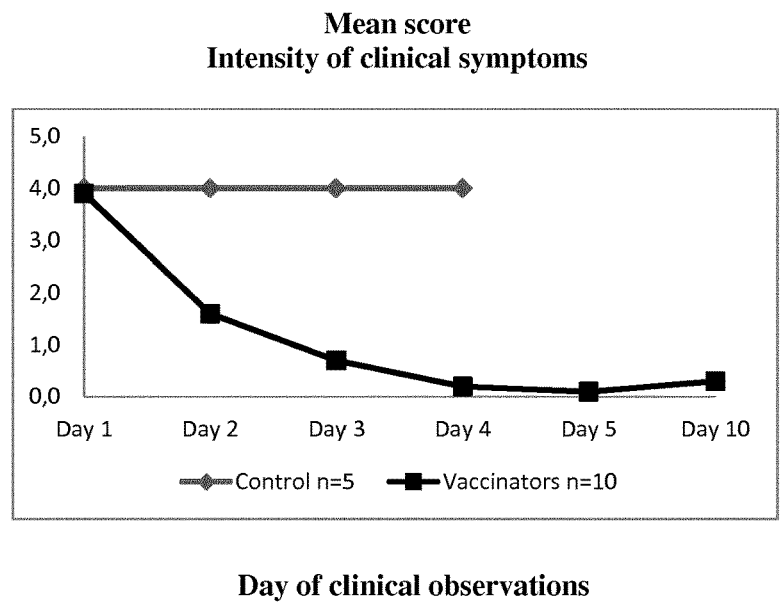

FIG. 8 illustrates the dynamics of clinical signs of rhinitis in dogs treated with the composition prepared according to Example 43. Experimental group of dogs was treated with the composition. Two courses according to study protocol every day with 1-2 drops into the nose were done. The score of symptoms is as follows: 0=no symptoms; 1=hyperemia and/or swelling of the mucous membranes of the nasal passages; 2=slight discharge from the nose; 3=hyperemia and/or swelling of the mucous membranes of the nasal passages discharge from the nose; 4=difficulty breathing, hyperemia and swelling of the mucous membranes of the nasal passages, heavy discharge from the nose; 5=death of animals FIG. 9 illustrates the dynamics of clinical signs of conjunctivitis in cats treated with the composition prepared according to Example 54. Experimental group of cats was treated with the composition according to study protocol every day by instilling 1-2 drops on the conjunctiva.

The score of symptoms is as follows: 0=no symptoms; 1=hyperemia and/or swelling of the conjunctiva; 2=slight lacrimation; discharge from the eyes; 3=hyperemia and/or swelling of the conjunctiva, discharge from the eyes; 4=hyperemia and swelling of the conjunctiva, intensive discharge from the eyes; 5=destruction of eyeball.

The use of the word "a" or "an" when used in conjunction with the term "comprising" in the claims and/or the description may mean "one," but it is also consistent with the meaning of "one or more," "at least one," and "one or more than one."

The term "about" means that the value stated, plus or minus 5% of the stated value, or the standard error for measurements of the given value, are contemplated.

The term "comprising" as used herein shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e. excluding the presence of additional other matter) and "comprising but not consisting of" (i.e. requiring the presence of additional other matter), with the former being more preferred.

The term "chitosan" as used herein refers to a copolymer of 2-amino-2-deoxy-D-Glucopyranose and 2-acetamido-2-deoxy-D-glucopyranose, where the degree of deacetylation is more than 50%, preferably more than 60%, 70%, 80% or 90%. Chitosan may be chemically derived from chitin which is a poly-1,4-β-N-acetyl-D-glucosamine, more particularly a N-acetyl-1,4-β-D-glucopyranosamine by deacetylation. Typical chitosan preparations have varying molecular weights depending on the method of manufacture.

The term "mastitis" as used herein refers an inflammation of breast and udder tissue. It preferably comprises latent mastitis and/or acute mastitis. Latent mastitis may also be called hidden mastitis and/or subclinical mastitis. Preferably, latent mastitis can be diagnosed by a well-known method in the art with 2% solution of mastidin. Acute mastitis may also be fibrinous, catarrhal, purulent-catarrhal, hemorrhagic mastitis with visual typical clinical symptoms of disease.

The term "endometritis" as used herein refers to an inflammation of the endometrium. More preferably, it refers to an inflammation of a mucous membrane of the uterus, which may be followed by a more or less significant change of the endometria and an increased activity of the healthy or regenerated uterine glands. Preferably, it comprises chronic endometritis, subacute, acute and subclinical (hidden) endometritis. The nature of inflammation is divided into catarrhal, catarrhal-purulent, purulent, fibrinous and hidden.

Endometritis may also be called uteritis. Uteritis is most frequently followed by reproduction of polymorphic microflora.

The term "trichophytosis" as used herein refers to a disease due to an infection with fungi from genera *Trichophyton*. Cattle is usually infected by *Trichophyton verrucosum* while humans, dogs, cats, horses, fur-bearing and other animals are usually infected by *T. mentagrophytes*. Humans can also be infected by *T. rubrum*. It may also be called *Trichophyton* disease.

The terms "microsporosis" or "*Microsporum canis* disease" as used herein refer to a disease due to an infection with genera *Microsporum*, more preferably with *Microsporum canis*. Typically cats, dogs, horses and other animals are infected by this disease. It is especially common in pigs, which are mostly infected by *Microsporum nanum*.

The term "warts" as used herein refers in general to a small, rough growth resembling a cauliflower or to a solid blister. Normally, warts are caused by a viral infection. Preferably, the term "warts" refers to Common warts, in particular verrucae volgares and paronychial warts.

The term "hoof- and claw disease" as used herein refers in particular to infectious hoof- and claw diseases in bovidae and/or pigs. Said diseases are in particular caused by bacteria, fungi and/or viruses. In particular the term "hoof- and claw diseases" refers to digital dermatitis, interdigital dermatitis and interdigital phlegmon.

The term "bovidae" as used herein refers in particular to cloven-hoofed, ruminant mammals including includes bison, African buffalo, water buffalo, antelopes, gazelles, sheep, goats, muskoxen, and cattle.

The term "lameness" as used herein refers in particular to lameness as a result of an infection and damage to tissue. In particular, the term "lameness" refers to lameness due to hoof and claw diseases, more particularly due to digital dermatitis (DD), interdigital dermatitis (ID) and interdigital phlegmon (IP).

It was now surprisingly found, that a composition comprising chitosan modified by an organic carboxylic acid or a salt thereof stimulates the immune response and can be used in a method of treating and/or preventing a number of different diseases. In addition, it was surprisingly found that if already known active agents are administered in combination with a modified chitosan of the present invention, said active agents can be used in an up to 50 times less dose.

Thus, the present invention relates to chitosan modified by an organic carboxylic acid, or a salt thereof. Preferably, the modified chitosan is a clear gel with an absent or faint smell of acetic acid. The modified chitosan of the present invention has preferably a molecular weight or an average molecular weight of about 50 Da to about 700 kDa, in particular of about 15 kDa to about 500 kDa, more particular of about 15 kDa to about 150 kDa, or of about 80 kDa to about 200 kDa, of about 150 kDa to about 300 kDa, of about 100 kDa to about 250 kDa or of about 300 kDa to about 700 kDa. The mass content of ashes of the modified chitosan according to the present invention is preferably about 0.2 to 2%, more preferably about 0.8 to about 1.2% and most preferably 0.22%. The modified chitosan according to the present invention may also be called chitosan derivative or chitosan variant.

Preferably, the modified chitosan have reactive amino groups in an amount of about 100 to about 500 per 100 kDa of chitosan. The modified chitosan according to the present invention has preferably a degree of deacetylation of about 62% to about 98%, more preferably of about 80 to about 95%, more preferably of about 89% to about 93%, or of about 89% to about 98%, of about 93% to about 98%, of about 93% to 95% or of about 95% to 98%.

In a preferred embodiment of the present invention the modified chitosan, chitosan derivative or chitosan variant is a compound of formula [X]n, in which n represents an integer of about 1 to about 5000, in particular an integer of about 300 to about 4000, and X has the following formula (1):

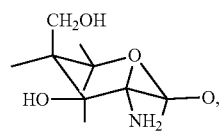

wherein about 2 to about 38% of the X residues constituting said compound are modified by acetylation and wherein all or part of the X residues constituting said compound are modified by an organic carboxylic acid or a salt thereof.

Thus, the present invention also refers to A compound of formula [X]n, in which n represents an integer of about 1 to about 5000, in particular an integer of about 300 to about 4000, and X has the following formula (1):

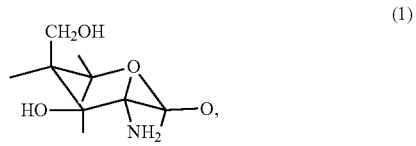

wherein about 2% to about 38%, more preferably about 5% to about 20% of the X residues constituting said compound are modified by acetylation and wherein all or part of the X residues constituting said compound are modified by an organic carboxylic acid or a salt thereof.

The formula X refers to a deacetylated 2-amino-2-deoxy-D-glucose unit and a D-glucosamine unit, respectively, which is the monomer of 100% deacetylated chitosan. Accordingly, the formula X may also refer to the formula represented in the square brackets of the following formula (2) representing the structural formula of a chitosan with a degree of deacetylation of 100%:

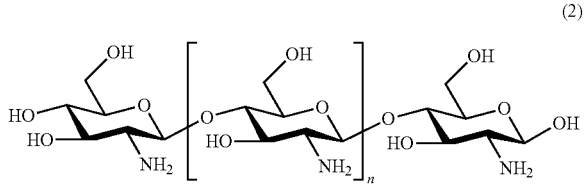

As outlined above n represents an integer of about 1 to about 5000. Within that limit n is preferably at least about 10, about 50, about 80, about 100, about 200, about 300, about 400, about 500, about 600, about 700, about 800, about 900 or about 1000 and/or at most about 4000, about 3000, about 2500, about 2000 or about 1500. In further preferred embodiments of the present invention n represents an integer of about 50 to about 2500, in particular of about 50 to about 1000, or of about 300 to about 1500, of about 1000 to about 2000, of about 400 to about 1700, of about 50 to about 1700 or of about 1000 to about 5000.

In a further preferred embodiment of the present invention about 5% to about 35%, more preferably about 5% to about 20%, more preferably about 7% to about 11% or about 2% to about 7%, about 5% to about 7% or about 2% to about 5% of the X residues constituting the compound as defined above are modified by acetylation, which means that they are acetylated. A modification by acetylation refers to the introduction of an acetyl functional group into the residue according to formula (1) which results in a N-acetyl-D-glucosamine-residue.

In a preferred embodiment of the present invention the organic carboxylic acid has a pKs of about 2 to about 5, more preferably of about 2.3 to about 4.9. More preferably, the organic carboxylic acid, or a salt thereof is selected form the group consisting of valeric acid, valeric acid chloride, para-aminobenzoic acid, glucuronic acid, and lactic acid. The modification with the organic carboxylic acid or a salt thereof is preferably obtainable by the contact or a reaction with said organic carboxylic acid or a salt thereof or an aqueous solution comprising said organic carboxylic acid or a salt thereof. Preferably, the modification takes place by the contact with an aqueous solution comprising about 0.2 M to about 22.5 M of said organic carboxylic acid or a salt thereof, or in an aqueous solution comprising about 1 mM to about 100 mM of the organic carboxylic acid or a salt thereof, more preferably about 1 mM to about 10 mM.

In a preferred embodiment of the present application the modified chitosan, chitosan derivative or chitosan variant is a Polyamino-sugar colloid, preferably a hydro colloid. In a preferred embodiment of the present application the modified chitosan, chitosan derivative or chitosan variant is a Chitosan-Glucuronic acid-Hydro-Colloid or Chitosan-p-Aminobenzoic acid-Hydro-Colloid or Chitosan-Valeric acid-Hydro-Colloid. In another preferred embodiment of the present application the Chitosan-Glucuronic acid-Hydro-Colloid has the chemical formula: $(C_6H_{11}O_4N)_x(C_8H_{13}O_5N)_y(C_6H_{10}O_7)_z(H_2O)_m$. Preferably, the Chitosan-Glucuronic acid-Hydro-Colloid has the following molecular weight: $x*(161)+y*(203)+z*(194.14)+m*(18)$. In another preferred embodiment of the present application the Chitosan-p-Aminobenzoic acid-Hydro-Colloid has the chemical formula: $(C_6H_{11}O_4N)_x(C_8H_{13}O_5N)_y(C_7H_7O_2N)_z(H_2O)_m$. Preferably, the Chitosan-p-Aminobenzoic acid-Hydro-Colloid has the following molecular weight: $x*(161)+y*(203)+z*(137.14)+m*(18)$. In another preferred embodiment of the present application the Chitosan-Valeric acid-Hydro-Colloid has the chemical formula: $(C_6H_{11}O_4N)_x(C_8H_{13}O_5N)_y(C_5H_{10}O_2)_z(HCl)_z(H_2O)_m$. Preferably, Chitosan-Valeric acid-Hydro-Colloid has the following molecular weight: $x*(161)+y*(203)+z*(102)+z*(36.5)+m*(18)$.

Thus, the present application also refers to a hydro colloid comprising:

(i) 0.1% to 5% (w/v) chitosan and 0.001 to 5% (w/v) valeric acid, or a salt thereof, preferably chloride of valeric acid or (ii) 0.1% to 5% (w/w) chitosan and 0.001 to 5% (w/w) glucuronic acid or p-aminobenzoic acid or a salt thereof.

A preferred embodiment of the present invention refers to a hydro colloid comprising:

(i) 0.1% to 3% (w/v) chitosan and 0.001 to 2% (w/v) valeric acid or a salt thereof, preferably chloride of valeric acid, or (ii) 0.1% to 3% (w/w) chitosan and 0.001 to 2% (w/w) glucuronic acid or p-aminobenzoic acid or a salt thereof.

Another preferred embodiment of the present invention refers to a hydro colloid comprising:

(i) 0.1% to 1.2% (w/v) chitosan and 0.001 to 1% (w/v) valeric acid or a salt thereof, preferably chloride of valeric acid, or (ii) 0.1 to 1.2% (w/w) chitosan and 0.001 to 1% (w/w) glucuronic acid or p-aminobenzoic acid or a salt thereof.

Another preferred embodiment of the present invention refers to a hydro colloid comprising:

(i) 0.1% to 1.2% (w/v) chitosan and (ii) 0.01 to 0.44% (w/v) valeric acid, or a salt thereof, preferably chloride of valeric acid.

Another preferred embodiment of the present invention refers to a hydro colloid comprising:

(i) 0.1% to 1.2% (w/w) chitosan and (ii) 0.001 to 0.6% (w/w) glucuronic acid or a salt thereof.

Another preferred embodiment of the present invention refers to a hydro colloid comprising:

(i) 0.1% to 1.2% chitosan and (ii) 0.006 to 1% (w/w) p-aminobenzoic acid or a salt thereof.

Preferably the chitosan of the hydro colloid is a compound of formula [X]n, in which n represents an integer of about 1 to about 5000, in particular an integer of about 300 to about 4000, and X has the following formula (1):

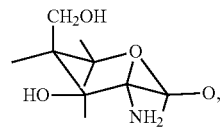

wherein about 2% to about 38%, more preferably about 5% to about 20% of the X residues constituting said compound are modified by acetylation and wherein all or part of the X residues constituting said compound are modified by an organic carboxylic acid or a salt thereof, In a preferred embodiment, the remaining percentage of the hydro colloid according to the present invention is provided by the dispersion media, preferably water or water and hydrogenchloride (HCl).

In a preferred embodiment, the hydro colloid according to the present invention is used as a dilution, preferably in a dilution of 0 to 10 times.

In another preferred embodiment of the present application the modified chitosan, chitosan derivative or chitosan variant is a natural white to yellowish viscous liquid. Preferably, the modified chitosan, chitosan derivative or chitosan variant has typical odor of the carboxylic acid, preferably the typical odor of valeric acid.

In another preferred embodiment, the modified chitosan, chitosan derivative or chitosan variant contains about 0.2% pentanoyl chloride, or 0.2% Glucuronic acid, or 0.2% p-Aminobenzoic acid.

In another preferred embodiment, the modified chitosan, chitosan derivative or chitosan variant contains 1% chitosan residue from drying chitosans.

In another preferred embodiment, the modified chitosan, chitosan derivative or chitosan variant has about 10 to about 1000 mOsmol, preferably about 10 to about 200 mOsmol, most preferably about 100 mOsmol.

In a preferred embodiment of the present invention the modified chitosan is further modified by a mineral acid. Said modification may result from the contact or a reaction with said mineral acid or an aqueous solution comprising said mineral acid. Said mineral acid is preferably HCl or $H_2SO_4$. Preferably, the modification takes place by incubating the modified chitosan in an aqueous solution comprising about 0.05 M to about 1 M of said mineral acid, preferably HCl or $H_2SO_4$.

The present invention also refers to a composition comprising a modified chitosan, chitosan derivative or chitosan variant or a hydro colloid according to the present invention. Preferably, the composition comprising said modified chitosan is a clear gel with an absent or faint smell of acetic acid which is soluble in water and in 1% solution of acetic acid. The composition has preferably a molecular weight or an average molecular weight of about 50 Da to about 700 kDa, in particular of about 15 kDa to about 500 kDa, more particular of about 15 kDa to about 150 kDa, or of about 80 kDa to about 200 kDa, of about 150 kDa to about 300 kDa, of about 100 kDa to about 250 kDa or of about 300 kDa to about 700 kDa. The mass content of ashes of the composition according to the present invention is 0.1 to 2%, preferably about 0.8 to about 1.2%, more preferably about 0.22%.

Preferably, the modified chitosan of said composition has reactive amino groups in an amount of about 100 to about 500 per 100 kDa of chitosan. The modified chitosan of the composition according to the present invention has preferably a degree of deacetylation of about 65% to about 98%, more preferably of about 80% to about 95%, more preferably of about 89% to about 93%, or of about 89% to about 98%, of about 93% to about 98%, of about 93% to about 95% or of about 95% to about 98%.

In further preferred embodiment of the present invention, the composition comprises additionally a mineral acid. Said mineral acid supports the solubility of the modified chitosan and/or may further modify the chitosan. Said mineral acid is preferably HCl or $H_2SO_4$. The aqueous solution comprises preferably 0.05 M to about 1 M mineral acid, preferably HCL or $H_2SO_4$.

The modified chitosan according to the present invention is preferably obtainable by contacting chitosan with an organic carboxylic acid or salt thereof. Said contact is preferably performed by incubating chitosan in an aqueous solution of an organic carboxylic acid or a salt thereof, more preferably by incubating chitosan in an aqueous solution of valeric acid, lactic acid, para-aminobenzoic acid or glucuronic acid or a salt thereof, in particular chloride of valeric acid. Preferably, said incubation is performed by mixing and/or under stirring.

Thus, the present invention relates to a modified chitosan obtainable by a method comprising
(a) incubating chitosan in an aqueous solution of an organic carboxylic acid or a salt thereof.

The present invention also relates to a method comprising the step of:
(a) incubating chitosan in an aqueous solution of an organic carboxylic acid or a salt thereof.

In a preferred embodiment the chitosan is firstly dissolved under acidic aqueous conditions and subsequently precipitated by increasing the pH value to a pH value of about 8.0 to about 8.5 before it is incubated in the aqueous solution of the organic carboxylic acid or the salt thereof as described above.

Thus, the present invention also relates to a modified chitosan obtainable by a method comprising
(i) dissolving chitosan in an aqueous solution of an acid
(ii) increasing the pH value until chitosan is precipitated
(iii) recovering the precipitated chitosan, and
(a) incubating the recovered chitosan of step (iii) in an aqueous solution of an organic carboxylic acid or a salt thereof.

The present invention also relates to a method comprising the steps of:
(i) dissolving chitosan in an aqueous solution of an acid
(ii) increasing the pH value until chitosan is precipitated
(iii) recovering the precipitated chitosan, and
(a) incubating the recovered chitosan of step (iii) in an aqueous solution of an organic carboxylic acid or a salt thereof.

The organic carboxylic acid or a salt thereof of step (a) has preferably a pKs of about 2 to about 5, more preferably of about 2.3 to about 4.9. More preferably said organic carboxylic acid is valeric acid, lactic acid, para-aminobenzoic acid or glucuronic acid or a salt thereof, in particular chloride of valeric acid. Said carboxylic organic acid or a salt thereof is preferably used in a concentration of about 0.2 M to about 22.5 M. The incubation of chitosan and the recovered chitosan of step (iii), respectively, and the aqueous solution of the organic carboxylic acid or a salt thereof as outlined in step (a) results in the solution of the chitosan, the modification of the chitosan and/or the formation of a gel. Preferably, the pH value of the aqueous solution in step (a) is about 5 to about 6 or about 5.0, 5.1, 5.2, 5.3, 5.4, 5.5, 5.6, 5.7, 5.8, 5.9 or 6.0. Preferably, the modification of the chitosan takes place in an aqueous solution comprising about 1 mM to about 100 mM of the organic carboxylic acid or a salt thereof, more preferably about 1 mM to about 10 mM.

Preferably, step (a) is performed until the chitosan is modified and dissolved. It is preferably performed by mixing chitosan with an aqueous solution of the organic carboxylic acid or a salt thereof or by suspending chitosan under aqueous conditions and adding the organic carboxylic acid to the suspension. It is preferably performed under stirring for about 1 to about 72 hours, more preferably for about 24 to about 48 hours. Step (a) may comprise the addition of a further acid or may be performed in the presence of a further acid. Said further acid is preferably a mineral acid, an organic acid or a salt of said mineral acid or organic acid. Preferably, the mineral acid is HCl or $H_2SO_4$ and the organic acid is glutamic acid, para-aminobenzoic acid or lactic acid. The mineral or organic acid is preferably added or present in an amount to adjust the pH value of the mixture of step (a) to a pH value of about 5 to about 6 or about 5.0, 5.1, 5.2, 5.3, 5.4, 5.5, 5.6, 5.7, 5.8, 5.9 or 6.0. The addition of a further acid may support the dissolution and/or the modification of the chitosan e.g. by decreasing the time which is necessary to dissolve the modified chitosan.

The concentration of chitosan in step (a), or if the method comprises a step (i) for step (i), is preferably about 1 g to about 20 g chitosan per liter, more preferably about 5 g to about 15 g chitosan per liter, most preferably about 8 to about 10 g chitosan per liter.

The chitosan used for step (a), or if the method comprises a step (i) for step (i), may be commercially available chitosan or isolated from any natural source comprising chitosan such as biomass comprising chitosan. Alternatively, chitin may be used which is deacetylated to obtain chitosan prior to step (a), or if the method comprises a step (i) prior to step (i). Said chitin may be commercially available or it may be isolated from a natural source comprising chitin such as biomass comprising chitin. The biomass for chitin and/or chitosan isolation is preferably biomass of fungi, insects and/or crustaceans.

The deacetylation of chitin can be performed by known methods in the art as e.g. by using sodium hydroxide (NaOH) in excess as a reagent and water as a solvent or by enzymatic methods. The isolation of chitosan and/or chitin from natural sources can also be performed by known methods in the art and by the methods described in the Examples of the present invention.

The chitosan used for step (a), or if the method comprises a step (i) for step (i), has preferably a degree of deacetylation of about 62% to about 95%, more preferably of about 80% to about 94%, more preferably of about 89% to about 93% or of about 93% to about 98%, of about 93% to 95%, of about 95% to about 98%, or of at least 60%, more preferably of at least 70%, 80%, 90% or 95%, or a degree of deacetylation of about 60% to about 100%, more preferably of about 80% to about 95%, even more preferably of about 90% to about 95%, most preferably about 77% to about 80%.

The chitosan used for step (a), or if the method comprises a step (i) for step (i), has preferably a viscosity of about 50 to 400 MPas, more preferably about 70 to about 150 MPas or about 151 to about 350 MPas.

The chitosan used for step (a), or if the method comprises a step (i) for step (i), has preferably a molecular weight or an average molecular weight of about 50 Da to about 700 kDa, in particular of about 15 kDa to about 500 kDa, more particular of about 15 kDa to about 150 kDa, or of about 80 kDa to about 200 kDa, of about 150 kDa to about 300 kDa, of about 100 kDa to about 250 kDa or of about 300 kDa to about 700 kDa.

Before the chitosan is used in step (a), or if the method comprises a step (i) in step (i), the chitosan may be sterilized by autoclaving. Said sterilization may result in that the modified chitosan according to the present invention is less toxic, better tolerated by any subject and/or results in less unintended side-effects.

Preferably, step (i) is performed by the use of an aqueous solution of an weak acid, preferably by an organic acid or a salt thereof, more preferably by acetic acid, valeric acid, lactic acid, para-aminobenzoic acid or glucuronic acid or a salt thereof, in particular chloride of valeric acid. The acid is preferably used in a concentration of about 0.8% to about 2%. Step (i) is preferably performed under stirring. The stirring may be performed for about 2 hour to about 24 hours. Preferably, step (i) is performed until a gel or gel suspension is obtained. Unsolved particles may be removed, e.g. by filtration. For example, a metal grid with a cell of 200 µm to 300 µm may be used for such a filtration.

Step (ii) is preferably performed by increasing the pH value of the gel or gel suspension obtained in step (i) until a precipitate is formed. It is preferably performed under stirring. It is preferably performed by treating chitosan under aqueous alkaline conditions, more preferably under aqueous alkaline conditions comprising about 0.1 to about 25.0% alkali. In a preferred embodiment the alkali is NaOH. Preferably, said step is performed at a temperature of about 4° C. to about 55° C. Preferably, the treatment is performed for about 20 min to about 2 hours, more preferably for about 30 min to about 70 min, but it may also take up to about 24 h. Preferably, the pH value is increased by adding the alkali to the gel or gel suspension of step (i). Preferably, the pH value is increased to obtain a pH of about 8.0 to about 8.5. Step (ii) may result in a further deacetylation of the chitosan. It may also result in that the modified chitosan according to the present invention is less toxic, better tolerated by any subject and/or results in less unintended side-effects.

Step (iii) is preferably performed by centrifuging the mixture or suspension obtained in step (ii). The centrifugation is preferably performed at about 4000 to about 6000 revolution/min, more preferably at about 5000 revolution/min. The centrifugation is preferably performed for up to 60 minutes.

The methods by which the modified chitosan of the present invention is obtainable and the methods of the present invention may comprise additional steps. For example, the product obtained in step (ii), may be homogenized. Preferably, the step of homogenization is performed in a closed sterile homogenizer.

Alternatively or in addition, the product obtained in step (a) may be dialyzed. The dialysis is preferably performed in a closed system to remove free ions of salts and low molecular weight compounds. Preferably, the dialysis is performed by cross filtration for about 1 to about 6 hours or by membrane filtration against distillate water for about 24 to about 48 hours.

Alternatively or in addition, the methods by which the modified chitosan of the present invention is obtainable and the methods of the present invention may comprise a further step of preparing the final product. The preparation of the final product may comprise the dilution of the obtained product. Preferably, the product is diluted by the addition of water, more preferably of sterile water for injection. However, the product may also be diluted in any other suitable aqueous solution. Alternatively or in addition, the preparation of the final product may comprise the addition of one or more further compounds, such as diluents, preservatives, antibiotics, further active substances and/or antigenic material from microorganism and/or enzymes. Suitable preservatives are for example chlorocresol, thiomersal and formalin. Suitable antibiotics are for example neomycin, penicillin, gentamycin, cloxacillin, cephapirin and cephalosporin. Finally, the final product may be sterilized. Preferably the sterilization is performed by heating, preferably for about 40 to 50 minutes at a temperature of about 65° C. to about 80° C. Preferably, said sterilization is repeated one, two, three, four or five times.

Preferably, the final product has a concentration of about 0.02 g to about 2 g modified chitosan per liter, more preferably of about 0.04 to about 1 g modified chitosan per liter.

In a preferred embodiment the methods by which the modified chitosan of the present invention is obtainable and the methods of the present invention comprise the steps as described in the Examples. For example, the methods may comprise the following steps:

optionally sterilizing chitosan e.g. by autoclaving,
(i) dissolving chitosan in an aqueous solution of an acid, in particular in the presence of an acetic acid,
optionally removing undissolved particles e.g. by filtration,
(ii) increasing the pH value until chitosan is precipitated,
(iii) recovering the precipitated chitosan,
optionally homogenizing the recovered chitosan under aqueous conditions,
(a) incubating the recovered chitosan of step (iii) or the homogenized recovered chitosan in an aqueous solution of an organic carboxylic acid or a salt thereof, optionally in the presence of a further mineral acid or organic acid,
optionally dialyzing the product obtained in step (a),
optionally adding further compounds, such as diluents, preservatives, antibiotics, further active compounds such as chemotherapeutic preparations, and/or antigenic material from microorganism and/or enzymes, and
optionally sterilizing the final product e.g. by heating.

Preferably, the order of the steps as outlined above corresponds to the order as listed above. However, as known by the person skilled in the art the order of single steps may be varied as long as the same effects are achieved. For example, diluents such as water may be added in various stages of the method as described above.

If no specific temperature ranges are given for the method steps as described above, the steps are preferably performed at room temperature and/or in a range of about 10° C. to about 40° C., more preferably in a range of about 20° C. to about 30° C.

In a further preferred embodiment the present invention refers to a modified chitosan, chitosan derivative or chitosan variant and/or a composition comprising a modified chitosan, chitosan derivative or chitosan variant or hydro colloid obtainable by any method of the present invention.

In a further preferred embodiment the present invention refers to a composition comprising a modified chitosan, chitosan derivative or chitosan variant or a hydro colloid according to the present invention.

In addition, the composition of the present invention may comprise further active substances. Preferably, the composition of the present invention may additionally comprise a chemotherapeutic preparation, in particular if it is used for the treatment of mastitis.

In a further preferred embodiment of the present invention the composition of the present invention may additionally comprise antigenic material from microorganism and/or enzymes, in particular antigenic material of keratinophilic fungi and/or keratinophilic yeast-like fungi and/or yeasts.

The antigenic material of keratinophilic fungi or yeasts may be derived from any parts of keratinophilic fungi or yeasts comprising antigens such as from the mycelium, artrospores, dermatophyte microconidia, yeast blastospores or others. The antigens are preferably polysaccharides and/or glycopeptides. Preferably, the antigenic material of keratinophilic fungi or yeasts is selected from the group consisting of: homogenised inactivated dermatophyte microconidia, homogenised inactivated yeast blastospores, antigenic material of yeast blastospores and antigenic material of dermatophyte microconidia. Thus, the composition of the present invention may additionally comprise homogenised inactivated dermatophyte microconidia and/or homogenised inactivated yeast blastospores and/or antigenic material of yeast blastospores and/or dermatophyte microconidia.

The antigenic material of keratinophilic yeasts, in particular the yeast blastospores, belong preferably to the genus *Candida* and more preferably to the species *Candida albicans*. The antigenic material of keratinophilic dermatophyte, in particular the dermatophyte microconidia, belong preferably to the genera *Trichophyton, Microsporum* and/or *Chrisporium*. More preferably, the dermatophyte microconidia belong to the species *Trichophyton verrucosum, Trichophyton mentagrophytes, Trichophyton equinum, Trichophyton sarkisovii, Trichophyton rubrum, Microsporum canis, Microsporum gypseum* and/or *Chrisporium tropicum*. In particular, the species *Microsporum canis* can be *Microsporum canis* var. *obesum* and/or *Microsporum canis* var. *distortum*.

In a preferred embodiment of the present invention the yeast blastospores and the dermatophyte microconidia are obtained from strains of the above mentioned species which has been obtained by directed selection based on spore production and/or attenuation. It is highly preferred to use a strain which grow faster in nutrient medium, produces more microconidia and blastospores, respectively, has a lower virulence and/or no adverse reactions after its intramuscular application in comparison to any epizootic strain from which it is derived. Examples of such strains are the strains *Trichophyton mentagrophytes* DSM-7279, *Trichophyton verrucosum* DSM-28406, *Trichophyton rubrum* DSM-9469, *Trichophyton rubrum* DSM-9470, *Trichophyton rubrum* DSM-9471, *Trichophyton rubrum* DSM-9472, *Candida albicans* DSM-9456, *Candida albicans* DSM-9457, *Candida albicans* DSM-9458, and *Candida albicans* DSM-9459, *Chrisporium tropicum* DSM-28405 and *Microsporum canis* BINO 483. Thus, in especially preferred embodiments of the present invention the yeast blastospores and the dermatophyte microconidia are obtained from strains *Trichophyton mentagrophytes* DSM-7279, *Trichophyton verrucosum* DSM-28406, *Trichophyton rubrum* DSM-9469, *Trichophyton rubrum* DSM-9470, *Trichophyton rubrum* DSM-9471, *Trichophyton rubrum* DSM-9472, *Candida albicans* DSM-9456, *Candida albicans* DSM-9457, *Candida albicans* DSM-9458, *Candida albicans* DSM-9459, *Chrisporium tropicum* DSM-28405, and *Microsporum canis* BINO 483.

The strains *Trichophyton rubrum* DSM-9469, *Trichophyton rubrum* DSM-9470, *Trichophyton rubrum* DSM-9471, *Trichophyton rubrum* DSM-9472, *Candida albicans* DSM-9456, *Candida albicans* DSM-9457, *Candida albicans* DSM-9458, and *Candida albicans* DSM-9459 have been deposited according to the Budapest Treaty at the "Deutsche Sammlung von Mikroorganismen und Zellkulturen" (DSM), Mascheroder Weg 1B, W-38124 Braunschweig, Germany (which current name and address is "Leibniz-Institut DSMZ-Deutsche Sammlung von Mikroorganismen und Zellkulturen GmbH" (DMSZ), Inhoffenstraße 7B, 38124 Braunschweig, GERMANY) on 5 Oct. 1994 by the Basotherm GmbH, Eichendorffweg 5, 88396 Biberach an der Riss. The current depositors of said strains are the applicants, namely Dr. Igor Polyakov and Dr.sc.Dr. Liudmila Ivanova, Eberhardtstr. 40, 89073 Ulm.

*Trichophyton Rubrum*, No. DSM-9469

The strain was deposited at the DSM on May 10, 1994 under Serial No. DSM-9469. The strain was obtained by directed selection based on spore production and attenuation of the epizootic strain No. 533, which was identified on a skin of man in 1985. The strain was identified using the "Rebell-Taplin" key (Rebell, G., Taplin, D.: Dermatophytes, their recognition and identification, 3rd Print, University of Miami Press. Coral Gables, Fla., USA, 1978). The biological properties of the strain are described in Table A. Strain No. DSM-9469 differs from the epidemic strain in its faster growth in nutrient medium, an enormous production of microconidia and lower virulence.

TABLE A

| Properties and characteristics of the strains | Strain No. DSM-9469 | Epidemic Strain No. 533 |
| --- | --- | --- |
| Description of the culture | Mature 15-day colony on agar Sabouraud: white, velvety, flat, margin of the colony fringed, under surface yellow, in centre deep purple, diameter of colony 60-63 mm | 20-day colony on agar Sabouraud: white, downy, elevated, margin of colony regular, under surface purple, diameter of colony 30-35 mm |
| Morphological characteristics | Mature 15-day culture with septate branching hyphae 1-3 µm wide, numerous abovate oval microconidia measuring 2-3 × 3-5 µm, macroconidia long clavate pencil-shaped with 4-5 cross walls | 20-day culture with septate branching hyphae 1-3 µm wide, microconidia elevate to round in small open clusters and along the hyphae measuring 2-3 × 3-6 µm; macroconidia are rare, |

TABLE A-continued

| Properties and characteristics of the strains | Strain No. DSM-9469 | Epidemic Strain No. 533 |
|---|---|---|
| | measuring 4-6 × 15-40 µm. | long and pencil-shaped with 3-5 cross walls measuring 4-7 × 15-50 µm. |
| Pathogenic characteristics | The strain is weakly virulent. 9-10 days after application of a dose of 500-600 thousand cells of fungal material per cm$^2$ on scarified skin of guinea pigs, scales are formed. Spontaneous recovery after 18-20 days. | The strain is virulent. 9-10 days after application of a dose of 500-600 thousand cells of fungal material per cm$^2$ on scarified skin of guinea pigs, thin necrotic scabs are formed. Spontaneous recovery after 25-30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of guinea pigs with inactivated antigen from cultures (repeated not less than 5 times): establishes immunity | Results of immunisation of a group of guinea pigs with inactivated antigen from cultures (repeated not less than 5 times): establishes immunity |

*Trichophyton Rubrum*, No. DSM-9470

The strain was deposited at the DSM on May 10, 1994 under Serial No. DSM-9470. The strain was obtained by directed selection based on spore production and attenuation of the epizootic strain No. 535, which was identified on a skin of man in 1990. The strain was identified using the "Rebell-Taplin" key (Rebell, G., Taplin, D.: Dermatophytes, their recognition and identification, 3rd Print, University of Miami Press. Coral Gables, Fla., USA, 1978). The biological properties of the strain are described in Table B. Strain No. DSM-9470 differs from the epidemic strain in its faster growth in nutrient medium, an enormous production of microconidia and lower virulence.

TABLE B

| Properties and characteristics of the strains | Strain No. DSM-9470 | Epidemic Strain No. 535 |
|---|---|---|
| Description of the culture | Mature 15-day colony on agar Sabouraud: white velvety-fluffy in centre, folded, margin of colony regular, under surface colourless or rose, diameter of colony 25-30 mm | 20-day colony on agar Sabouraud: white, fluffy, margin of colony regular, under surface yellow, 20 mm in diameter |
| Morphological characteristics | Mature 15-day culture with septate branching hyphae 1-3 µm wide, round oval puriform microconidia measuring 2-3 × 3-7µm. | 20-day culture with septate branching hyphae 1-3 µm wide, microconidia clavate to round in small open clusters and along the hyphae measuring 2-3 × 3-6 µm; macroconidia are absent. |
| Pathogenic characteristics | The strain is weakly virulent. 9-10 days after application of a dose of 500-600 thousand cells of fungal material per cm$^2$ on scarified skin of guinea pigs, necrotic scabs are formed. | The strain is virulent. 9-10 days after application of a dose of 500-600 thousand cells of fungal material per cm$^2$ on scarified skin of guinea pigs, thin necrotic scabs are formed. Spontaneous recovery after 25-30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of guinea pigs with inactivated antigen from cultures (repeated not less than 5 times): establishes immunity | Results of immunisation of a group of guinea pigs with inactivated antigen from cultures (repeated not less than 5 times): establishes immunity |

*Trichophyton Rubrum*, No. DSM-9471

The strain was deposited at the DSM on May 10, 1994 under Serial No. DSM-9471. The strain was obtained by directed selection based on spore production and attenuation of the epizootic strain No. 620, which was identified on a nail of man in 1989. The strain was identified using the "Rebell-Taplin" key (Rebell, G., Taplin, D.: Dermatophytes, their recognition and identification, 3rd Print, University of Miami Press. Coral Gables, Fla., USA, 1978). The biological properties of the strain are described in Table C. Strain No. DSM-9471 differs from the epidemic strain in its faster growth in nutrient medium, an enormous production of microconidia and lower virulence.

TABLE C

| Properties and characteristics of the strains | Strain No. DSM-9471 | Epidemic Strain No. 620 |
|---|---|---|
| Description of the culture | Mature 15-day colony on agar Sabouraud: white, velvety, elevated, margin of colony regular, under surface yellow, in centre deep purple, diameter of colony 32-35 mm | 20-day colony on agar Sabouraud: white, downy, elevated, margin of colony regular, under surface purple, diameter of colony 20-25 mm |
| Morphological characteristics | Mature 15-day culture with septate branching hyphae 1-3 µm wide, round oval puriform microconidia measuring 2-3 × 3-7 µm. | 20-day culture with septate branching hyphae 1-3 µm wide, microconidia clavate to round in small open clusters and along the hyphae measuring 2-3 × 3-6 µm; macroconidia are rare, long and pencil-shaped with 3-5 cross walls measuring 4-7 × 15-50 µm. |
| Pathogenic characteristics | The strain is weakly virulent. 9-10 days after application of a dose of 500-600 thousand cells of fungal materials per cm$^2$ on scarified skin of guinea pigs, scales are formed. Spontaneous recovery after 18-20 days. | The strain is virulent. 9-10 days after application of a dose of 500-600 thousand cells of fungal materials per cm$^2$ on scarified skin of guinea pigs, thin necrotic scabs are formed. Spontaneous recovery after 25-30 days. |
| Reaction response | Result of intramuscular injection of inactivated corpuscular antigens from | Result of intramuscular injection of inactivated corpuscular |

TABLE C-continued

| Properties and characteristics of the strains | Strain No. DSM-9471 | Epidemic Strain No. 620 |
|---|---|---|
| | cultures: no observed changes in clinical state of animals | antigens from cultures: inflammation at point of injection, oedema |
| Immunogenic response | Results of immunisation of a group of guinea pigs with inactivated antigen from cultures (repeated not less than 5 times): establishes immunity | Results of immunisation of a group of guinea pigs with inactivated antigen from cultures (repeated not less than 5 times): establishes immunity |

*Trichophyton Rubrum*, No. DSM-9472

The strain was deposited at the DSM on May 10, 1994 under Serial No. DSM-9472. The strain was obtained by directed selection based on spore production and attenuation of the epizootic strain No. 754, which was identified on a nail of man in 1990. The strain was identified using the "Rebell-Taplin" key (Rebell, G., Taplin, D.: Dermatophytes, their recognition and identification, 3rd Print, University of Miami Press. Coral Gables, Fla., USA, 1978). The biological properties of the strain are described in Table D. Strain No. DSM-9472 differs from the epidemic strain in its faster growth in nutrient medium, an enormous production of microconidia and lower virulence.

TABLE D

| Properties and characteristics of the strains | Strain No. DSM-9472 | Epidemic Strain No. 754 |
|---|---|---|
| Description of the culture | Mature 15-day colony on agar Sabouraud: white, velvety, in centre folded, margin of colony regular, under surface yellow in centre purple, diameter of colony 35-40 mm | 20-day colony on agar Sabouraud: white-rose, downy, margin of colony regular, under surface purple, diameter of colony 20-25 mm |
| Morphological characteristics | Mature 15-day culture with septate branching hyphae 1-3 µm wide, round oval puriform microconidia measuring 2-3 × 3-7 µm. | 20-day culture with septate branching hyphae 1-3 µm wide, microconidia clavate to round in small open clusters and along the hyphae measuring 2-3 × 3-6 µm; macroconidia are rare, long and pencil-shaped with 3-5 cross walls measuring 4-7 × 15-50 µm. |
| Pathogenic characteristics | The strain is weakly virulent. 9-10 days after application of a dose of 500-600 thousand cells of fungal materials per cm² on scarified skin of guinea pigs, scales are formed. Spontaneous recovery after 18-20 days. | The strain is virulent. 9-10 days after application of a dose of 500-600 thousand cells of fungal materials per cm² on scarified skin of guinea pigs, thin necrotic scabs are formed. Spontaneous recovery after 25-30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of guinea pigs with | Results of immunisation of a group of guinea pigs with inactivated antigen |

TABLE D-continued

| Properties and characteristics of the strains | Strain No. DSM-9472 | Epidemic Strain No. 754 |
|---|---|---|
| | inactivated antigen from cultures (repeated not less than 5 times): establishes immunity | from cultures (repeated not less than 5 times): establishes immunity |

*Candida Albicans*, No. DSM-9456

The strain was deposited at the DSM on May 10, 1994 under Serial No. DSM-9456. The strain was obtained by directed selection based on stabilization of cultural-morphological characteristics and attenuation of epidemic strain No. 008-L, which was identified on man in 1990. The strain was identified using the Lodder's key (Lodder, J: The yeast: A Taxonomic Study. North-Holland Publ. Co., Amsterdam-London (1970). The biological properties of the strain are described in Table E. Strain No. DSM-9456 differs from the epidemic strain in its faster growth in nutrient medium, stabile biological properties, an enormous production of biomass and virulence.

TABLE E

| Properties and characteristics of the strains | Strain No. DSM-9456 | Epidemic Strain No. 008-L |
|---|---|---|
| Description of the culture | 10-day single-spore colony on agar Sabouraud: cream smooth and pasty glistening, elevated, margin of colony regular, diameter of colony 20-30 mm | 10-day single-spore colony on agar Sabouraud: cream soft and smooth with feathery offshots at the edges, diameter of colony 10-15 mm |
| Morphological characteristics | 10-day culture with spherical oval blastospores measuring 3.5-6 × 6-10 µm, chlamidospores 12-15 µm wide, pseudohyphae 5-8 µm, wide, hyphae 1.5-3 µm wide | 10-day single-spore culture on agar Sabouraud with spherical oval budding blastospores measuring 3-5 × 5-8 µm, chlamidospores 10-15 µm diameter, pseudohyphae 5-8 µm wide, hyphae 1,5-3 µm wide. |
| Pathogenic characteristics | The strain is weakly virulent. 30 days after intraperitoneal injection of a dose of 10-100 million fungal cells to white mice, granuloma in abdominal organs of 50% of animals are formed. Lethal effect was not observed. | The strain is weakly virulent. 30 days after intraperitoneal injection of a dose of 10-100 million fungal cells to white mice, granuloma in abdominal organs of 80-100% of animals are formed. Lethal effect in 50-70% was observed. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of white mice with inactivated antigen from cultures (repeated not less than 10 times): establishes immunity | Results of immunisation of a group of white mice with inactivated antigen from cultures (repeated not less than 10 times): establishes immunity |

*Candida Albicans*, No. DSM-9457

The strain was deposited at the DSM on May 10, 1994 under Serial No. DSM-9457. The strain was obtained by directed selection based on stabilization of cultural-morphological characteristics and attenuation of epidemic strain No.

012, which was identified on man in 1992. The strain was identified using the Lodder's key (Lodder, J: The yeast: A Taxonomic Study. North-Holland Publ. Co., Amsterdam-London (1970). The biological properties of the strain are described in Table F. Strain No. DSM-9457 differs from the epidemic strain in its faster growth in nutrient medium, stabile biological properties, an enormous production of biomass and lower virulence.

TABLE F

| Properties and characteristics of the strains | Strain No. DSM-9457 | Epidemic Strain No. 012 |
|---|---|---|
| Description of the culture | 10-day single-spore colony on agar Sabouraud: cream rough elevated, margin of colony lobulated, diameter of colony 20-23 mm | 10-day single-spore colony on agar Sabouraud: cream rough elevated, margin of colony fringed and lobulated, diameter of colony 15-20 mm |
| Morphological characteristics | 10-day single-spore culture with spherical oval blastospores measuring 3.5-5 × 5-10 μm, chlamidospores 12-15 μm wide, pseudohyphae 4-7 μm wide, hyphae 2-3 μm wide | 10-day single-spore culture on agar Sabouraud with spherical oval budding blastospores measuring 3-5 × 5-8 μm, chlamidospores 10-15 μm diameter, pseudohyphae 5-8 μm wide, hyphae-1.5-3 μm wide |
| Pathogenic characteristics | The strain is weakly virulent. 30 days after intraperitoneal injection of a dose of 10-100 million fungal cells to white mice, granuloma in abdominal organs in 30% of animals are formed. Lethal effect was not observed. | The strain is weakly virulent. 30 days after intraperitoneal injection by dose of 10-100 million fungal cells to white mice, granuloma in abdominal organs of 50% of animals are formed. Lethal effect not more 50% were observed. |
| Reaction response | Result of intramuscular injection of inactivated corpuscular antigens from cultures: no observed changes in clinical state of animals | Result of intramuscular injection of inactivated corpuscular antigens from cultures: no observed changes in clinical state of animals |
| Immunogenic response | Results of immunisation of a group of white mice with inactivated antigen from cultures (repeated not less than 10 times): establishes immunity | Results of immunisation of a group of white mice with inactivated antigen from cultures (repeated not less than 10 times): establishes immunity |

*Candida Albicans*, No. DSM-9458

The strain was deposited at the DSM on May 10, 1994 under Serial No. DSM-9458. The strain was obtained by directed selection based on stabilization of cultural-morphological characteristics and attenuation of epidemic strain No. 047, which was identified on man in 1989. The strain was identified using the Lodder's key (Lodder, J: The yeast: A Taxonomic Study. North-Holland Publ. Co., Amsterdam-London (1970). The biological properties of the strain are described in Table G. Strain No. DSM-9458 differs from the epidemic strain in its faster growth in nutrient medium, stabile biological properties, an enormous production of biomass and lower virulence.

TABLE G

| Properties and characteristics of the strains | Strain No. DSM-9458 | Epidemic Strain No. 047 |
|---|---|---|
| Description of the culture | 10-day single-spore colony on agar Sabouraud: cream smooth and pasty glistening, elevated, margin of colony regular, diameter of colony 16-18 mm | 10-day single-spore colony on agar Sabouraud: cream soft and smooth with feathery offshots at the edges, diameter of colony 10-15 mm |
| Morphological characteristics | 10-day culture with spherical oval blastospores measuring 3.6-6 × 6-11 μm, chlamidospores 12-15 μm wide, pseudohyphae 4-8 μm wide, hyphae 1.5-3 μm wide | 10-day single-spore culture on agar Sabouraud with spherical oval budding blastospores measuring 3-5 × 5-8 μm, chlamidospores 10-15 μm diameter, pseudohyphae 5-8 μm wide, hyphae 1.5-3 μm wide. |
| Pathogenic characteristics | The strain is weakly virulent. 30 days after intraperitoneal injection of a dose of 10-100 million fungal cells to white mice, granuloma in abdominal organs of 50-100% of animals are formed. Lethal effect in 50% were observed. | The strain is weakly virulent. 30 days after intraperitoneal injection by dose of 10-100 million fungal cells to white mice, granuloma in abdominal organs of 80-100% of animals are formed. Lethal effect in 70-100% were observed. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of white mice with inactivated antigen from cultures (repeated not less than 10 times): establishes immunity | Results of immunisation of a group of white mice with inactivated antigen from cultures (repeated not less than 10 times): establishes immunity |

*Candida Albicans*, No. DSM-9459

The strain was deposited at the DSM on May 10, 1994 under Serial No. DSM-9459. The strain was obtained by directed selection based on stabilization of cultural-morphological characteristics and attenuation of epidemic strain No. 158, which was identified on man in 1990. The strain was identified using the Lodder's key (Lodder, J: The yeast: A Taxonomic Study. North-Holland Publ. Co., Amsterdam-London (1970). The biological properties of the strain are described in Table H. Strain No. DSM-9459 differs from the epidemic strain in its faster growth in nutrient medium, stabile biological properties, an enormous production of biomass and lower virulence.

TABLE H

| Properties and characteristics of the strains | Strain No. DSM-9459 | Epidemic Strain No. 158 |
|---|---|---|
| Description of the culture | 10-day single-spore colony on agar Sabouraud: cream smooth pasty glistening, elevated, margin of colony regular, diameter of colony 16-18 mm | 10-day single-spore colony on agar Sabouraud: cream smooth pasty, margin of colony lobulated and with feathery offshots at the edges, diameter of colony 10-15 mm |

TABLE H-continued

| Properties and characteristics of the strains | Strain No. DSM-9459 | Epidemic Strain No. 158 |
|---|---|---|
| Morphological characteristics | 10-day culture with spherical oval blastospores measuring 3.6-6 × 6-11 µm, chlamidospores 12-15 µm wide, pseudohyphae 4-8 µm wide, hyphae 1.5-3 µm wide | 10-day single-spore culture on agar Sabouraud with spherical oval budding blastospores measuring 3-5 × 5-8 µm, chlamidospores 10-15 µm diameter, pseudohyphae 5-8 µm wide, hyphae 1.5-3 µm wide. |
| Pathogenic characteristics | The strain is weakly virulent. 30 days after intraperitoneal injection by dose of 10-100 million fungal cells to white mice, granuloma in abdominal organs of 40% of animals are formed. Lethal effect was not observed. | The strain is weakly virulent. 30 days after intraperitoneal injection by dose of 10-100 million fungal cells to white mice, granuloma in abdominal organs of 50% of animals are formed. Lethal effect in 20-50% was observed. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of white mice with inactivated antigen from cultures (repeated not less than 10 times): establishes immunity | Results of immunisation of a group of white mice with inactivated antigen from cultures (repeated not less than 10 times): establishes immunity |

TABLE I

| Properties and characteristics of strain | Strain No. VKPGF-930/1032 | Epizootic Strain No. 1032 |
|---|---|---|
| Description of culture | Mature 10-15 day colony in agar/wort; cream, velvety/powdered, flat with slight flat elevation in center, narrow growing margin, fringed, undersurface light brown, colony diameter 25-30 mm | Mature 25-30 day colony in agar/wort; white, flat, narrow, growing margin, undersurface reddish-brown, colony diameter 15-20 mm |
| Morphological characteristics | Septate, branching hyphae 1-3 µm wide, numerous pyriform, oval microconidia measuring 1 to 3 × 2 to 6 µm, no macroconidia | Septate, branching straight and spiral hyphae 1-3 µm wide, round, flattened pyriform microconidia measuring 1 to 3 × 2 to 6 µm, few elongate-oval macroconidia with 2-5 septates, measuring 2 to 6 × 15 to 25 µm |
| Pathogenic characteristics 9 to 10 days after application of a dose of 500-600 thousand cells of fungal matter per cm² to the scarified skin of a rabbit | Necrotic scabs | Dense, asbestos-like scabs |
| Spontaneous recovery after | 22-25 days | 30-35 days |
| Reaction response Results of subcutaneous and intramuscular injection of inactivated corpuscular antigens from cultures | No observed changes in clinical state | Inflammation at point of injection, edema |
| Antigen response 20 to 25 days after injecting rabbits with corpuscular antigens, antibody titers observed in blood serum | | |
| By PHR | 1:320 to 1:640 | 1:320 to 1:640 |
| By ELISA | 1:400 to 1:1600 | 1:400 to 1:1600 |
| Immunogenic response Immunization of a group of rabbits with inactivated antigens from cultures (repeated at least 5 times) | Establishes immunity | Establishes immunity |

*Trichophyton Mentagrophytes* No. VKPGF-930/1032, No. DSM-7279

Strain *Trichophyton mentagrophytes* DSM-7279 has been deposited according to the Budapest Treaty at the "Deutsche Sammlung von Mikroorganismen und Zellkulturen" (DSM), Mascheroder Weg 1B, W-38124 Braunschweig, Germany (which current name and address is "Leibniz-Institut DSMZ-Deutsche Sammlung von Mikroorganismen und Zellkulturen GmbH" (DMSZ), Inhoffenstraße 7B, 38124 Braunschweig, GERMANY) on 1 Oct. 1992 by Boehringer Ingelheim Vetmedica GmbH, 6507 Ingelheim am Rhein (which current address is Boehringer Ingelheim Vetmedica GmbH, 55216 Ingelheim am Rhein). The current depositors of said strain are the applicants, namely Dr. Igor Polyakov and Dr.sc.Dr. Liudmila Ivanova, Eberhardtstr. 40, 89073 Ulm.

*Trichophyton verrucosum*, No. DSM-28406

The strain *Trichophyton verrucosum* BINO 348 was deposited by the Binomed GmbH (Einsteinstraße 59, 89077 Ulm) according to the Budapest Treaty at the—Leibniz-Institut DSMZ—Deutsche Sammlung von Microorganismen und Zellkulturen GmbH, Inhoffenstraße 7B, 38124 Braunschweig, Germany under Serial No. DSM-28406 on 12 Feb. 2014. The depositor has authorized the applicants to refer to the deposited biological material in the application and has given his unreserved and irrevocable consent to the deposited material being made available to the public in accordance with Rule 31 EPC. The strain was obtained by directed selection based on spore production and attenuation of epizootic strain Nr. 348, which was isolated from cattle in 1997. The strain was identified using the Rebell-Taplin key (Rebell, G., Taplin, D.: Dermatophytes, their recognition and identification, 1978) and according to Kashkin, P. N. et. al. (opredelitel patogennykh, toksigenykh vrednykh dlya cheloveka gribov, 1979). The biological properties of the strain are described in Table J. Strain BINO 348-DSM 28406 differs from the epizootic strain in its faster growth in nutrient medium, the enormous production of microconidia, lower virulence and the absence of any adverse reactions after intramuscular application of antigens.

TABLE J

| Properties and characteristics of the strains | Strain No. DSM-28406 | Epidemic Strain No. 348 |
|---|---|---|
| Description of the culture | 20-day colony on Malt Extract Agar: white or light-yellow, velvety, furrowed, diameter of colony 15-20 mm | 25-30-day colony in Malt Extract Agar: light-yellow cream, velvety, folded, undersurface colorless, diameter of colony 10-12 mm |
| Morphological characteristics | Mature 20-day culture with numerous oval, pyriform microconidia measuring 1,5-3 × 3-5 μm. | Mature 25-30 day culture with septate branching mycelium, few oval, pyriform microconidia 1 to 3 μm × 3 to 6 μm, macroconidia with 2 to 6 septates, few arthrospores and chlamydospores 9-11 μm. |
| Pathogenic characteristics | The strain is weakly virulent. 9-10 days after application of a dose of 500-600 thousand cells of fungal material per $cm^2$ on scarified skin of guinea pigs, scales are formed. Spontaneous recovery after 15-20 days. | The strain is virulent. 9-10 days after application of a dose of 500-600 thousand cells of fungal material per $cm^2$ on scarified skin of pigs, thin necrotic scabs are formed. Spontaneous recovery after 25-30 days. |
| Reaction response | Result of intramuscular injection of inactivated corpuscular antigens from cultures: no observed changes in clinical state of animals | Result of intramuscular injection of inactivated corpuscular antigens from cultures: inflammation at point of injection, oedema |
| Immunogenic response | Results of immunisation of a group of guinea pigs with inactivated antigen from cultures (repeated not less than 5 times): establishes immunity against dermatophytos cause by T.verrucosum | Results of immunisation of a group of guinea pigs with inactivated antigen from cultures (repeated not less than 5 times): establishes immunity against dermatophytos cause by T.verrucosum |

Chrisporium *Tropicum*, No. DSM-28405

The strain Chrisporium *tropicum* BINO 122 was deposited by the Binomed GmbH (Einsteinstraße 59, 89077 Ulm) according to the Budapest Treaty at the—Leibniz-Institut DSMZ— Deutsche Sammlung von Microorganismen and Zellkulturen GmbH, Inhoffenstraße 7B, 38124 Braunschweig, Germany under Serial No. DSM-28405 on 12 Feb. 2014. The depositor has authorized the applicants to refer to the deposited biological material in the application and has given his unreserved and irrevocable consent to the deposited material being made available to the public in accordance with Rule 31 EPC. The strain was obtained by directed selection based on spore production of field strain Nr. 122, which was isolated from the soil in 1993. The strain was identified using the Rebell-Taplin key (Rebell, G., Taplin, D.: Dermatophytes, their recognition and identification, 1978) and according to Carmichael, J. N. *Chrysosporium* and some other aleuriosporic hyphomycetes.—Can. J. Bot., 1962, 40, 1137-1173. The biological properties of the strain are described in Table K. Strain BINO 122-DSM 28405 is differ from the field strain in its faster growth in nutrient medium, the enormous production of conidia, weak virulence and the production of enzymes.

TABLE K

| Properties and characteristics of the strains | Strain No. DSM-28405 | Field Strain No. 122 |
|---|---|---|
| Description of the culture | 15-day colony on Malt Extract Agar is white, felty, powdery, diameter of colony 60-70 mm. Good growth at 26 C° as well as 37 C°. | 15-day colony on Malt Extract Agar is white, felty, powdery, diameter of colony 55-65 mm. Good growth at 26 C° and 37 C°. |
| Morphological characteristics | Mature 15-day culture with numerous terminal and lateral conidia sessile or on short protrusions or side branches, smooth-walled, clavate or obovoidal, 3-6 × 6-9 μm. | Mature 15-day culture with terminal and lateral conidia sessile or on short protrusions or side branches, smooth-walled, clavate or obovoidal, 3-6 × 6-9 μm. |
| Pathogenic characteristics | The strain is weakly virulent. 9-10 days after application of a dose of 500-600 thousand cells of fungal material per $cm^2$ on scarified skin of guinea pigs, hyperemia and scales are formed. Spontaneous recovery after 13-15 days. | The strain is weakly virulent. 9-10 days after application of a dose of 500-600 thousand cells of fungal material per $cm^2$ on scarified skin of guinea pigs, hyperemia and scales are formed. Spontaneous recovery after 13-15 days. |
| Reaction response | Result of cutaneous application of filtrate of culture: quick epithelium regeneration | Result of cutaneous application of filtrate of culture: filtrate of culture: epithelium regeneration |
| Biological properties | enzymatic activity; immunogenic activity against dermatophytosis; immunocorrection in allergy; increased regeneration of the skin | enzymatic activity; immunogenic activity against dermatophytosis; immunocorrection in allergy; regeneration of the skin |

*Microsporum canis* BINO 483

The strain *Microsporum canis* BINO 483 was deposited by the Binomed GmbH (Einsteinstraße 59, 89077 Ulm) according to the Budapest Treaty at the—Leibniz-Institut DSMZ—Deutsche Sammlung von Microorganismen and Zellkulturen GmbH, Inhoffenstraße 7B, 38124 Braunschweig, Germany under under Serial No. DSM-32271 on 25 Feb. 2016. The depositor has authorized the applicants to refer to the deposited biological material in the application and has given his unreserved and irrevocable consent to the deposited material being made available to the public in accordance with Rule 31 EPC. The strain was obtained by directed selection based on spore production and attenuation of epizootic strain Nr. 483, which was isolated from cat in 1990. The strain was identified using the Rebell-Taplin key (Rebell, G., Taplin, D.: Dermatophytes, their recognition and identification, 1978) and according to Kashkin, P. N. et, al. (opredelitel patogennykh, toksigenykh vrednykh dlya cheloveka gribov, 1979). The biological properties of the strain are described in Table L. vaccine strain 483 differs from the epizootic strain in its faster growth in nutrient medium, the enormous production of microconidia, lower virulence and the absence of any adverse reactions after intramuscular application of antigens.

TABLE L

| Properties and characteristics of the strains | Vaccine Strain No. BINO 483 | Epidemic Strain No. 483 |
|---|---|---|
| Description of the | 10-15-day colony on Malt Extract | 15-day colony in Malt Extract Agar: |

TABLE L-continued

| Properties and characteristics of the strains | Vaccine Strain No. BINO 483 | Epidemic Strain No. 483 |
|---|---|---|
| culture | Agar: white, fluffy, convex, narrow growing margin, arachnoid, undersurface yellowish, diameter of colony 35-40 mm | greyish-beige, arachnoid, powdery in centre, growing margin fringed, undersurface brown, diameter of colony 25-30 mm |
| Morphological characteristics | Mature 15-day culture with septate branching hyphae 1 to 4 μm wide, numerous oval, pyriform, cylindrical microconidia measuring 1 μm to 3 μm × 3 μm to 7 μm, few fusiform macroconidia with 3 to 10 septates measuring 10 μm to 20 μm × 40 μm to 70 μm | Mature 15-day culture with branching hyphae 2 to 6 μm wide, few pyriform, cylindrical microconidia measuring 1 μm to 3 μm × 3μm to 7 μm, numerous fusiform macroconidia with 3 to 11 septates measuring 10 μm to 20 μm × 45 μm to 85 μm |
| Pathogenic characteristics | The strain is weakly virulent. 9-11 days after application of a dose of 500-600 thousand cells of fungal material per cm² on scarified skin of a rabbit: necrotic scabs are formed. Spontaneous recovery after 15-25 days. | The strain is virulent. 9-11 days after application of a dose of 500-600 thousand cells of fungal material per cm² on scarified skin of a rabbit: dense asbestos-like scabs are formed. Spontaneous recovery after 25-38 days. |
| Reaction response | Result of intramuscular injection of inactivated corpuscula antigens from cultures: no observed changes in clinical state of animals | Result of intramuscular injection of inactivated corpuscular antigens from cultures: oedema and inflammation at point of injection, |
| Immunogenic response | Results of immunisation of a group of rabbits (5 animals in group) with life or inactivated antigen from cultures: establishes immunity against dermatophytos cause by *Microsporum canis* | Results of immunisation of a group of rabbits (5 animals in group) with life or inactivated antigen from cultures: establishes immunity against dermatophytos cause by *Microsporum canis* |

In a preferred embodiment the composition of the present invention comprises homogenised inactivated dermatophyte microconidia of one microconidia or a mixture of microconidia of two, three, four, five, six, seven, eight, nine or ten of the above listed strains of dermatophytes. In a further preferred embodiment the composition comprises a mixture of homogenised inactivated dermatophyte microconidia of one, two, three, four, five, six, seven, eight, nine or ten of the above listed dermatophytes and homogenised inactivated yeast blastospores of one, two, three, or four of the above listed yeasts. In a further preferred embodiment the composition comprises homogenised inactivated dermatophyte microconidia of one or a mixture of two, three, or four of the above listed yeasts. The compositions may additionally comprise antigenic material of dermatophyte microconidia and/or antigenic material of yeast blastospores.

In a further preferred embodiment the composition comprises antigenic material of one dermatophyte microconidia or a mixture of antigenic material of dermatophyte microconidia of two, three, four, five, six, seven, eight, nine or ten of the above listed strains of dermatophyte. In a further preferred embodiment the composition comprises a mixture of antigenic material of dermatophyte microconidia of one, two, three, four, five, six, seven, eight, nine or ten of the above listed dermatophytes and antigenic material of yeast blastospores of one, two, three, or four of the above listed yeasts. In a further preferred embodiment the composition comprises antigenic material of yeast blastospores of one or a mixture of two, three, or four of the above listed yeasts. The compositions may additionally comprise homogenised inactivated dermatophyte microconidia of one, two, three, four, five, six, seven, eight, nine or ten of the above listed dermatophytes and/or homogenised inactivated yeast blastospores of one, two, three, or four of the above listed yeasts.

In a preferred embodiment the composition for use of the present invention comprises a mixture of homogenised inactivated dermatophyte microconidia of *Trichophyton mentagrophytes*, *Trichophyton verrucosum*, *Trichophyton equinum*, *Trichophyton sarkisovii*, *Microsporum canis*, *Microsporum canis* var. *obesum*, *Microsporum canis* var. *distortum* and *Microsporum gypseum*. For example, the vaccine Polivac-TM (manufacturer: "Vethiochim" LLC, Moscow; Distributor: "Prostore" LLC, Moscow) is in accordance with this embodiment and can be comprised in a composition of the present invention. Polivac-TM is a vaccine designed for animals such as cats, dogs, horses and others.

In a further preferred embodiment the composition of the present invention comprises a mixture of homogenised inactivated dermatophyte microconidia of *Trichophyton mentagrophytes*, *Trichophyton verrucosum* and *Trichophyton sarkisovii*. For example, the vaccine Polivac-T (manufacturer: "Vetbiochim" LLC, Moscow; Distributor: "Prostore" LLC, Moscow) is in accordance with this embodiment and can be comprised in the composition of the present invention. Polivac-T is a vaccine specifically designed for cattle.

If the composition of the present invention comprises dermatophyte microconidia of only one strain or yeast blastospores of only one strain said dermatophyte microconidia or yeast blastospores can be prepared as follows:

(i) growing a dermatophyte and a yeast, respectively, on suitable solid medium, harvesting and homogenising the dermatophyte, and (ii) inactivating the homogenate obtained in step (i)

If the composition of the present invention comprises a mixture of dermatophyte microconidia and/or yeast blastospores said mixture can be prepared as follows:

(i) growing one dermatophyte strain and two, three, four, five, six, seven, eight, nine or ten distinct strains of dermatophytes, respectively, separately on suitable solid medium, harvesting each culture and homogenising each culture separately, and (ii) optionally, growing one yeast strain and two, three or four distinct strains of yeast, respectively, separately on suitable solid medium, harvesting each culture and homogenising each culture separately, and (iii) combining and inactivating the homogenates obtained in step (i) and optionally obtained in step (ii).

The growing of the dermatophytes of the above described preparation processes is preferably done on agar and worth in culture flasks. Preferably, the culture is performed for about 15 to about 30 days. Preferably, the cultivation is performed at a temperature of about 26° C. to about 28° C. The growing of the yeasts of the above described preparation processes is preferably done on malt extract-agar or agar Sabouraud in culture flasks. Preferably, the culture is performed for about 4 to about 7 days. Preferably, the cultivation is performed at a temperature of about 28 to about 37° C.

After cultivation the dermatophytes and yeasts, respectively, are homogenized to obtain a fine suspension. Preferably the homogenization is performed in deionized water, in an aqueous solution comprising about 0.1 to 0.3% fermented hydrolysed muscle protein or about 0.1 to 1% soy or pork peptone in combination with about 5 to 6% glucose and about 0.1 to 1% yeast extract, or in an aqueous solution comprising 0.1-0.9% (w/v) modified chitosan according to the present invention.

Suitable volumes for homogenization are about 100 to 500 ml. Preferably, the concentration of microconidia and blastospores, respectively, is adjusted to about 30 to about 90 million microconidia and blastospores, respectively, per ml or to about 250 to about 500 thousand, more preferably about 250 to about 400 thousand microconidia and blastospores, respectively, per ml. Then, the suspension may optionally be additional adjusted to about 40, 50 or 60 million of microconidia and blastopores, respectively, per ml or to about 250 to about 500 thousand, more preferably to about 250 to about 400 thousand microconidia and blastospores, respectively, per ml with distilled water, physiological salt solution as e.g. sodium chloride or another suitable solution. In case of the preparation of a mixture, the single suspensions are preferably adjusted to the same amount of microconidia and blastospores, respectively, per ml and equal volumes of each culture in suspension are mixed in a single container.

The inactivation is preferably performed by using thiomersal, formaldehyde and/or 2-propiolactone. The agents for inactivating can be added directly to the cell suspension. Preferred is an inactivation by adding thiomersal in a ratio of about 1:11000 to about 1:2500 (w/v). Also preferred is an inactivation by adding formaldehyde to reach an end concentration of about 0.2% to about 0.4% (v/v). Subsequently, the mixture is preferably incubated. The incubation can be performed for about 1 to 30 days at a temperature of about 20° C. to about 37° C. Preferred is incubation for about 1 to 3 days at room temperature, for about 5 to 7 days at 37° C., for about 30 days at room temperature or for about 30 days at about 26° C. to 28° C.

In a preferred embodiment the microconidia of the compositions of the present invention are in a swollen condition and/or have germ tubes. More preferably, at least 50% of the blastospores and/or microconidia are in a swollen condition and/or have germ tubes. The swollen condition and/or the germ tubes of dermatophytes can e.g. be obtained by a second incubation step. Said second incubation step is preferably performed after the homogenization and before inactivation as described above. For performing the second cultivation step the microconidia suspension is placed in a separate vessel containing the same medium of the first incubation step. The second cultivation step is preferably performed for about 10 to about 48 hours. The second cultivation step is preferably performed at a temperature of about 28° C. Preferably, the second cultivation step is continued until at least 50% of the microconidia display a swollen or germinating condition and no more than about 7 to 10% of the cells display a second mycelial branch. The diameter of swollen and germinated microconidia is increased by about 1.2 or more compared to regular microconidia.

The antigenic material of yeast blastospores and/or dermatophyte microconidia preferably comprises polysaccharides and/or glycopeptides isolated from keratinophilic fungi or yeasts. Preferably, said antigenic material can be antigenic nonsoluble material (ANMP), antigenic soluble material (ASMP) or antigenic exogenous material (AEMP). The keratinophilic fungi are preferably of the species *Trichophyton* or *Microsporum*, more preferably *Trichophyton verrucosum, Trichophyton mentagrophytes, Trichophyton equinum, Trichophyton sarkisovii, Trichophyton rubrum, Trichophyton mentagrophytes, Microsporum gypseum, Microsporum canis* and Chrisporium *tropicum*, and the keratinophilic yeasts are preferably of the species *Candida*, more preferably *Candida albicans*. Especially preferred is antigenic material derived from *Trichophyton mentagrophytes* DSM-7279, *Trichophyton verrucosum* DSM-28406, *Trichophyton rubrum* DSM-9469, *Trichophyton rubrum* DSM-9470, *Trichophyton rubrum* DSM-9471, *Trichophyton rubrum* DSM-9472, Chrisporium *tropicum* DSM-28405, *Candida albicans* DSM-9456, *Candida albicans* DSM-9457, *Candida albicans* DSM-9458, and *Candida albicans* DSM-9459. The antigenic material is, for example, obtainable by the method disclosed in WO 97/07232.

In general for obtaining ANMP, the fungal cells belonging to the group of keratinophilic fungi or yeasts are treated under aqueous alkaline conditions, the solid and liquid phases of the preparation are separated, and after separation the solid phase is treated with mineral or organic acid. The treatment under aqueous alkaline conditions is preferably performed with about 0.1 to 5% (w/v) KOH or NaOH at about 20° C. to 150° C. for up to 30 h. The solid phase is preferably treated with 0.2 to 1.5 M organic acid or 0.05 to 1 M mineral acid and washed with an aqueous solution. More specifically, the keratinophilic fungi or yeasts are preferably cultivated on Agar plates. One preferred medium is for example malt extract agar from Oxoid. Other media that will ensure growth of keratinophilic fungi or yeast may be used as well. The resulting fungal biomass was lifted off and treated with the aqueous solution of alkali. Subsequently, the solid and liquid phases of the preparation are separated, for example by centrifugation, filtration or sedimentation. Preferably, the separation is performed by centrifugation, e.g. at 3500 g, which allows good separation of the fungal cell debris. Both the treatment under aqueous alkaline conditions and the separation step may be repeated several times. After alkaline treatment, the resulting supernatant is treated under the acidic aqueous conditions as outlined above. For example, HCl or acetic acid can be used. The treatment with acid is preferably performed for about 0.5 to about 3 hours. The temperature is preferably in the range of about 70 to about 100° C. The aqueous solution for washing is preferably distilled water. Advantageously, the washing is repeated about five times. Finally, the solid phase is lifted off and homogenized in water for injection or in an aqueous solution of 0.1-0.9% solution of the modified chitosan, chitosan variant or chitosan derivative according to the present invention. The homogenization is preferably performed in a volume of about 100 to about 500 ml. The concentration of particles is then preferably adjusted to about 30 to 90 million particles per ml. Finally, the preparation comprising the antigenic material can be lyophilised and stored under dry conditions.

ASMP can generally be obtained as follows: Fungal cells of keratinophilic fungi or yeasts are treated under aqueous alkaline conditions, the solid and liquid phases of the preparation are separated, after separation the supernatant is treated with mineral or organic acid, and after separation ASMP is precipitated from the supernatant. More particularly, keratinophilic fungi or yeasts are cultivated on Agar plates, for example as described in EP 0564620. One preferred medium is for example malt extract agar from Oxoid. Other media that will ensure growth of keratinophilic fungi or yeast may be used as well. The resulting fungal biomass was lifted off and treated with an aqueous solution of alkali. Preferred aqueous alkaline solutions are NaOH or KOH at preferred concentrations of 0.1-5% (w/v). Alkaline treatment is preferably performed at about 20-150° C. for up to 30 h. Following the processing under aqueous alkaline conditions, the solid and liquid phases of the preparation are separated, for example, by centrifugation, filtration or sedimentation. Preferably, the separation is achieved by centrifugation, which ensures good separation of the fungal cell debris, for example, at forces of about 3500 g. The treatment under aqueous alkaline conditions, as well as the separation step, may be repeated several times. After the alkaline treatment and separation, the resulting supernatant is treated under acidic aqueous conditions, e.g. 0.2-1.5 M organic acid or 0.05-1 M mineral acid. For example, HCl or acetic acid can be used, preferably at pH values of about pH 2.5 to pH 4.5. Preferably, the treatment under aqueous acidic conditions is for about 2 to 4 hours at temperatures of about 4 to 8° C., where after separation of the solid and liquid layers took place. The treatment under aqueous acidic conditions, as well as the separation step, may be repeated several times, preferably under conditions as above indicated. Then, the supernatant from the separation step was subjected to a precipitation step. Preferably, the precipitation was performed by adding a suitable organic solvent, e.g. an alcohol such as a lower alkanol, for example methanol or ethanol. A ratio of one volume supernatant to 2-5 volumes of alcohol will result in a good precipitation of the antigenic material. Other nonalcoholic precipitation procedures known to the person skilled in the art may be used as well, for example, ammonium sulphate or other salt precipitation. The solid phase is then subject to a further separation step, preferably under conditions as described above. The resulting solid phase is recovered and, if desired, dissolved in an aqueous solution, preferably in distilled water, typically in a volume of about 25 to 100 ml. Finally, the ASMP preparation can be lyophilized and stored for prolonged time periods under dry conditions.

AEMP can generally be obtained as follows: fungal cells of keratinophilic fungi or yeasts are cultivated in liquid medium, the solid phase and liquid phases of the preparation are separated, and after separation AEMP is precipitated from the supernatant. More particularly, keratinophilic fungi or yeasts may be incubated in aqueous solution or cultivated in liquid medium. As well as the keratinophilic fungi may be incubated in aqueous solution with keratin. The cultivation may be for up to about 240 to 250 hours. The volume of the solution or culture is here defined as primary volume (PV). Distilled water can be used as well as media described in EP 0564620. After incubation or cultivation, the fungal cells are separated, for example, by centrifugation, filtration or sedimentation, preferably by centrifugation under conditions as described above. Optionally, the resulting supernatant is then lyophilized and subsequently dissolved in aqueous solution, preferably in water. Preferably, the volume of water is about 0.1 to 0.2 volumes of the primary volume (PV). The resulting solution or the resulting supernatant obtained after separation is then subject to a precipitation step. Preferably, the precipitation was performed by adding a suitable organic solvent, e.g. an alcohol such as a lower alkanol, for example methanol or ethanol. A ratio of one volume supernatant to about 1 to 5 volumes of alcohol will result in a good precipitation of the antigenic material. Other nonalcoholic precipitation procedures known to the person skilled in the art may be used as well, for example ammonium sulphate or other salt precipitation. The resulting precipitate is recovered and, if desired, dissolved in an aqueous solvent, preferably in distilled water. Preferably, about 0.5 to 50 mg of the precipitate are dissolved in 1 ml aqueous solvent. Finally, the AEMP solution can be lyophilized and stored for prolonged time periods under dry conditions, preferably at about 2 to 10° C.

In a particularly preferred embodiment the composition of the present invention comprises in addition to the modified chitosan or the hydro colloid of the present invention inactivated dermatophyte microconidia of *Trichophyton mentagrophytes*, in particular of *Trichophyton mentagrophytes* DSM-7279.

In a further particularly preferred embodiment the composition of the present invention comprises in addition to the modified chitosan or the hydro colloid of the present invention inactivated dermatophyte microconidia of *Trichophyton verrucosum*, in particular of *Trichophyton verrucosum* DSM-28406.

In a further particularly preferred embodiment the composition of the present invention comprises in addition to the modified chitosan or the hydro colloid of the present invention inactivated yeast blastospores of *Candida albicans*, in particular of *Candida albicans* DSM-9456.

In a further particularly preferred embodiment the composition of the present invention comprises in addition to the modified chitosan or the hydro colloid of the present invention ASMP of *Candida albicans*, in particular of *Candida albicans* DSM-9456.

In a further particularly preferred embodiment the composition of the present invention comprises in addition to the modified chitosan or the hydro colloid of the present invention ANMP of *Candida albicans*, in particular of *Candida albicans* DSM-9456.

In a further particularly preferred embodiment the composition of the present invention comprises in addition to the modified chitosan or the hydro colloid of the present invention a mixture of homogenised inactivated dermatophyte microconidia of *Trichophyton mentagrophytes, Trichophyton verrucosum, Trichophyton equinum, Trichophyton sarkisovii, Microsporum canis, Microsporum canis* var. *obesum, Microsporum canis* var. *distortum* and *Microsporum gypseum* and optionally ASMP of *Candida albicans*, in particular of *Candida albicans* DSM-9456. More preferably, the composition of the present invention comprises the vaccine Polivac-TM and optionally ASMP of *Candida albicans*, in particular of *Candida albicans* DSM-9456.

In a further particularly preferred embodiment the composition of the present invention comprises in addition to the modified chitosan or the hydro colloid of the present invention AEMP of Chrisporium *tropicum*, in particular of Chrisporium *tropicum* DSM-28405, or of *Microsporum canis* BINO 483.

The concentration of inactivated dermatophyte microconidia and/or yeast blastospores in the composition of the present invention is preferably about 30 to about 90, more preferably about 45 to about 80 million microconidia and blastospores, respectively, per ml or about 250 to about 500 thousand, more preferably about 250 to about 300 thousand microconidia and blastospores, respectively, per ml. The concentration of ASMP in the composition of the present invention is preferably about 50 to about 500 µg/ml, more preferably about 100 to about 400 µg/ml. The concentration of ANMP in the composition of the present invention is preferably about 30 to about 90, more preferably about 40 to about 80 million per ml. The concentration of Polivac-TM in the composition of the present invention is preferably about 40 million per ml to about 50 million per ml, more preferably about 40 million per ml to about 45 million per ml. The concentration of AEMP in the composition of the present invention is preferably 0.5 to about 2 U/ml, more preferably about 1 to about 1.2 U/ml.

The composition of the present invention is preferably a pharmaceutical composition which comprises a pharmaceutical acceptable diluent, excipient and/or carrier. Thus, the present invention also refers to a pharmaceutical composition comprising a modified chitosan or the hydro colloid according to the present invention and a pharmaceutical acceptable diluent, excipient and/or carrier.

The concentration of the modified chitosan or the hydro colloid in the compositions or pharmaceutical compositions of the present invention is preferably about 0.1% to about 2.0% (w/v), more preferably about 0.1% to about 1.4% (w/v), more preferably about 0.1% to about 1% (w/v), more preferably about 0.1% to about 0.5% (w/v) more preferably about 0.1% to about 0.3% (w/v).

Another aspect of the present invention is the compound, the modified chitosan, the hydro colloid and/or the composition of the present invention for use in human and/or veterinary medicine. Preferably, the compound, the modified chitosan, the hydro colloid or the composition of the present invention is for use as a vaccine in human and/or veterinary medicine.

The present invention also refers to the compound, the modified chitosan, the hydro colloid and/or the composition of the present invention for use in a method of treating and/or preventing mastitis, preferably latent mastitis and/or acute mastitis, endometritis, preferably chronic, acute and/or purulent-catarrhal endometritis, hoof- and claw diseases, lameness, lesions in the interdigital space, digital dermatitis, interdigital dermatitis, interdigital phlegmon, trichophytosis, microsporosis, mycosis of skin, allergies, as well as diseases complicated by allergies, in particular allergic obstructive pulmonary disease, allergic skin diseases, allergic ear erythema, allergic rhinitis, allergic conjunctivitis, acute allergic contact dermatitis, chronic allergic contact eczema or atopic eczema, obstructive pulmonary disease, in particular chronic obstructive pulmonary disease, skin diseases, in particular dermatitis, ear erythema, rhinitis, conjunctivitis, dermatophytosis or warts, in particular Common warts, in a subject.

The present invention also refers to the compound, the modified chitosan, the hydro colloid and/or the composition of the present invention for use in a method of modulating the immune response in a subject and/or for enhancing reproduction efficiency, preferably reproduction efficiency in animal breeding.

The subject may for example be a human or an animal, in particular a mammal, more preferably bovidae and/or pigs, most preferably cattle, but also dogs, cats or other farm or domestic animals.

In a particularly preferred embodiment the invention refers to a composition comprising the modified chitosan, the hydro colloid or compound according to the present invention and inactivated dermatophyte microconidia of *Trichophyton mentagrophytes*, in particular of *Trichophyton mentagrophytes* DSM-7279, for use in a method of treating and/or preventing interdigital dermatitis, digital dermatitis and/or interdigital phlegmon in animals, in particular in bovidae and/or pigs, most preferably in cattle.

In a further particularly preferred embodiment the invention refers to a composition comprising the modified chitosan or the hydro colloid or compound according to the present invention and inactivated dermatophyte microconidia of *Trichophyton verrucosum*, in particular of *Trichophyton verrucosum* DSM-28406, for use in a method of treating and/or preventing interdigital dermatitis, digital dermatitis, interdigital phlegmon, and/or trichophytosis in animals, in particular in bovidae and/or pigs, most preferably in cattle.

In a further particularly preferred embodiment the invention refers to a composition comprising the modified chitosan or the hydro colloid or compound according to the present invention and inactivated yeast blastospores of *Candida albicans*, in particular of *Candida albicans* DSM-9456, for use in a method of treating and/or preventing interdigital dermatitis, digital dermatitis and/or interdigital phlegmon, in particular in bovidae and/or pigs, most preferably in cattle.

In a further particularly preferred embodiment the invention refers to a composition comprising the modified chitosan or the hydro colloid or compound according to the present invention and ASMP of *Candida albicans*, in particular of *Candida albicans* DSM-9456, for use in a method of treating and/or preventing allergies, in particular allergic obstructive pulmonary disease, allergic skin diseases, allergic ear erythema, allergic rhinitis, allergic conjunctivitis, acute allergic contact dermatitis, chronic allergic contact eczema or atopic eczema, obstructive pulmonary disease, in particular chronic obstructive pulmonary disease, skin diseases, ear erythema, rhinitis, conjunctivitis, dermatophytosis or warts, in particular Common warts, obstructive pulmonary disease, in particular chronic obstructive pulmonary disease, skin diseases, in particular dermatitis, ear erythema, rhinitis or conjunctivitis in humans and/or animals, in particular a mammals, more preferably in companion animals, most preferably dogs, cats and/or horses, but also cattle, pigs or other farm or domestic animals.

In a further particularly preferred embodiment the invention refers to a composition comprising the modified chitosan or the hydro colloid or compound according to the present invention and ANMP of *Candida albicans*, in particular of *Candida albicans* DSM-9456, for use in a method of treating and/or preventing interdigital dermatitis, digital dermatitis and/or interdigital phlegmon in animals, in particular in bovidae and/or pigs, most preferably in cattle.

In a further particularly preferred embodiment the invention refers to a composition comprising the modified chitosan or the hydro colloid or compound according to the present invention and a mixture of homogenised inactivated dermatophyte microconidia of *Trichophyton mentagrophytes, Trichophyton verrucosum, Trichophyton equinum, Trichophyton sarkisovii, Microsporum canis, Microsporum canis* var. *obesum, Microsporum canis* var. *distortum* and *Microsporum gypseum* and optionally ASMP of *Candida albicans*, in particular of *Candida albicans* DSM-9456. More preferably, the composition of the present invention comprises in addition to the modified chitosan or the hydro colloid or compound of the present invention the vaccine Polivac-TM and optionally ASMP of *Candida albicans*, in particular of *Candida albicans* DSM-9456, for use in a method of treating and/or preventing trichophytosis or dermatophytosis in animals, in particular in bovidae and/or pigs, most preferably in cattle.

In a further particularly preferred embodiment the invention refers to a composition comprising the modified chitosan or the hydro colloid or compound according to the present invention and AEMP of Chrisporium *tropicum*, in particular of Chrisporium *tropicum* DSM-28405 or *Microsporum canis* BINO 483, for use in a method of treating and/or preventing allergies, in particular allergic obstructive pulmonary disease, allergic skin diseases, allergic ear erythema, allergic rhinitis, allergic conjunctivitis, acute allergic contact dermatitis, chronic allergic contact eczema or atopic eczema, obstructive pulmonary disease, in particular chronic obstructive pulmonary disease, skin diseases, ear erythema, rhinitis, conjunctivitis, dermatophytosis, mycosis of skin or warts, in particular Common warts, obstructive pulmonary disease, in particular chronic obstructive pulmonary disease, skin diseases, in particular dermatitis, ear erythema, rhinitis or conjunctivitis in humans and/or animals, in particular a mammals, more preferably bovidae and/or pigs, most preferably cattle or horses, but also dogs, cats or other farm or domestic animals.

The modified chitosan, the hydro colloid, the compound and the compositions of the present invention are able to modulate the immune system, i.e. they have immunostimulatory properties. They can be used as a vaccine for preventing the subject from the diseases as outlined herein. Alternatively or in addition, they can be used to treat and cure the subject from the diseases as outlined herein. The modified chitosan, the hydro colloid and the compositions can be administered by known administration routes as e.g. oral, parenterally, by intramuscular injection, by intracutaneous injection, by percutaneous injection, by instillation, intracisternally, intrauterine, rectal, subcutaneous and/or topically, preferably cutaneously, more preferably intramuscular injection and/or intracutaneous injection and/or topically on the skin and/or topically on the mucous membrane. They may be administered in the absence or in the presence of one or more additional immunostimulatory substances. In one embodiment said one or more additional immunostimulatory substances are administered separately to the modified chitosan, compound or compositions of the present invention. In another embodiment the one or more additional immunostimulatory substances are comprised in or added to the compositions of the present invention.

Said one or more immunostimulatory substance is preferably an adjuvant, preferably selected from the group consisting of vitamin-E acetate, o/w-emulsion, aluminium phosphate, aluminium oxide, aluminium hydroxide/methyl cellulose gel, an oil-emulsion, muramil-dipeptides, Freund's adjuvants and saponins and/or at least one cytokine, preferably selected from the group consisting of IL 2, IL 12 and INF-Gamma.

In a preferred embodiment the compositions of the present invention is a vaccine and/or is used as a vaccine.

In a further aspect the present invention relates to a modified chitosan, a hydro colloid a compound or a composition of the present invention for use in a method of treatment of the animal and/or human body by therapy. Such method typically comprises administering to a subject an effective amount of the modified chitosan a composition, preferably a pharmaceutical composition, or the hydro colloid of the present invention. The subject may for example be a human or an animal, in particular a mammal, more preferably bovidae and/or pigs, most preferably cattle, but also dogs, cats or other farm or domestic animals. In particular, the modified chitosan, the hydro colloid or the compositions, in particular pharmaceutical compositions, of the present invention may be used in methods for the treatment or prevention of the diseases as outlined above. The method of treatment may comprise the treatment and/or prevention of bacterial, mycotic and/or viral infections of the skin, the ear, the lung, the nose, the leg, the hoof, the claws, the back of the foot and/or the interdigital space. Said infections may be caused by *Dichelobacter nodosus, Fusobacterium necroforun, Fusobacterium* spp, *Treponema* spp such as *T. phagedenis, T. vincentii, and T denticola, Campylobacter* spp, *Staphylococcus aureus, Escherichia coli, Arcanobacterium pyogenes, Prevotella* spp., *Trichophyton* spp. such as *T. verrucosum, T. mentagrophytes, T. sarkisovii,*
*T. equinum, T. schonleinii, T. rubrum, T. tonsurans, T. interdigitale,* and/or *Microsporum* spp. such as *M. canis, M. canis* var. *distortum, M. canis* var. *obesum, M. gypseum,* and/or *Malassezia* spp. such as *M. pachydermatitis, M. furfur, M. dermatitis* and/or HPV—Human Papillomavirus from genera Papillornavirus family Papoviridae such as HPV-2, HPV-3, HPV-4, HPV-6, HPV-11.

The dosage and route of administration used in a method of treatment and/or prophylaxis according to the present invention depends on the specific disease/site of infection to be treated. The route of administration may be for example oral, parenterally, by intramuscular injection, by intracutaneous injection, by percutaneous injection, by instillation, intracisternally, intrauterine, rectal, subcutaneous and/or topically, preferably cutaneously, more preferably intramuscular injection and/or intracutaneous injection and/or topically on the skin and/or topically on the mucous membrane or any other route of administration.

Preferred doses for the composition of the present invention are about 0.001 to about 0.5 ml/kg with a concentration of about 0.1 mg/ml to about 1.0 mg/ml and/or about $30 \times 10^6$ to about $80 \times 10^6$ microconidia and/or blastospores and/or particles of ANMP. Preferably, the composition of the present invention is administered about 1 to about 5 times. The interval between the administrations is preferably about 12 hours to about 21 days.

The following examples explain the present invention but are not considered to be limiting.

EXAMPLE 1

The First Stage.

Dilution (Dissolution) of Chitosan 40 g of the polysaccharide chitosan was sterilized by autoclavation and added under stirring to 8 liters of sterile water for injection acidified with 40 ml of 100% acetic acid to obtain a suspension. The suspension was mixed in a sterile tank for 24 hours to obtain a gel suspension. Undissolved particles were removed by filtration through a metal grid with a cell of 200 μm-300 μm. 4 N sodium hydroxide (NaOH) were added dropwise to the gel to obtain a final pH of 8.0. Upon that white flakes precipitated. The suspension was stirred for 30 minutes. The resultant biological material of the precipitate contained in its structure diacetylated chitosan. The precipitate was harvested by centrifugation for 50 minutes at 4500 revolutions per minutes.

Modification of the Biological Material Comprising Diacetylated Chitosan

The obtained suspended material was homogenized in a closed sterile homogenizer in 7 liters of sterile water for injection. 8 mL of 98% valerianic acid chloride (valeryl chloride, pentanoyl chloride) were added dropwise to the suspension under constant stirring. Subsequently, the suspension was stirred for 24 hours. To support the dissolution of flakes and unsolved particles 4N hydrochloric acid solution was added under stirring until the suspension had a pH of 5.8. Sterile water for injection was added to obtain an end volume of 8 liters. After that the modified polysaccharide was used to prepare the final product.

Characteristics of the Obtained Biological Material Comprising Modified Chitosan:

| Parameters | Characteristics |
| --- | --- |
| Chemical formula | unknown |
| Appearance | Clear gel |

| Parameters | Characteristics |
|---|---|
| Smell | Absent or faint smell of acetic acid |
| Deacetylation | >93% |
| Mineral content | >0.9% |
| Solubility in water | Soluble |
| Solubility in 1% solution of acetic acid | Soluble |

The second stage. For obtaining the final product 2 liters of the biological material comprising modified chitosan were adjusted to a volume of 15 liters by adding sterile water for injection under stirring. Then 500 ml of chlorocresol solution containing 30 grams chlorocresol were added to the mixture. The resultant suspension was adjusted to a volume of 30 liters. The resultant suspension was sterilized by heating for 40 minutes at 70° C. three times at intervals of 24 hours. The resultant sterile product was dispensed into vials under aseptic conditions.

EXAMPLE 2

Dilution (Dissolution) of Chitosan 4 g of the polysaccharide chitosan was added under stirring to 0.8 liters of sterile water for injection to obtain a suspension. 4 ml of 100% acetic acid were added and the suspension was mixed in a sterile tank for 24 hours to obtain a gel suspension. Undissolved particles were removed by filtration through a metal grid with a cell of 200 μm-300 μm. 4 N sodium hydroxide (NaOH) were added dropwise to the gel to obtain a final pH of 8.0. Upon that white flakes precipitated. The suspension was stirred for 40 minutes. The resultant biological material of the precipitate contained in its structure diacetylated chitosan. The precipitate was harvested by centrifugation for 45 minutes at 4500 revolutions per minutes.

Modification of the Biological Material Comprising Diacetylated Chitosan

The obtained suspended material was homogenized in a closed sterile homogenizer in 4 liters of sterile water for injection. 0.8 mL of 98% valerianic acid chloride (valeryl chloride, pentanoyl chloride) were added dropwise to the suspension under constant stirring. Subsequently, the suspension was stirred for 24 hours. To support the dissolution of flakes and unsolved particles 4N hydrochloric acid solution was added under stirring until the suspension had a pH of 5.5. After that the modified polysaccharide was used to prepare the final product.

Characteristics of the Obtained Biological Material Comprising Modified Chitosan:

| Parameters | Characteristics |
|---|---|
| Chemical formula | unknown |
| Appearance | Clear gel |
| Smell | Absent or faint smell of acetic acid |
| Deacetylation | >93% |
| Mineral content | >0.9% |
| Solubility in water | Soluble |
| Solubility in 1% solution of acetic acid | Soluble |

The second stage. For obtaining the final product 200 ml of the modified chitosan were resuspended in 1.5 liters of sterile water for injection and 50 ml of chlorocresol solution containing 2 g of the active substance were added under stirring. The obtained suspension was adjusted to a volume of 2 liters. The obtained suspension was sterilized by heating for 40 minutes at 70° C. three times with intervals of 24 hours. The resultant sterile product was dispensed into vials under aseptic conditions.

EXAMPLE 3

Dilution (Dissolution) of Chitosan 80 g of the polysaccharide chitosan was sterilized by autoclavation and added under stirring to 16 liters of sterile water for injection acidified with 80 ml of 100% acetic acid to obtain a suspension. The suspension was mixed in a sterile tank for 24 hours to obtain a gel suspension. Undissolved particles were removed by filtration through a metal grid with a cell of 200 μm-300 μm. 4 N sodium hydroxide (NaOH) were added dropwise to the gel to obtain a final pH of 8.0. Upon that white flakes precipitated. The suspension was stirred for 50 minutes. The resultant biological material of the precipitate contained in its structure diacetylated chitosan. The precipitate was harvested by centrifugation for 60 minutes at 5000 revolutions per minutes.

Modification of the Biological Material Comprising Diacetylated Chitosan

The obtained suspended material was homogenized in a closed sterile homogenizer in 4 liters of sterile water for injection. 16 mL of 98% valerianic acid chloride (valeryl chloride, pentanoyl chloride) were added dropwise to the suspension under constant stirring. Moreover, 4 liters of sterile water for injection was added and 3% solution of glutamic acid was added under stirring until the suspension had a pH of 5.0. Sterile water for injection was added to obtain an end volume of 8 liters. The suspension was stirred after that for 24 hours. After that the modified polysaccharide was used to prepare the final product.

Characteristics of the Obtained Biological Material Comprising Modified Chitosan

| Parameters | Characteristics |
|---|---|
| Chemical formula | unknown |
| Appearance | Clear gel |
| Smell | Absent or faint smell of acetic acid |
| Deacetylation | >90% |
| Mineral content | >0.8% |
| Solubility in water | Soluble |
| Solubility in 1% solution of acetic acid | Soluble |

The second stage. For obtaining the final product 4000 ml of the modified chitosan were resuspended in 30 liters of sterile water for injection and 50 ml of chlorocresol solution containing 40 g of the active substance were added under stirring. The obtained suspension was adjusted to a volume of 40 liters. The obtained suspension was sterilized by heating for 45 minutes at 72° C. three times with intervals of 24 hours. The resultant sterile product was dispensed into vials under aseptic conditions.

EXAMPLE 4

Dilution (Dissolution) of Chitosan 16 g of the polysaccharide chitosan (deacetylation of 65%-72%, viscosity of 151-350 mPas, 80-200 kDa) was sterilized by autoclavation and added under stirring to 3 liters of sterile water for injection acidified with 164 ml of 100% acetic acid to obtain a suspension. The suspension was mixed in a sterile tank for 24 hours to obtain a gel suspension. Undissolved particles were removed by filtration through a metal grid with a cell of 200 µm-300 µm. 4 N sodium hydroxide (NaOH) were added dropwise to the gel to obtain a final pH of 8.5. Upon that white flakes precipitated. The suspension was stirred for 30 minutes. The resultant biological material of the precipitate contained in its structure diacetylated chitosan. The precipitate was harvested by centrifugation for 50 minutes at 5000 revolutions per minutes.

Modification of the Biological Material Comprising Diacetylated Chitosan

The obtained suspended material was homogenized in a closed sterile homogenizer in 1 liters of sterile water for injection. 0.6 mL of 98% valerianic acid chloride (valeryl chloride, pentanoyl chloride) were added dropwise to the suspension under constant stirring. Moreover, a 0.5% solution of paraaminobenzoic acid was added under stirring until the suspension had a pH of 5.4. Sterile water for injection was added to obtain an end volume of 1.6 liters. The suspension was stirred after that for 24 hours. After that the modified polysaccharide was used to prepare the final product.

Characteristics of the Obtained Biological Material Comprising Modified Chitosan

| Parameters | Characteristics |
| --- | --- |
| Chemical formula | unknown |
| Appearance | Clear gel |
| Smell | Absent or faint smell of acetic acid |
| Deacetylation | >89% |
| Mineral content | >1.0% |
| Solubility in water | Soluble |
| Solubility in 1% solution of acetic acid | Soluble |

The second stage. For obtaining the final product 1000 ml of the modified fraction were resuspended in 8 liters of sterile water for injection and 200 ml of chlorocresol solution containing 10 g of the active substance were added under stirring. The obtained suspension was adjusted to a volume of 10 liters. The obtained suspension was sterilized by heating for 45 minutes at 65° C. three times with intervals of 24 hours. The resultant sterile product was dispensed into vials under aseptic conditions.

EXAMPLE 5

The product is prepared from chitosan. The product is prepared in two stages. The first stage is oriented to obtain a chitosan solution; the second stage is oriented to obtain the final product.

The First Stage.

40 g chitosan (deacetylation of 82%-87%, a viscosity of 151-350 mPas, molecular weight 150-300 kDa) was sterilized by autoclavation and added under stirring to 3.5 liters of sterile water for injection. 40 ml of 100% acetic acid were added to the obtained suspension and the volume was adjusted to an final volume of 4 liters with water for injection. The suspension was stirred in a sterile container for 24 hours until a gel suspension was obtained. 4 N sodium hydroxide (NaOH) were added dropwise to the obtained suspension to obtain a final pH of 8.0. Upon that white flakes precipitated. The suspension was stirred for 30 minutes. The resultant biological material of the precipitate contained in its structure a linear diacetylated polysaccharide of N-acetyl-1,4-β-D-glucopyranosamine (chitosan). The precipitate was harvested by centrifugation for 55 minutes at 4500 revolutions per minutes.

Modification of Chitosan

The precipitate was suspended in 4 liters of sterile water for injections and 4N hydrochloric acid were added under stirring to obtain a pH of 5.4. The suspension was stirred for 24 hours until all flakes were dissolved and a gel suspension was obtained. The gel suspension was used to prepare the final product.

The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture under stirring. The resultant suspension was adjusted to a volume of 30 liters. The resultant sterile product was dispensed into vials under aseptic conditions.

EXAMPLE 6

The product was prepared from chitosan. The product was prepared in two stages. The first stage is oriented to obtain a solution of modified chitosan; the second stage is oriented to obtain the final product.

The first stage. Chitosan with a deacetylation of 62%-67%, a viscosity of 70-200 mPas and a molecular weight of 100-250 kDa was used as raw material. 40 grams of the polysaccharide was sterilized by autoclaving and added into 3.5 liters of water for injection under stirring. 40 ml of 100% acetic acid were added to the obtained suspension. The final volume was adjusted with water for injection to 4 liters. Suspended polysaccharide was stirred in a sterile container for 24 hours until a gel suspension was obtained. Unsolved particles were removed by filtration through a metal grid with a cell size of 200 µm-300 µm.

4 N sodium hydroxide (NaOH) were added dropwise to the prepared suspension to obtain a final pH of 8.0. Upon that white flakes precipitated. The suspension was stirred for 30 minutes. The received biological material contained in its structure a linear diacetylated polysaccharide of N-acetyl-1,4-β-D-glucopyranosamine (chitosan). The precipitate was harvested by centrifugation for 60 minutes at 4500 revolutions per minutes.

Modification of Chitosan 4 mL 98% of valerian acid chloride was add of dropwise to the suspension under the constant stirring. The obtained suspended material was stirred for one hour. Flakes and unsolved particles were resuspended in 4 liters of sterile water for injections and 4N hydrochloric acid was added under stirring to get a pH of 5.0. The suspension is stirred for 28 hours until all flakes were dissolved and a gel suspension was obtained.

The second stage. For obtaining the final product 3 liters of the modified polysaccharide were adjusted to a volume of 25 liters by adding sterile water for injection under stirring. Then 500 ml of chlorocresol solution containing 30 grams of the active ingredient were added to the mixture. The resultant suspension was adjusted to a volume of 30 liters. The resultant sterile product was dispensed into vials under sterile conditions.

EXAMPLE 7

The product was prepared from chitosan. The product was prepared in two stages. The first stage was oriented to obtain a solution of modified chitosan; the second stage was oriented to obtain the final product.

The first stage. Chitosan with a deacetylation of 77%-82%, a viscosity of 2700-3300 mPas and a molecular weight of 300-700 kDa was used as raw material. 40 grams of the polysaccharide was sterilized by autoclaving and added to 3.5 liters of water for injection under stirring. 40 ml of 100% acetic acid were added to the obtained suspension. The final volume was adjusted to 4 liters with water for injection. Suspended polysaccharide was stirred in a sterile container for 30 hours until a gel suspension was obtained. Unsolved particles were removed by filtration through a metal grid with a cell of 200 μm-300 μm. 4 N sodium hydroxide (NaOH) were added dropwise to the obtained suspension to obtain a final pH of 8.0. Upon that white flakes precipitated. The suspension was stirred for 30 minutes. The resultant biological material contained in its structure a linear diacetylated polysaccharide of N-acetyl-1,4-β-D-glucopyranosamine (chitosan). The precipitate was harvest by centrifugation for 45 minutes at 5000 revolutions per minutes.

Modification of the Biological Material Comprising Chitosan 8 mL of 90% lactic acid were added dropwise to the suspension under the constant stirring. The obtained suspended material was stirred for one hour. Flakes and unsolved particles were resuspended in 4 liters of sterile water for injections and 4N hydrochloric acid were added under stirring until a pH of 5.6 is obtained. The suspension is stirred for 48 hours until all flakes were dissolved and a gel suspension was obtained.

The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The resultant sterile product was dispensed into vials under aseptic conditions.

EXAMPLE 8

The product was prepared from chitosan. The product was prepared in two stages. The first stage was oriented to obtain a solution of modified chitosan, the second stage was oriented to obtain the final product.

The first stage. Chitosan with a deacetylation of 82%-87%, a viscosity of 151-350 mPas and a molecular weight of 150-300 kDa was used as raw material. 40 grams of the polysaccharide was sterilized by autoclaving and added to 3.5 liters of water for injection under stirring. 40 ml of 100% acetic acid were added to the obtained suspension. The final volume was adjusted to 4 liters with water for injection. The suspended polysaccharide was stirred in a sterile container for 36 hours until a gel suspension was obtained. Unsolved particles were removed by filtration through a metal grid with a cell of 200 μm-300 μm. 4 N sodium hydroxide (NaOH) were added dropwise to the obtained suspension to obtain a final pH of 8.0. Upon that white flakes precipitated. The suspension was stirred for 30 minutes. The resultant biological material contained in its structure a linear diacetylated polysaccharide of N-acetyl-1,4-β-D-glucopyranosamine (chitosan). The precipitate was harvest by centrifugation for 50 minutes at 4500 revolutions per minutes.

Modification of the Biological Material Comprising Chitosan

A 0.2% solution of paraaminobenzoic acid was added to the precipitate under constant stirring up to 4 liters. The obtained suspended material was stirred for one hour. Flakes and unsolved particles were suspended in solution of paraaminobenzoic acid and 4N hydrochloric acid were added under stirring until a pH of 5.6 is obtained. The suspension was stirred for 70 hours until all flakes were dissolved and a gel suspension was obtained.

The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The resultant sterile product was dispensed into vials under aseptic conditions.

EXAMPLE 9

The product was prepared from chitosan. The product was prepared in two stages. The first stage was oriented to obtain a solution of modified chitosan; the second stage was oriented to obtain the final product.

The first stage. Chitosan with a deacetylation of 67%-72%, a viscosity of 151-350 mPas and a molecular weight of 150-300 kDa was used as raw material. 40 grams of the polysaccharide was sterilized by autoclaving and added to 3.5 liters of water for injection under stirring. 40 ml of 100% acetic acid were added to the obtained suspension. The final volume was adjusted with water for injection to 4 liters. Suspended polysaccharide was stirred in a sterile container for 24 hours until a gel suspension was obtained. Unsolved particles were removed by filtration through a metal grid with a cell of 200 μm-300 μm. 4 N sodium hydroxide (NaOH) were added dropwise to the obtained suspension to obtain a final pH of 8.0. Upon that white flakes precipitated. The suspension was stirred for 30 minutes. The resultant biological material contained in its structure a linear diacetylated polysaccharide of N-acetyl-1,4-β-D-glucopyranosamine (chitosan). The precipitate was harvested by centrifugation for 60 minutes at 4500 revolutions per minutes.

Modification of the Biological Material Comprising Chitosan

A 0.1% solution of sodium salt of glucuronic acid was added to the precipitate under constant stirring up to 4 liters. The obtained suspended material was stirred for one hour. Flakes and unsolved particles were resuspended in solution of glucuronic acid and 4N hydrochloric acid were added under stirring until a pH of 5.6 was obtained. The suspension was stirred for 72 hours until all flakes were dissolved and a gel suspension was obtained.

The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The resultant sterile product was dispensed into vials under aseptic conditions.

EXAMPLE 10

The product was prepared from chitosan. The product was prepared in two stages. The first stage was oriented to obtain a solution of chitosan; the second stage was oriented to obtain the final product.

The first stage. Chitosan with a deacetylation of 67%-72%, a viscosity of 151-350 mPas and a molecular weight of 150-300 kDa was used as raw material. 40 grams of the polysaccharide was sterilized by autoclaving and added to 3.5 liters of water for injection under stirring. 8 ml of 98% sodium salt of valerianic acid were added to the obtained suspension. The final volume was adjusted to 4 liters with water for injection. The suspended polysaccharide was stirred in a sterile container for 48 hours until a gel suspension was obtained. Unsolved particles were removed by filtration through a metal grid with a cell of 200 µm-300 µm.

The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The resultant sterile product was dispensed into vials under aseptic conditions.

EXAMPLE 11

The product was prepared from chitosan. The product was prepared in two stages. The first stage was oriented to obtain a solution of chitosan; the second stage was oriented to obtain the final product.

The first stage. Chitosan with deacetylation of 67%-72%, a viscosity of 151-350 mPas and a molecular weight of 150-300 kDa was used as raw material. 40 grams of polysaccharide was sterilized by autoclaving and added to 3.9 liters of 0.2% paraaminobenzoic acid in water for injection under stirring. 4N hydrochloric acid solution were added under stirring until getting a pH of 5.6 and to obtain a gel suspension. The final volume was adjusted to 4 liters with water for injection. Suspended polysaccharide was stirred in a sterile container for 72 hours until a gel suspension was obtained. Unsolved particles were removed by filtration through a metal grid with a cell of 200 µm-300 µm.

The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The resultant sterile product was dispensed into vials under aseptic conditions.

EXAMPLE 12

The product was prepared from chitosan. The product was prepared in two stages. The first stage was oriented to obtain a solution of chitosan; the second stage was oriented to obtain the final product.

The first stage. Chitosan with a deacetylation of 67%-72%, a viscosity of 151-350 mPas and a molecular weight of 150-300 kDa was used as raw material. 40 grams of the polysaccharide was sterilized by autoclaving and added to 3.5 liters of a 0.1% solution of sodium salt of glucuronic acid under stirring. To obtain a gel suspension 4N hydrochloric acid solution was added under stirring until getting a pH of 5.0. The final volume was adjusted with water for injection to 4 liters. Suspended polysaccharide was stirred in a sterile container for 78 hours until a gel suspension was obtained. Unsolved particles were removed by filtration through a metal grid with a cell of 200 µm-300 µm.

The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The resultant sterile product was dispensed into vials under aseptic conditions.

EXAMPLE 13

The product was prepared from chitosan. The product was prepared in two stages. The first stage was oriented to obtain a solution of chitosan; the second stage was oriented to obtain the final product.

The first stage. Chitosan with a deacetylation of 67%-72%, a viscosity of 151-350 mPas and a molecular weight of 150-300 kDa was used as raw material. 40 grams of the polysaccharide was sterilized by autoclaving and added to 3.5 liters of water for injection under stirring. 8 ml of 90% lactic acid were added to the obtained suspension. For dissolving the flakes and particles 4N hydrochloric acid solution was added until getting a pH of 5.7. The final volume was adjusted with water for injection to 4 liters. Suspended polysaccharide was stirred in a sterile container for 36 hours until a gel suspension was obtained. Unsolved particles were removed by filtration through a metal grid with a cell of 200 µm-300 µm.

The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The resultant sterile product was dispensed into vials under aseptic conditions.

EXAMPLE 14

The product was prepared by performing the $1^{st}$ stage of example 1 in the volume of 2 liters and by mixing it with 2 liters of the product prepared according to the example 5.

The second stage. For obtaining the final product 4 liters of the modified polysaccharide were adjusted to a volume of 35 liters by adding sterile water for injection under stirring. Then, 500 mL, of thimerosal containing 1.6 grams of active substance were added to the mixture. The resultant suspension was adjusted to the volume of 40 liters. The resultant sterile product was dispensed into vials under aseptic conditions.

EXAMPLE 15

The product was prepared by performing the $1^{st}$ stage of example 5 in the volume of 2 liters and by mixing it with 2 liters of the product prepared according to the example 6.

The second stage. For obtaining the final product 4 liters of the modified polysaccharide were adjusted to a volume of 35 liters by adding sterile water for injection under stirring. Then, 500 mL of thimerosal containing 2 grams of the active substance were added to the mixture. The resultant suspension was adjusted to a volume of 40 liters. The resultant sterile product was dispensed into vials under aseptic conditions.

EXAMPLE 16

Product prepared was prepared by performing the $1^{st}$ stage of the example 5 in the volume of 2 liters and by mixing it with 2 liters of the product prepared according to the example 7.

The second stage. For obtaining the final product 4 liters of the modified polysaccharide were adjusted to a volume of 35 liters by adding sterile water for injection under stirring. Then, 500 mL of thimerosal containing 1.8 grams of the active substance were added to the mixture. The resultant suspension was adjusted to a volume of 40 liters. The resultant sterile product was dispensed into vials under aseptic conditions.

EXAMPLE 17 the product was prepared by performing the 1$^{st}$ stage of example 5 in the volume of 2 liters and by mixing it with 2 liters of the product prepared according to the example 8.

The second stage. For obtaining the final product 4 liters of the modified polysaccharide were adjusted to a volume of 35 liters by adding sterile water for injection under stirring. Then, 500 mL of thimerosal containing 1.8 grams of active substance were added to the mixture. The resultant suspension was adjusted to a volume of 40 liters. The resultant sterile product was dispensed into vials under aseptic conditions.

EXAMPLE 18

The product was prepared by performing the stage of example 5 in the volume of 2 liters and by mixing it with 2 liters of the product prepared according to the example 9.

The second stage. For obtaining the final product 4 liters of the modified polysaccharide were adjusted to a volume of 35 liters by adding sterile water for injection under stirring. Then, 500 mL of thimerosal containing 1.6 grams of the active substance were added to the mixture. The resultant suspension was adjusted to a volume of 40 liters. The resultant sterile product was dispensed into vials under aseptic conditions.

EXAMPLE 19

The product was prepared by performing the 1st stage of example 6 in the volume of 2 liters and by mixing it with 2 liters of the product prepared according to the example 9.

The second stage. For obtaining the final product 4 liters of the modified polysaccharide were adjusted to a volume of 35 liters by adding sterile water for injection under stirring. Then, 500 mL of thimerosal containing 1.6 grams of the active substance were added to the mixture. The resultant suspension was adjusted to a volume of 40 liters. The resultant sterile product was dispensed into vials under aseptic conditions.

EXAMPLE 20

The product was prepared by performing the 1st stage of example 6 in the volume of 2 liters and by mixing it with 2 liters of the product prepared according to the example 8.

The second stage. For obtaining the final product 4 liters of the modified polysaccharide were adjusted to a volume of 35 liters by adding sterile water for injection under stirring. Then, 500 mL of thimerosal containing 1.6 grams of the active substance were added to the mixture. The resultant suspension was adjusted to a volume of 40 liters. The resultant sterile product was dispensed into vials under aseptic conditions.

EXAMPLE 21

The product was prepared by performing the 1st stage of example 6 in the volume of 2 liters and by mixing it with 2 liters of the product prepared according to the example 8.

The second stage. For obtaining the final product 4 liters of the modified polysaccharide were adjusted to a volume of 35 liters by adding sterile water for injection under stirring. Then, 500 mL of formalin containing 80 mL of the active substance were added to the mixture. The resultant suspension was adjusted to a volume of 40 liters. The resultant sterile product was dispensed into vials under aseptic conditions.

EXAMPLE 22

The product was prepared by performing the 1st stage of example 6 in the volume of 2 liters and by mixing it with 2 liters of the product prepared according to the example 9.

The second stage. For obtaining the final product 4 liters of the modified polysaccharide were adjusted to a volume of 35 liters by adding sterile water for injection under stirring. Then, 500 mL of formalin solution containing 85 mL of the active substance were added to the mixture. The resultant suspension was adjusted to a volume of 40 liters. The resultant sterile product was dispensed into vials under aseptic conditions.

EXAMPLE 23

The product was prepared according to the example 5 with the difference that in the second stage of preparation for obtaining the resultant product 3 liters of the modified polysaccharide were adjusted to a volume of 10 liters by adding sterile water for injection under stirring. Then, 500 ml of chlorocresol solution containing 15 grams of the active substance were added to the mixture. The resultant suspension was adjusted to a volume of 15 liters. The resultant sterile product was dispensed into vials under aseptic conditions.

EXAMPLE 24

The product was prepared according to the example 6 with the difference that in the second stage of preparation for obtaining the resultant product 3 liters of the modified polysaccharide were adjusted to a volume of 10 liters by adding sterile water for injection under stirring. Then, 500 ml of chlorocresol solution containing 15 grams of the active substance were added to the mixture. The resultant suspension was adjusted to a volume of 15 liters. The resultant sterile product was dispensed into vials under aseptic conditions.

EXAMPLE 25

The product was prepared according to the example 7 with the difference that in the second stage of preparation for obtaining the resultant product 3 liters of the modified polysaccharide were adjusted to a volume of 10 liters by adding sterile water for injection under stirring. Then, 500 ml of thimerosal containing 1.6 grams of the active substance were added to the mixture. The resultant suspension was adjusted to a volume of 15 liters. The resultant sterile product was dispensed into vials under aseptic conditions.

EXAMPLE 26

The product was prepared according to the example 8 with the difference that in the second stage of preparation for obtaining the resultant product 3 liters of the modified polysaccharide were adjusted to a volume of 10 liters by adding sterile water for injection under stirring. Then, 500 ml of formalin solution containing 30 mL of the active substance were added to the mixture. The resultant suspension was adjusted to a volume of 15 liters. The resultant sterile product was dispensed into vials under aseptic conditions.

EXAMPLE 27

The product was prepared according to the example 9 with the difference that in the second stage of preparation for obtaining the resultant product 3 liters of the modified polysaccharide were adjusted to a volume of 10 liters by adding sterile water for injection under stirring. Then, 500 ml of thimerosal containing 0.6 grams of the active substance were added to the mixture. The resultant suspension was adjusted to a volume of 15 liters. The resultant sterile product was dispensed into vials under aseptic conditions.

EXAMPLE 28

The product was prepared according to the example 6 with the difference that in the second stage of preparation for obtaining the resultant product 3 liters of the modified polysaccharide were adjusted to a volume of 5 liters by adding sterile water for injection under stirring. Then, 500 ml of chlorocresol solution containing 6 grams of the active substance were added to the mixture. The resultant suspension was adjusted to a volume of 6 liters. The resultant sterile product was dispensed into vials under aseptic conditions.

EXAMPLE 29

The product was prepared according to the example 7 with the difference that in the second stage of preparation for obtaining the resultant product 3 liters of the modified polysaccharide were adjusted to a volume of 5 liters by adding sterile water for injection under stirring. Then, 500 ml of thimerosal containing 0.24 grams of the active substance were added to the mixture. The resultant suspension was adjusted to a volume of 6 liters. The resultant sterile product was dispensed into vials under aseptic conditions.

EXAMPLE 30

The product was prepared according to the example 8 with the difference that in the second stage of preparation for obtaining the resultant product 3 liters of the modified polysaccharide were adjusted to a volume of 5 liters by adding sterile water for injection under stirring. Then, 500 ml of formalin solution containing 12 mL of the active substance were added to the mixture. The resultant suspension was adjusted to a volume of 6 liters. The resultant sterile product was dispensed into vials under aseptic conditions.

EXAMPLE 31

The product was prepared according to the example 9 with the difference that in the second stage of preparation for obtaining the resultant product 3 liters of the modified polysaccharide were adjusted to a volume of 5 liters by adding sterile water for injection under stirring. Then, 500 ml of merthiolate solution containing 0.24 grams of the active substance were added to the mixture. The resultant suspension was adjusted to a volume of 6 liters. The resultant sterile product was dispensed into vials under aseptic conditions.

EXAMPLE 32

The product was prepared according to the example 8 with the difference that in the second stage of preparation for obtaining the resultant product 3 liters of the modified polysaccharide were adjusted to a volume of 10 liters by adding sterile water for injection under stirring. Then, 500 ml of neomycin solution containing 150 g of the active substance were added to the mixture. The resultant suspension was adjusted to a volume of 15 liters. The resultant sterile product was dispensed into vials under aseptic conditions.

EXAMPLE 33

The product was prepared according to the example 8 with the difference that in the second stage of preparation for obtaining the resultant product 3 liters of the modified polysaccharide were adjusted to a volume of 10 liters by adding sterile water for injection under stirring. Then, 500 ml of penicillin sodium and potassium salts solution containing 300 g (300.000.000 UE) of the active substance were added to the mixture. The resultant suspension was adjusted to a volume of 15 liters. The resultant sterile product was dispensed into vials under aseptic conditions.

EXAMPLE 34

The product was prepared according to the example 8 with the difference that in the second stage of preparation for obtaining the resultant product 3 liters of the modified polysaccharide were adjusted to a volume of 10 liters by adding sterile water for injection under stirring. Then, 500 ml of penicillin sodium and potassium salts solution containing 300 g (300.000.000 UE) of the active substance and 500 ml of neomycin solution containing 150 g of the active substance were added to the mixture. The resultant suspension was adjusted to a volume of 15 liters. The resultant sterile product was dispensed into vials under aseptic conditions.

EXAMPLE 35

The product was prepared by performing the 1st stage of example 7 in the volume of 2 liters and by mixing it with 2 liters of the product prepared according to the example 8.

The second stage. For obtaining the final product 4 liters of the modified polysaccharide were adjusted to a volume of 15 liters by adding sterile water for injection under stirring. Then, 500 ml of formalin solution containing 30 mL of the active substance were added to the mixture. The resultant suspension was adjusted to a volume of 20 liters. The resultant sterile product was dispensed into vials under aseptic conditions.

EXAMPLE 36

The product was prepared by performing the 1st stage of example 7 in the volume of 2 liters and by mixing it with 2 liters of the product prepared according to the example 6.

The second stage. For obtaining the final product 4 liters of the modified polysaccharide were adjusted to a volume of 15 liters by adding sterile water for injection under stirring. Then, 500 ml of formalin solution containing 30 mL of the active substance were added to the mixture. The resultant suspension was adjusted to a volume of 20 liters. The resultant sterile product was dispensed into vials under aseptic conditions.

EXAMPLE 37

The product was prepared by performing the 1st stage of example 7 in the volume of 5 liters.

The second stage. For obtaining the final product 4 liters of the modified polysaccharide were adjusted to a volume of 15 liters by adding sterile water for injection under stirring. Then 500 ml of formalin solution containing 30 mL of the active substance were added to the mixture. The resultant suspension was adjusted to a volume of 20 liters. The resultant sterile product was dispensed into vials under aseptic conditions.

EXAMPLE 38

Dermatophyte culture of the species *Trichophyton mentagrophytes* DSM-7279 was cultivated on agar/wort, for example in 3-10 Roux flasks. The culture was cultivated for 15-30 days at 26-28° C. The fungal masses of the dermatophyte were lifted off and homogenised in an aqueous solution (for example 100-500 ml) of the product obtained according to example 6, but with the following difference in the second stage: The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The resultant sterile product was added to the fungal suspension to obtain a concentration of 45-80 million microconidia per ml for each homogenate. The homogenates were inactivated by adding formaldehyde directly to the cell suspension so that the cell suspension contained 0.2% (v/v) formaldehyde in the end. The mixture was incubated for 5-7 days at 37° C.

Vaccine preparable according to this method can e.g. be used for the prophylaxis and treatment of interdigital and/or digital dermatitis and/or interdigital phlegmon in animals.

EXAMPLE 39

Dermatophyte culture of the species *Trichophyton verrucosum* DSM-28406 was cultivated on agar/wort, for example in 3-10 Roux flasks. The culture was cultivated for 15-30 days at 26-28° C. The fungal masses of the dermatophyte were lifted off and homogenised in an aqueous solution (for example 100-500 ml) of the product prepared according to example 8 but with the following difference in the second stage: The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The resultant sterile product was added to the suspension to obtain a concentration of 45-80 million per ml for homogenate. The homogenates were inactivated by adding formaldehyde directly to the cell suspension so that the cell suspension contained 0.4% (v/v) formaldehyde in the end. The mixture was incubated for 5-7 days at 37° C.

Vaccine preparable according to this method can e.g. be used for the prophylaxis and treatment of interdigital and/or digital dermatitis and/or interdigital phlegmon and/or trihophytosis in animals.

EXAMPLE 40

The species *Candida albicans* DSM-9456 was cultivated on malt extract-agar or agar Sabouraud, for example in 3-10 Roux flasks. The Culture was cultivated for 4-7 days at 28-37° C. The blastospores were washed off with a physiological solution of sodium chloride or another suitable solution. The fungal masses of the dermatophyte were lifted off and homogenised in an aqueous solution (for example 100-500 ml) of the product prepared according to example 9 but with the following difference in the second stage: The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The resultant sterile product was added to the suspension to obtain a concentration of 40-90 million microconidia per ml for the homogenate. The homogenates were inactivated by adding formaldehyde directly to the cell suspension so that the cell suspension contained 0.3% (v/v) formaldehyde in the end. The mixture was incubated for 5-7 days at 37° C.

Vaccine preparable according to this method can e.g. be used for the prophylaxis and treatment of interdigital and/or digital dermatitis and/or interdigital phlegmon in animals.

EXAMPLE 41

First step: The species *Candida albicans* DSM-9456 was cultivated on malt extract-agar from Oxoid in 40 Roux flasks. The culture was cultivated for 4-7 days at 28-37° C. as described in EP 0564620. The resulting fungal biomass was lifted off and treated with an aqueous solution of NaOH with a concentration of 3% (w/v). Said alkaline treatment was performed at 80° C. for 6 h. Following the processing under aqueous alkaline conditions, the solid and liquid phases of the preparation were separated by centrifugation at 3500 g. After the alkaline treatment, the resulting supernatant was treated under acidic aqueous conditions, e.g. 50% acetic acid at a pH of 4.0 for 2 hours at temperatures of 4° to 8° C., whereafter separation of the solid and liquid layers took place. Then, the supernatant from the separation step was subjected to a precipitation step. The precipitation was performed by adding ethanol. A ratio of one volume supernatant to 3 volumes of alcohol resulted in good precipitation of the antigenic material. Finally, the ASMP preparation was lyophilised. Finally, the solid phase was lifted off and homogenised in the product obtained according to example 6, but with the following difference in the second stage:

The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The concentration of ASMP was adjusted to 400 µg per ml.

Vaccine preparable according to this method can e.g. be used for the prophylaxis and treatment of allergies.

EXAMPLE 42

First step: The species *Candida albicans* DSM-9456 was cultivated on malt extract-agar from Oxoid in 50 Roux flasks. The culture was cultivated for 4-7 days at 28-37° C. as described in EP 0564620. The resulting fungal biomass was lifted off and treated with an aqueous solution of NaOH with a concentration of 3% (w/v). Alkaline treatment was performed at 80° C. for 6 h. Following the processing under aqueous alkaline conditions, the solid and liquid phases of the preparation were separated by centrifugation at 3500 g. After the alkaline treatment, the resulting supernatant was treated under acidic aqueous conditions, e.g. 50% acetic acid at a pH of 4.0 for 2 hours at temperatures of 4° to 8° C., whereafter separation of the solid and liquid layers took place. Then, the supernatant from the separation step was subjected to a precipitation step. The precipitation was performed by adding ethanol. A ratio of one volume supernatant to 3 volumes of alcohol resulted in good precipitation of the antigenic material. Finally the ASMP preparation was lyophilised.

Finally the solid phase was lifted off and homogenised in the product obtained according to example 8, but with the following difference in the second stage: The second stage. For obtaining the final product 3 liters of the modified polysaccharide were adjusted to a volume of 25 liters by adding sterile water for injection under stirring. Then 500 ml of chlorocresol solution containing 30 grams of the active ingredient were added to the mixture. The resultant suspension was adjusted to a volume of 30 liters. The concentration of ASMP was adjusted to 200 µg per ml.

Vaccine preparable according to this method can e.g. be used for the prophylaxis and treatment of allergies.

EXAMPLE 43

First step: The species *Candida albicans* DSM-9456 was cultivated on malt extract-agar from Oxoid in 50 Roux flasks. Culture was cultivated for 4-7 days at 28-37° C. as described in EP 0564620. The resulting fungal biomass was lifted off and treated with an aqueous solution of NaOH with concentrations of 3% (w/v). Alkaline treatment was performed at 80° C. for 6 h. Following the processing under aqueous alkaline conditions, the solid and liquid phases of the preparation were separated by centrifugation at 3500 g. After the alkaline treatment, the resulting supernatant was treated under acidic aqueous conditions, e.g. 50% acetic acid at pH 4.0 for 2 hours at temperatures of 4° to 8° C., whereafter separation of the solid and liquid layers took place. Then, the supernatant from the separation step was subjected to a precipitation step. The precipitation was performed by adding ethanol. A ratio of one volume supernatant to 3 volumes of alcohol resulted in good precipitation of the antigenic material. Finally the ASMP preparation was lyophilised.

Finally the solid phase was lifted off and homogenised in the product obtained according to example 9, but with the following difference in the second stage: The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The concentration of ASMP was adjusted to 100 µg per ml.

Vaccine preparable according to this method can e.g. be used for the prophylaxis and treatment of allergies.

EXAMPLE 44

The fraction preparable according to this process consists of antigenic nonsoluble material comprising polysaccharide and/or glycopeptides (ANMP) according to PCT/EP96/03535. The species *Candida albicans* DSM-9456 was cultivated on malt extract-agar from Oxoid in 50 Roux flasks. The culture was cultivated for 4-7 days at 28-37° C. as described in EP 0564620. The resulting fungal biomass was lifted off and treated with an aqueous solution of alkali with concentrations of 4% (w/v) NaOH. The treatment was performed at 80° C. for up to 6 h. Following the processing under aqueous alkaline conditions, the solid and liquid phases of the preparation were separated by centrifugation at forces of about 3500 g. After alkaline treatment, the solid phase was treated with a 50% solution of acetic acid. After acidic treatment the solid phase was washed with distilled water for five times. Finally the solid phase was lifted off and homogenised in the product obtained according to example 6, but with the following difference in the second stage: The second stage. For obtaining the final product 3 liters of the modified polysaccharide were adjusted to a volume of 25 liters by adding sterile water for injection under stirring. Then, 500 ml of chlorocresol solution containing 30 grams of the active ingredient were added to the mixture. The resultant suspension was adjusted to a volume of 30 liters. The concentration of particles was adjusted to 30-90 million per ml.

Vaccine preparable according to this method can e.g. be used for the prophylaxis and treatment of interdigital and/or digital dermatitis and/or interdigital phlegmon in animals.

EXAMPLE 45

Dermatophyte culture of the species *Trichophyton verrucosum* DSM-28406 was cultivated on agar/wort, for example in 3-10 Roux flasks. The culture was cultivated for 15-30 days at 26-28° C. The fungal masses of the dermatophyte was lifted off and homogenised in an aqueous solution (for example 100-500 ml) of the product obtained according to example 6, but with the following difference in the second stage: The second stage. For obtaining the final product 3 liters of the modified polysaccharide were adjusted to a volume of 10 liters by adding sterile water for injection under stirring. Then 500 ml of a chlorocresol solution containing 30 grams of the active ingredient were added to the mixture. The resultant suspension was adjusted to a volume of 15 liters. The resultant sterile product was added to the fungal suspension to obtain a concentration of 45-60 million microconidia per ml for each homogenate. The homogenates were inactivated by adding formaldehyde directly to the cell suspension so that the cell suspension contained 0.2% (v/v) formaldehyde in the end. The mixture was incubated for 5-7 days at 37° C.

Vaccine preparable according to this method can e.g. be used for the prophylaxis and treatment of trichophytosis in cattle.

EXAMPLE 46

A solution of biological material containing in its structure a linear polysaccharide of N-acetyl-1,4-β-D-glucopyranosamine modified by 0.2% of paraaminobenzoic acid was added to the vaccine Polivac-TM against dermatophytosis of animals (manufacturer: "Vetbiochim" LLC, Moscow; Distributor: "Prostore" LLC, Moscow) to reach a final concentration of 0.3% (w/v). The pH of the solution was about 5.6. The concentration of microconidia was 40 million per ml.

Vaccine preparable according to this method can be used for the prophylaxis and treatment of dermatophytosis in animals.

EXAMPLE 47

*Candida albicans* DSM-9456 was cultivated on Agar plates as described in EP 0564620. One preferred medium was for example malt extract agar from Oxoid. The resulting fungal biomass was lifted off and treated with an aqueous solution of NaOH with a concentration of 3% (w/v). Alkaline treatment was performed at 80° C. for 6 h. Following the processing under aqueous alkaline conditions, the solid and liquid phases of the preparation were separated by centrifugation at 3500 g. After the alkaline treatment, the resulting supernatant was treated under acidic aqueous conditions, e.g. 50% acetic acid at pH 4.0 for 2 hours at a temperature of 4° to 8° C., whereafter separation of the solid and liquid layers took place. Then, the supernatant from the separation step was subjected to a precipitation step. A ratio of one volume supernatant to 3 volumes of alcohol resulted in good precipitation of the antigenic material. Finally the ASMP preparation was lyophilised.

A solution of biological material containing in its structure a linear polysaccharide of N-acetyl-1,4-β-D-glucopyranosamine modified by 0.5% of paraaminobenzoic acid was added to the vaccine Polivac-TM against dermatophytosis of animals (manufacturer: "Vethiochim" LLC, Moscow; Distributor: "Prostore" LLC, Moscow) to reach a final concentration of 0.3% (w/v). The pH of the solution was about 5.8. The concentration of microconidia was 40 million per ml. Finally the solid phase of ASMP was mixed with modified vaccine Polivac-TM. The concentration of ASMP was adjusted to 400 μg per ml.

Vaccine preparable according to this method can e.g. be used for the prophylaxis and treatment of dermatophytosis in animals.

EXAMPLE 48

Keratinase Pure 70 produced by PROTEOS Biotech, 14 Almansa Street, 02006 Albacete, Spain was used to prepare a solution containing 2 U/ml. *Candida albicans* DSM-9456 was cultivated on Agar plates as described in EP 0564620. One preferred medium was for example malt extract agar from Oxoid. The resulting fungal biomass was lifted off and treated with an aqueous solution of NaOH with concentrations of 3% (w/v). Alkaline treatment was performed at 80° C. for 6 h. Following the processing under aqueous alkaline conditions, the solid and liquid phases of the preparation were separated by centrifugation at 3500 g. After the alkaline treatment, the resulting supernatant was treated under acidic aqueous conditions, e.g. 50% acetic acid at pH 4.0 for 2 hours at temperatures of 4° to 8° C., whereafter separation of the solid and liquid layers took place. Then, the supernatant from the separation step was subjected to a precipitation step. A ratio of one volume supernatant to 3 volumes of alcohol resulted in good precipitation of the antigenic material. Finally the ASMP preparation was lyophilised.

The solution of Keratinase Pure 70 was mixed in an aqueous solution (for example 100-500 ml) of 0.3% solution of biological material contained in its structure a linear polysaccharide of N-acetyl-1,4-β-D-glucopyranosamine modified of paraaminobenzoic acid prepared according to example 8 (First stage). The concentration of Keratinase Pure 70 was adjusted to 1-1.2 U per ml. Formalin was added to reach 0.2% (v/v) in end suspension. The mixture was incubated for 5-7 days at 37° C. Finally the solid phase of ASMP was lifted off and homogenised in an aqueous suspension of modified linear polysaccharide of N-acetyl-1,4-f3-D-glucopyranosamine. The concentration of ASMP was adjusted to 200 μg per ml.

Vaccine preparable according to this method can e.g. be used for the prophylaxis and treatment of dermatophytosis in animals.

EXAMPLE 49

Dermatophyte culture of the species *Microsporum canis* BINO 483 was cultivated on agar/wort, for example in 3-10 Roux flasks for 21 day at 26-28° C. Suspension of the microconidia was cultivated in media with keratin and dermatophytes exoantigens were obtained according to RF patent No 2219945 as follows: The obtained suspension with concentration of microconidia of $40 \times 10^6$ to $50 \times 10^6$ was cultivated for 7 days under stirring at a temperature of 29° C. Subsequently, formalin was added to obtain an end concentration of 0.4%. The liquid phase was separated by three steps of filtration—through a metal grid with a cell of 200 μm-300 μm, than through Whatman paper filter No. 4 (size 20 μm to 25 μm) and in end through nylon filter for sterilisation with size 0.22 μm, but in the process of formalin preservation surprisingly found increased antigenic activity of the fractions obtained (AEMP). The dermatophytes exoantigens AEMP were lifted off and homogenised in an aqueous solution (for example 100-500 ml) of 0.2% solution of biological material contained in its structure a linear polysaccharide of N-acetyl-1,4-β-D-glucopyranosamine modified of paraaminobenzoic acid according to example 8. The concentration of AEMP was adjusted to 1-1.2 U per ml. Formalin was added to reach 0.2% (v/v) in the end suspension. The mixture was incubated for 5-7 days at 37° C.

Vaccine preparable according to this method can e.g. be used for the prophylaxis and treatment of dermatophytosis in animals.

EXAMPLE 50

Fungi culture of the species Chrisporium *tropicum* DSM-28405 was cultivated on agar/wort, for example in 3-10 Roux flasks for 21 days at 26-28° C. Subsequently, the obtained suspension of microconidia was cultivated in media with keratin and exoantigens were prepared according to RF patent No 2219945 as follows: The obtained suspension with a concentration of microconidia of $50 \times 10^6$ to $60 \times 10^6$ was cultivated for 7 days under stirring at a temperature of 30° C. Then, formalin in end concentration of 0.4% was added. The liquid phase was separated by three steps of filtration—through a metal grid with a cell of 200 μm-300 μm, than through Whatman paper filter No. 4 (size 20 μm to 25 μm) and in end through nylon filter for sterilisation with size 0.22 μm, but in the process of formalin preservation surprisingly found increased antigenic activity of the fractions of exoantigens (AEMP). The soluble exoantigens of fungi AEMP were lifted off and homogenised in an aqueous solution (for example 100-500 ml) of 0.2% solution of biological material contained in its structure a linear polysaccharide of N-acetyl-1,4-β-D-glucopyranosamine modified of paraaminobenzoic acid according to example 8. The concentration of AEMP was adjusted to 1-1.2 U per ml. Formalin was added to reach 0.2% (v/v) in end suspension. The mixture was incubated for 5-7 days at 37° C.

Vaccine preparable according to this method can e.g. be used for the treatment of dermatophytosis and allergic diseases in animals.

EXAMPLE 51

Dermatophyte culture of the species *Trichophyton verrucosum* DSM-28406 was cultivated on agar/wort, for example in 3-10 Roux flasks. The culture was cultivated for 15-30 days at 26-28° C. The fungal masses of the dermatophyte were lifted off and homogenised in an aqueous solution (for example 100-500 ml) of 0.2% solution of biological material contained in its structure a linear polysaccharide of N-acetyl-1,4-β-D-glucopyranosamine modified by valeric acid chloride according to example 6. The concentration of microconidia was adjusted to 250-300 thousand per ml. The homogenates were inactivated by adding formaldehyde directly to the cell suspension to reach 0.2% (v/v) in end. The mixture was incubated for 5-7 days at 37° C.

Vaccine preparable according to this method can e.g. be used for the prophylaxis and treatment of interdigital and/or digital dermatitis and/or interdigital phlegmon in animals.

EXAMPLE 52

Dermatophyte culture of the species *Trichophyton mentagrophytes* DSM-7279 was cultivated on agar/wort, for example in 3-10 Roux flasks. The culture was cultivated for 15-30 days at 26-28° C. The fungal masses of the dermatophyte were lifted off and homogenised in an aqueous solution (for example 100-500 ml) of 0.2% solution of biological material contained in its structure a linear polysaccharide of N-acetyl-1,4-β-D-glucopyranosamine modified of paraaminobenzoic acid according to example 8. The concentration of microconidia was adjusted to 250-300 thousand per ml. The homogenates were inactivated by adding formaldehyde to reach 0.2% (v/v) in end directly to the cell suspension. The mixture was incubated for 5-7 days at 37° C. Vaccine preparable according to this method can e.g. be used for the prophylaxis and treatment of interdigital and/or digital dermatitis and/or interdigital phlegmon in animals.

EXAMPLE 53

Dermatophyte culture of the species *Trichophyton verrucosum* DSM-28406 was cultivated on agar/wort, for example in 3-10 Roux flasks. The culture was cultivated for 15-30 days at 26-28° C. The fungal masses of the dermatophyte were lifted off and homogenised in an aqueous solution (for example 100-500 ml) of 0.2% solution of biological material contained in its structure a linear polysaccharide of N-acetyl-1,4-β-D-glucopyranosamine modified by glucuronic acid according to example 9. The concentration of microconidia was adjusted to 250-300 thousand per ml. The homogenates were inactivated by adding formaldehyde directly to the cell suspension to reach 0.1% (v/v) in end. The mixture was incubated for 5-7 days at 37° C.

Vaccine preparable according to this method can e.g. be used for the prophylaxis and treatment of interdigital and/or digital dermatitis and/or interdigital phlegmon in animals.

EXAMPLE 54

The first stage. Chitosan with a deacetylation of 67%-72%, a viscosity of 151-350 mPas and a molecular weight of 150-300 kDa was used as raw material. 40 grams of the polysaccharide was sterilized by autoclaving and 3.9 liters of 0.2% paraaminobenzoic acid in water for injection were added under stirring. To obtain the gel suspension 4N hydrochloric acid solution was added under stirring until getting a pH of 5.6. The final volume was adjusted with water for injection to 4 liters. Suspended polysaccharide was stirred in a sterile container for 72 hours until a gel suspension was obtained. Unsolved particles were removed by filtration through a metal grid with a cell of 200 μm-300 μm. *Candida albicans* DSM-9456 was cultivated on Agar plates as described in EP 0564620. One preferred medium was for example malt extract agar from Oxoid. The resulting fungal biomass was lifted off and treated with an aqueous solution of NaOH with a concentration of 3% (w/v). Alkaline treatment was performed at 80° C. for 6 h. Following the processing under aqueous alkaline conditions, the solid and liquid phases of the preparation were separated by centrifugation at 3500 g. After the alkaline treatment, the resulting supernatant was treated under acidic aqueous conditions, e.g. 50% acetic acid at pH 4.0 for 2 hours at a temperature of 4° to 8° C., whereafter separation of the solid and liquid layers took place. Then, the supernatant from the separation step was subjected to a precipitation step. The precipitation was performed by adding ethanol. A ratio of one volume supernatant to 3 volumes of alcohol resulted in good precipitation of the antigenic material. Finally the ASMP preparation was lyophilised. The solid phase was lifted off and homogenised in the product obtained according to example 6, but with the following difference in the second stage: The second stage. For obtaining the final product 0.3 liters of the modified polysaccharide were adjusted to a volume of 2.5 liters by adding sterile water for injection under stirring. Then 500 ml of thiomersal solution containing 0.24 grams of the active ingredient were added to the mixture. The resulting suspension was adjusted to a volume of 6 liters. The concentration of ASMP was adjusted to 100 μg per ml.

Vaccine preparable according to this method can e.g. be used for the prophylaxis and treatment of allergies.

EXAMPLE 55

An analysis for the presence of glucans was carried out.

Test Description

The 1,3-ß-D-analyses (Cape Cod, USA). The test was performed as described in the manufacturer's Glucan content in antigen samples was determined using the CE-marked Fungitell® assay for serum Instructions. In brief, the test is a protease zymogen-based colorimetric assay and makes use of a modification of the Limulus Amebocyte Lysate (LAL) pathway. The Fungitell reagent is modified to eliminate Factor C and, thus, to only react with 1,3-ß-D-Glucan. Unknown samples are mixed with the assay reagent and the mean rate of optical density change is calculated for all datapoints over an interval of 40 min. By comparison to an in parallel generated Standard curve, the amount of 1,3-ß-D-Glucan in the samples can be calculated.

Test Solutions of the antigens No. 1-13 were prepared in sterile ddH$_2$O and, subsequently, further dilutions were prepared in pyrogen-free LAL reagent grade water. Based on the results of the endotoxin testing, the highest dilution with detectable gel-clotting and one dilution above and below were measured in the Fungitell assay. Each sample was measured in duplicate in a 20 sec interval in a total of 40 min.

Test Results

For Standard curve generation 1,3-ß-D-Glucan Solutions of 100 pg/ml, 50 pg/ml, 25 pg/ml, 12.5 pg/ml and 6.25 pg/ml were prepared as recommended by the manufacturer (FIG. 1). The measured curve was linear over the entire range and meets the quality control acceptance criteria ($R^2 > 0.980$). The standard curve is shown in FIG. 1.

TABLE 1

On the basis of above shown curve the following 1,3-β-D-Glucan contents were detected in the test Solutions of analyzed samples:

| No. | Example | 1,3-β-D-Glucan content | Analyzed dilutions based on the test Solution |
|---|---|---|---|
| 1 | 1 | 115 ng/ml | 1:100, 1:1000, 1:10,000 |
| 2 | 2 | 133 ng/ml | 1:100, 1:1000, 1:10,000 |
| 3 | 3 | 123 ng/ml | 1:100, 1:1000, 1:10,000 |
| 4 | 4 | 110 ng/ml | 1:100, 1:1000, 1:10,000 |
| 5 | 7 | 45 pg/ml | 1:10, 1:100, 1:1000 |
| 6 | 20 | 55 pg/ml | 1:10, 1:100, 1:1000 |
| 7 | 18 | 25 pg/ml | 1:10, 1:100, 1:1000 |
| 8 | 20 | 21 pg/ml | 1:10, 1:100, 1:1000 |
| 9 | 26 | 50 pg/ml | 1:10, 1:100, 1:1000 |
| 10 | 27 | 70 pg/ml | 1:10, 1:100, 1:1000 |
| 11 | 28 | 110 pg/ml | 1:10, 1:100, 1:1000 |
| 12 | 29 | 90 pg/ml | 1:10, 1:100, 1:1000 |
| 13 | 30 | 120 pg/ml | 1:10, 1:100, 1:1000 |
| 14 | 31 | 132 pg/ml | 1:10, 1:100, 1:1000 | mg > μg > ng > pg

EXAMPLE 56

An analysis for the presence of endotoxins was carried out.

Endotoxin content in antigen samples was determined using the gel-clot method according to EP 2.6.14.

Test Solutions of the antigens No. 1-7 were prepared in sterile $H_2O$ and, subsequently, dilutions from 1:10 to 1:10,000,000 were prepared in pyrogen-free LAL reagent grade water. The dilutions were measured in duplicate and endotoxin concentration was calculated using the following formula:

Endotoxin concentration=0.06 IU/ml×dilution factor with at least one gel-clot formation The semi-quantitative assay has a LAL-sensitivity of 0.061 U/ml. Results shown in table 4

Test Results

TABLE 2

| No. | Example | Endotoxin content [IU/ml] | Highest dilution factor with gel-clot formation |
|---|---|---|---|
| 1 | 1 | 60-600 | 1:1000 |
| 2 | 2 | 60-600 | 1:1000 |
| 3 | 3 | 60-600 | 1:1000 |
| 4 | 4 | 60-600 | 1:1000 |
| 5 | 7 | 0.06-6 | <1:100 |
| 6 | 20 | 60-600 | 1:1000 |
| 7 | 18 | 6-60 | 1:100 |
| 8 | 20 | 0.06-6 | <1:100 |
| 9 | 26 | 0.06-6 | <1:100 |
| 10 | 27 | 0.06-6 | <1:100 |
| 11 | 28 | 0.06-6 | <1:100 |
| 12 | 29 | 0.06-6 | <1:100 |
| 13 | 30 | 0.06-6 | <1:100 |
| 14 | 31 | 0.06-6 | <1:100 |

IU, International (endotoxin) units

EXAMPLE 57

An analysis for the antimicrobial activity was carried out.

Test Description

The antimicrobial activity of compounds was analyzed by the "Test for efficacy of antimicrobial preservation" according to the following procedure. To count the viable microorganisms in the inoculated products, the agar medium used for the initial cultivation of the respective microorganisms was used. A series of containers of the product to be examined was inoculated, each with a suspension of one of the test organisms to give an inoculum of $10^5$ to $10^6$ microorganisms per millilitre or per gram of the preparation. The volume of the suspension of inoculum did not exceed 1 per cent of the volume of the product. To ensure homogeneous distribution it was thoroughly mixed. The inoculated product was maintained at 20-25° C., protected from light. A suitable sample was removed from each container, typically 1 mL or 1 g, at zero hour and at appropriate intervals according to the type of the product and the number of viable microorganisms was determined by plate count or membrane filtration (2.6.12). It was ensured that any residual antimicrobial activity of the product was eliminated by dilution, by filtration or by the use of a specific inactivator. When dilution procedures was used, due allowance was made for the reduced sensitivity in the recovery of small numbers of viable microorganisms. When a specific inactivator was used, the ability of the system to support the growth of the test organisms was confirmed by the use of appropriate controls. The procedure was validated to verify its ability to demonstrate the required reduction in count of viable microorganisms.

In brief, 4×10 ml of test Solution (prepared with $ddH_2O$) were inoculated each with 0.1 ml (1% v/v) of the test-microorganisms *Pseudomonas aeruginosa, Staphylococcus aureus, Candida albicans* and *Aspergillus brasiliensis*. 6 hpi (hours post inoculation), 24 hpi, 7 dpi (days post inoculation) and 14 dpi samples were drawn and numbers of viable microorganisms were determined by plating a dilution series on agar plates. The elimination of putative residual antimicrobial activity of the test Compounds by dilution was proofed prior to test Performance.

TABLE 3

| Time | Micro-organism | Compound according to Example 6 | Compound according to Example 8 | Compound according to Example 15 |
|---|---|---|---|---|
| | | Recovered viable microorganisms and reduction factors in $\log_{10}$ [cfu/ml] | | |
| 0 hpi | P.a. | 2.00 | 2.30 | 2.40 |
| | S.a. | 3.97 | 4.30 | 4.50 |
| | C.a. | 5.18 | 4.82 | 4.95 |
| | A.b. | 5.79 | 5.72 | 5.79 |
| 6 hpi | P.a. | 0.00 (2.00) | 0.00 (2.30) | 0.00 (2.30) |
| | S.a. | 0.00 (3.97) | 2.74 (1.56) | 0.00 (2.30) |
| | C.a. | 3.04 (2.14) | 0.00 (4.82) | 0.00 (4.82) |
| | A.b. | 5.70 (0.09) | 5.61 (0.11) | 5.61 (0.11) |
| 24 hpi | P.a. | 0.00 (2.00) | 0.00 (2.30) | 0.00 (2.30) |
| | S.a. | 1.20 (2.77) | 1.82 (2.48) | 1.82 (2.48) |
| | C.a. | 0.00 (5.18) | 0.00 (4.82) | 0.00 (4.82) |
| | A.b. | 5.70 (0.09) | 5.75 (−0.03) | 5.75 (−0.03) |
| 7 dpi | P.a. | 0.00 (2.00) | 0.00 (2.30) | 0.00 (2.30) |
| | S.a. | 0.00 (3.97) | 0.00 (4.30) | 0.00 (4.30) |
| | C.a. | 0.00 (5.18) | 0.00 (4.82) | 0.00 (4.82) |
| | A.b. | 5.82 (−0.03) | 5.83 (−0.11) | 5.83 (−0.11) |
| 14 dpi | P.a. | 0.00 (2.00) | 0.00 (2.30) | 0.00 (2.30) |
| | S.a. | 0.00 (3.97) | 0.00 (4.30) | 0.00 (4.30) |

TABLE 3-continued

| Time | Micro-organism | Compound according to Example 6 | Compound according to Example 8 | Compound according to Example 15 |
|---|---|---|---|---|
| | C.a. | 0.00 (5.18) | 0.00 (4.82) | 0.00 (4.82) |
| | A.b. | 5.89 (−0.10) | 5.72 (0.00) | 5.72 (0.00) |

P.a., *Pseudomonas aeruginosa*;
S.a., *Staphylococcus aureus*;
C.a., *Candida albicans*;
A.b., *Aspergillus brasiliensis*;
reduction factors in relation to 0 hpi are indicated in brackets.

EXAMPLE 58

Cows with latent (subclinical) mastitis were treated. The diagnosis was made by a usual procedure with 2% solution of mastidin. The animals were divided into 13 groups with 6 animals in each group. All groups of cows were treated by 10 ml of the preparation intracisternally twice with an interval of 24 hours. All the animals were re-tested with a 2% solution of mastidin by the standard procedure on day 7 and day 14.

The results are shown in Table 4.

| No. of group | No. of example | No. of animals | Frequency of drug administration | Amount of healthy animals on day 7 after the last administration | Amount of healthy animals in day 14 after the last administration |
|---|---|---|---|---|---|
| 1 | 1 | 6 | 2 | 3 | 4 |
| 2 | 2 | 6 | 2 | 4 | 4 |
| 3 | 3 | 6 | 2 | 3 | 3 |
| 4 | 4 | 6 | 2 | 3 | 3 |
| 5 | 5 | 6 | 2 | 3 | 3 |
| 6 | 6 | 6 | 2 | 4 | 3 |
| 7 | 7 | 6 | 2 | 4 | 4 |
| 8 | 8 | 6 | 2 | 4 | 4 |
| 9 | 9 | 6 | 2 | 4 | 4 |
| 10 | 10 | 6 | 2 | 4 | 4 |
| 11 | 11 | 6 | 2 | 4 | 4 |
| 12 | 12 | 6 | 2 | 4 | 4 |
| 13 | 16 | 6 | 2 | 4 | 4 |

EXAMPLE 59

Cows with latent (subclinical) mastitis were treated. The diagnosis was made by a usual procedure with 2% solution of mastidin. The animals were divided into 14 groups with 10 animals in each group. All groups of cows were treated by 10 ml of the preparation intracisternally thrice with an interval of 24 hours. All the animals were re-tested with a 2% solution of mastidin by the standard procedure on day 5.

The results are shown in Table 5.

| No. of group | No. of example | No. of animals | Frequency of drug administration | Amount of healthy animals on day 5 after the last administration |
|---|---|---|---|---|
| 1 | 8 | 10 | 3 | 6 |
| 2 | 13 | 10 | 3 | 6 |
| 3 | 14 | 10 | 3 | 5 |
| 4 | 16 | 10 | 3 | 8 |
| 5 | 17 | 10 | 3 | 5 |
| 6 | 18 | 10 | 3 | 6 |
| 7 | 19 | 10 | 3 | 5 |
| 8 | 20 | 10 | 3 | 6 |
| 9 | 25 | 10 | 3 | 8 |
| 10 | 26 | 10 | 3 | 6 |
| 11 | 27 | 10 | 3 | 6 |
| 12 | 32 | 10 | 3 | 10 |
| 13 | 33 | 10 | 3 | 10 |
| 14 | 34 | 10 | 3 | 10 |

EXAMPLE 60

Cows with latent (subclinical), clinical mastitis and purulent-catarrhal endometritis were treated. The diagnosis was made by a usual procedure with 5% solution of dimastin for mastitis and clinical symptoms for endometritis. All cows were administered by 10 ml of the preparation manufactured according to example 13 intracisternally or intrauterine twice or trice with the interval of 24 hours. All the animals were re-tested with a 5% solution of dimastin by the standard procedure and clinical observation on day 7.

The results are shown in Table 6.

| No. | Identification (Id) no. of animal | Disease | Frequency of drug administration | on day 7 after the last administration |
|---|---|---|---|---|
| 1 | 2273 | Clinical mastitis | 3 | Recovery |
| 2 | 2547 | Clinical mastitis | 2 | Recovery |
| 3 | 2234 | Clinical mastitis | 3 | Recovery |
| 4 | 2451 | Latent mastitis | 3 | Recovery |
| 5 | 2664 | Latent mastitis | 3 | Recovery and relapse on day 5 |
| 6 | 2510 | Latent mastitis | 3 | Recovery |
| 7 | 2523 | Purulent-catarrhal endometritis | 3 | Recovery |
| 8 | 2653 | Latent mastitis | 3 | Recovery |
| 9 | 2463 | Latent mastitis | 3 | Recovery |

EXAMPLE 61

Cows with latent (subclinical) mastitis were treated. The diagnosis was made by a usual procedure with 5% solution of dimastin for mastitis and clinical symptoms for endometritis. All cows were administered by 10 ml of the preparation manufactured according to example 26 intracisternally or intrauterine twice or trice with the interval of 24 hours. All the animals were re-tested with a 5% solution of dimastin by the standard procedure and clinical observation on day 7.

The results are shown in Table 7.

| Id no. of animal | Disease | Frequency of drug administration | on day 1 after the last administration |
|---|---|---|---|
| 1201 | Latent mastitis | 3 | Latent mastitis |
| 9262 | Latent mastitis | 3 | Recovery |
| 1180 | Latent mastitis | 3 | Recovery |
| 5324 | Latent mastitis | 3 | Latent mastitis |
| 1101 | Latent mastitis | 3 | Recovery |
| 1363 | Latent mastitis | 3 | Latent mastitis |
| 9249 | Latent mastitis | 3 | Recovery |

-continued

| Id no. of animal | Disease | Frequency of drug administration | on day 1 after the last administration |
|---|---|---|---|
| 9210 | Latent mastitis | 3 | Recovery |
| 7250 | Latent mastitis | 3 | Latent mastitis |
| 0127 | Latent mastitis | 3 | Recovery |

Thus, the obtained immunobiological preparation makes possible treatment of mastitis of cows, which can be widely used in controlling of this widespread disease.

EXAMPLE 62

Cows with latent (subclinical) mastitis were treated. The diagnosis was made by a usual procedure with 5% solution of dimastin for mastitis and clinical symptoms for endometritis. All cows were administered by 10 ml of the preparation manufactured according to example 26 intracisternally or intrauterine twice or trice with the interval of 24 hours. All the animals were re-tested with a 5% solution of dimastin by the standard procedure and clinical observation on day 7. 59% of animals were recovered after treatment.

The results are shown in Table 8.

| Disease | Number of quarters of udder with mastitis | Frequency of drug administration | on day 1 after the last administration |
|---|---|---|---|
| Latent mastitis | 1 | 3 | Recovery |
| Latent mastitis | 2 | 3 | Recovery |
| Latent mastitis | 1 | 3 | Latent mastitis |
| Latent mastitis | 2 | 3 | Latent mastitis |

EXAMPLE 63

Cows with clinical evidence of lameness, lesions of the interdigital space, which are typical for DD, ID and IP, were treated with various drugs. Therapeutic application of vaccine: 3 times with an interval of 7 days with a dose of 5 ml. Vaccine was prepared according to examples 45, 40 and 6.

Clinical Manifestation of Disease:
+ Recovering, or gray, no pain
++ in healing, <2 cm, yellow, light pain
+++ lesions >2 cm, yellow, moderate pain
++++ acute disease >2 cm, red, significant pain The result are shown in Table 9.

| № of group | № of example | № of animals/ clinical manifes- tation | Frequency of drug administra- tion | Amount of healthy animals | |
|---|---|---|---|---|---|
| | | | | In 30-35 days after the first application | In 53-55 days after the first application |
| 1 | 45 | 10/ 6++ 4+++ | 3 | 10 | 10 |
| 2 | 40 | 10/ 5++ 4+++ 1++++ | 3 | 10 | 10 |
| 3 | 6 | 10/ 7++ 3+++ | 3 | 10 | 10 |

No common and local reaction after application was observed. Efficacy of vaccination was about 100%.

EXAMPLE 64

Cows with clinical evidence of lameness, lesions of the interdigital space, which are typical for DD, ID and IP, were treated with various drugs. Therapeutic application of vaccine: 3 times with an interval of 10 days of vaccine prepared according to example 45.

Clinical Manifestation of Disease:
+ Recovering, or gray, no pain
++ in healing, <2 cm, yellow, light pain
+++ lesions >2 cm, yellow, moderate pain
++++ acute disease >2 cm, red, significant pain The results are shown in Table 10.

| № of group | Amount of animals | № of animals with clinical manifes- tation | Frequency of drug administra- tion/dose | Amount of animals with clinical manifestation | |
|---|---|---|---|---|---|
| | | | | In 33 days after the first application | In 60 days after the first application |
| 1 | 17 | 5++ 12++++ | 3/5 ml | 11/+ 7/++ | 17/+ |
| 2 | 23 | 7++ 8+++ 8++++ | 3/2.5 ml | 9/+ 5/++ 9/+++ | 23/+ |

No common and local reaction after application was observed. Efficacy of vaccination was about 80-100% after application of vaccine in a dose of 5 ml.

EXAMPLE 65

Cows with clinical evidence of lameness, lesions of the interdigital space, which are typical for DD, ID and IP, were treated with various drugs. Therapeutic application of vaccine: 3 times with an interval of 10 days of vaccine prepared according to example 45.

Clinical Manifestation of Disease:
+ Recovering, or gray, no pain
++ in healing, <2 cm, yellow, light pain
+++ lesions >2 cm, yellow, moderate pain
++++ acute disease >2 cm, red, significant pain The results are shown in Table 11.

| № of group | Amount of animals | № of animals with clinical manifestation | Frequency of drug administration/ dose | Amount of animals with clinical manifestation In 51 days after the first application |
|---|---|---|---|---|
| 1 | 19 | 19++++ | 3/5 ml | 5/+ 7/++ 5/+++ 2 - culled for slaughter |

-continued

| № of group | Amount of animals | № of animals with clinical manifestation | Frequency of drug administration/ dose | Amount of animals with clinical manifestation In 51 days after the first application |
|---|---|---|---|---|
| 2 | 18 | 18++++ | 3/3.0 ml | 1/+ |
|   |   |   |   | 4/++ |
|   |   |   |   | 6/+++ |
|   |   |   |   | 2/++++ |
|   |   |   |   | 5 - culled for slaughter |

No common and local reaction after application was observed. Efficacy of vaccination was about 60-63% after application of vaccine in dose 5 ml.

EXAMPLE 66

Cows with clinical evidence of lameness, lesions of the interdigital space, which are typical for DD, ID and IP, were treated with various drugs. Therapeutic application of vaccine: 3 times with an interval of 7 days in a dose of 5 ml. Vaccine was prepared according to examples 38, 39, 40 and 44.

Clinical Manifestation of Disease:

+ Recovering, or gray, no pain
++ in healing, <2 cm, yellow, light pain
+++ lesions >2 cm, yellow, moderate pain
++++ acute disease >2 cm, red, significant pain The results are shown in Table 12.

| № of group | № of example | № of animals/ clinical manifes- tation | Frequency of drug administra- tion | Amount of healthy animals In 30-35 days after the first application | Amount of healthy animals In 53-55 days after the first application |
|---|---|---|---|---|---|
| 1 | 38 | 10/ | 3 | 5/+ | 7/+ |
|   |   | 5++ |   | 5/++ | 3/++ |
|   |   | 5+++ |   |   |   |
| 2 | 39 | 10/ | 3 | 6/+ | 6/+ |
|   |   | 5++ |   | 4/++ | 4/++ |
|   |   | 5+++ |   |   |   |
| 3 | 40 | 10/ | 3 | 5/+ | 7/+ |
|   |   | 6++ |   | 5/++ | 3/++ |
|   |   | 4+++ |   |   |   |
| 4 | 44 | 10/ | 3 | 4/+ | 6/+ |
|   |   | 4++ |   | 5/++ | 4/++ |
|   |   | 6+++ |   | 1/+++ |   |

No common and local reaction after application was observed. Efficacy of vaccination was about 60% to 70% in all groups vaccinates.

EXAMPLE 67

Cows with clinical evidence of lameness, lesions of the interdigital space, which are typical for DD, ID and IP, were treated with various drugs. Therapeutic application of vaccine: 3 times, 0.4 ml intracutaneous with an interval of 7 days. Vaccine was prepared according to examples 51 and 52.

Clinical Manifestation of Disease:

+ Recovering, or gray, no pain
++ in healing, <2 cm, yellow, light pain
+++ lesions >2 cm, yellow, moderate pain
++++ acute disease >2 cm, red, significant pain The results are shown in Table 13.

| № of group | № of example | № of animals/ clinical manifes- tation | Frequency of drug adminis- tration | Amount of healthy animals In 35-40 days after the first application | Amount of healthy animals In 55-60 days after the first application |
|---|---|---|---|---|---|
| 1 | 51 | 100/ | 3 | 50/+ | 70/+ |
|   |   | 50++ |   | 50/++ | 30/++ |
|   |   | 50+++ |   |   |   |
| 2 | 52 | 100/ | 3 | 60/+ | 60/+ |
|   |   | 50++ |   | 40/++ | 40/++ |
|   |   | 50+++ |   |   |   |

No common and local reaction after application was observed. Efficacy of vaccination was about 60% to 70% in all groups vaccinates.

EXAMPLE 68

Dose titration study. Vaccination of cows against DD, ID and IP was done. Prophylactic application of vaccine: 2 times with an interval of 10 days of vaccine prepared according to example 6.

Clinical Manifestation of Disease were Investigated:

+ Recovering, or gray, no pain
++ in healing, <2 cm, yellow, light pain
+++ lesions >2 cm, yellow, moderate pain
++++ acute disease >2 cm, red, significant pain The results are shown in Table 14.

| 73 days after application | | |
|---|---|---|
| Dose 1 ml 100 animals | Dose 2.5 ml 100 animals | Control 215 animals |
| 7 animals+ | 7 animals+ | 21 animals+ |
|   |   | 18 animals++ |
|   |   | 6 animals+++ |

No common and local reactions after application of vaccine were observed. Efficacy of vaccination with doses 1 ml and 2.5 ml in this time was about 93%. 45 animals (about 21%) from control group were with clinical symptoms of DD, ID and IP.

The results are shown in Table 15.

| 107 days after application of vaccine | | |
|---|---|---|
| Dose 1 ml 100 animals | Dose 2.5 ml 100 animals | Control 215 animals |
| 7 animals+ | 9 animals+ | 11 animals+ |
|   |   | 12 animals++ |
| 4 animals - culled for slaughter | 4 animals - culled for slaughter | 9 animals+++ |
|   |   | 27 animals - culled for slaughter |

Efficacy of vaccination with doses 1 ml and 2.5 ml in this time was about 87%-89%. 59 animals (about 27%) from control group were with clinical symptoms of DD, ID and IP.

The results are shown in Table 16.

| 170 days after application of vaccine | | |
|---|---|---|
| Dose 1 ml 100 animals | Dose 2.5 ml 100 animals | Control 215 animals |
| 25 animals+ | 41 animals+ | 112 animals+ |
| Additional 6 animals - culled for slaughter | Additional 3 animals - culled for slaughter | Additional 42 animals - culled for slaughter |

Efficacy of vaccination with doses 1 ml was about 70% and 2.5 ml was about 53%. 154 animals (about 72%) from control group were with clinical symptoms of DD, ID and IP.

This investigation demonstrate prophylactic vaccination of animals with dose 1.0 ml. Duration of immunity was about 5.5 month.

EXAMPLE 69

Vaccination of cows against DD, ID and IP was done. Prophylactic application of vaccine: 3 times intracutaneous with a dose of 0.4 ml in an interval of 10 days of vaccine prepared according to example 51.
Summary of Investigation:
Animals In-Group 1 were Vaccinated
Observation Before Vaccination

| | |
|---|---|
| Amount of animals/clinical manifestations of DD, ID and IP | 200/100 |

In 160 to 175 Days after Last Vaccination

| | |
|---|---|
| Amount of animals/amount of limbs with lameness | 200/20 |
| Amount of healthy animals | 180 |
| Efficacy of vaccination | 90% |

Animals in Group 2 were not Vaccinated (Control)
Observation Before Vaccination

| | |
|---|---|
| Amount of animals/clinical manifestations of DD, ID and IP | 200/100 |

In 160 to 175 Days after Last Application of Placebo
Amount of Animals/Amount of Animals with Manifestations of

| | |
|---|---|
| Amount of animals/amount of animals with manifestations of Clinical symptoms of DD, ID and IP | 200/132 |
| Amount of healthy animals | 68 |
| Amount of ill animals during of observation time | 66% |

All animals with clinical symptom of diseases were treated with local application of aseptic medicine or antibiotics. In case of IP intramuscular injection of antibiotics were used.

EXAMPLE 70

Vaccination of cows against DD, ID and IP was done. Prophylactic application of vaccine: 3 times intracutaneous with dose 0.4 ml with an interval of 10 days of vaccine prepared according to example 52.
Summary of Investigation:
Animals In-Group 1 were Vaccinated
Observation Before Vaccination

| | |
|---|---|
| Amount of animals/clinical manifestations of DD, ID and IP | 150/80 |

In 160 to 190 Days after Last Vaccination

| | |
|---|---|
| Amount of animals/amount of limbs with lameness | 150/15 |
| Amount of healthy animals | 135 |
| Efficacy of vaccination | 90% |

Animals in Group 2 were not Vaccinated (Control)
Observation Before Vaccination

| | |
|---|---|
| Amount of animals/clinical manifestations of DD, ID and IP | 150/70 |

In 160 to 175 Days after Last Application of Placebo
Amount of Animals/Amount of Animals with Manifestations of

| | |
|---|---|
| Amount of animals/amount of animals with manifestations of Clinical symptoms of DD, ID and IP | 150/118 |
| Amount of healthy animals | 32 |
| Amount of ill animals during of observation time | 78.7% |

All animals with clinical symptom of diseases were treated with local application of aseptic medicine or antibiotics. In case of IP the intramuscular injection of antibiotics were used.

EXAMPLE 71

Efficacy of the vaccination after *Trichophyton* and *Microsporum* challenge in guinea pigs (this method was described in WO 98/15284).

The challenge of *Trichophyton mentagrophytes* and *Microsporum canis* microconidiae consisted of 100-200 thousand microconidia per $cm^2$ (300-600 thousand microconidia) applied topically to each animal. The challenge of *Trichophyton verrucosum* consisted of 500 thousand microconidia per $cm^2$ (1.5 million microconidia) applied topically to each animal. A single dose of 1.0 ml of the vaccine was applied by intramuscular injection on the same day as the challenge and a second dose after 7 days. The observation was continued for 4 weeks after the initial injection of the vaccine. Vaccines prepared according examples 38, 39, 46, 47, 48, 49, 50 (see tables 17-30) were tested.

A single dose of 1.0 ml of the vaccine was applied through intramuscular injection on the same day as the challenge and a second dose after 7 days. The observation was continued for 4 weeks after the initial injection of vaccine.
Suspension of Challenge Strain Cells
For infection of the animals, *Trichophyton verrucosum* (Tv) *Trichophyton mentagrophytes* (Tm), and *Microsporum canis* (Mc) were used as fungal pathogens. Data about these strains are shown below:

| | |
|---|---|
| 1. Species: | *Trichophyton verrucosum* |
| Strain number: | 1220 |
| Volume: | 0.5 ml |
| Infection dose (1000 cells): | 500-600/$cm^2$ |
| Area of skin for infection: | 2-4 cm |

| | |
|---|---|
| 2. Species: | *Trichophyton mentagrophytes* |
| Strain number: | 1440 |
| Volume: | 0.5 ml |
| Infection dose (1000 cells): | 100-200/$cm^2$ |
| Area of skin for infection: | 2-4 $cm^2$ |

| | |
|---|---|
| 3. Species: | *Microsporum canis* |
| Strain number: | 724 |
| Volume: | 0.5 ml |
| Infection dose (1000 cells): | 100-200/$cm^2$ |
| Area of skin for infection: | 2-4 $cm^2$ |

Evaluation of Fungal Infection

On the 7$^{th}$, 15$^{th}$, 22$^{nd}$, 29$^{th}$ and 36$^{th}$ day of the study, the animals were observed and clinical symptoms were evaluated on the basis of the following scoring system:

0=no symptoms
1=hyperemia of the skin in the area of fungal infection
2=single spots of scaling
3=scaling of the skin in the area of fungal infection
4=thin small crusts in the area of fungal infection
5=scab-like crusts in the area of fungal infection

| | TREATMENT SCHEME 1 | | | | |
|---|---|---|---|---|---|
| Group | Day 1 Vaccination Challenge | Day 15 Vaccination 1$^{st}$ observation | Day 22 2$^{nd}$ observation | Day 29 3$^{rd}$ observation | Day 36 4$^{th}$ observation |
| Example 38 | 1$^{st}$ injection of vaccine: intra-muscular 1 ml Challenge: application of fungus cell suspension on skin | 2$^{nd}$ injection of vaccine: intra-muscular 1 ml Assessment of clinical symptoms of *Trichophyton verrucosum* infection | | | |
| Example 39 | 1$^{st}$ injection of vaccine: intra-muscular 1 ml Challenge: application of fungus cell suspension on skin | 2$^{nd}$ injection of vaccine: intra-muscular 1 ml Assessment of clinical symptoms of *Trichophyton verrucosum* infection | | | |
| Example 50 | 1$^{st}$ injection of vaccine: intra-muscular 1 ml Challenge: application of fungus cell suspension on skin | 2$^{nd}$ injection of vaccine: intra-muscular 1 ml Assessment of clinical symptoms of *Trichophyton verrucosum* infection | | | |
| Control | 1$^{st}$ injection of solvent: intra-muscular 1 ml Challenge: application of fungus cell suspension on skin | 2$^{nd}$ injection of solvent: intra-muscular 1 ml Assessment of clinical symptoms of *Trichophyton verrucosum* infection | | | |

| | TREATMENT SCHEME 2 | | | | |
|---|---|---|---|---|---|
| Group | Day 1 Vaccination Challenge | Day 15 Vaccination 1$^{st}$ observation | Day 22 2$^{nd}$ observation | Day 29 3$^{rd}$ observation | Day 36 4$^{th}$ observation |
| Example 46 | 1$^{st}$ injection of vaccine: intra-muscular 1 ml Challenge: application of fungus cell suspension on skin | 2$^{nd}$ injection of vaccine: intra-muscular 1 ml Assessment of clinical symptoms of *Trichophyton mentagrophytes* infection | | | |
| Example 47 | 1$^{st}$ injection of vaccine: intra-muscular 1 ml Challenge: application of fungus cell suspension on skin | 2$^{nd}$ injection of vaccine: intra-muscular 1 ml Assessment of clinical symptoms of *Trichophyton mentagrophytes* infection | | | |

-continued

| | | TREATMENT SCHEME 2 | | | |
|---|---|---|---|---|---|
| Group | Day 1<br>Vaccination<br>Challenge | Day 15<br>Vaccination<br>$1^{st}$ observation | Day 22<br>$2^{nd}$<br>observation | Day 29<br>$3^{rd}$<br>observation | Day 36<br>$4^{th}$<br>observation |
| Example 50 | $1^{st}$ injection of vaccine: intra-muscular 1 ml<br>Challenge: application of fungus cell suspension on skin | $2^{nd}$ injection of vaccine: intra-muscular 1 ml<br>Assessment of clinical symptoms of *Trichophyton mentagrophytes* infection | | | |
| Control | $1^{st}$ injection of solvent: intra-muscular 1 ml<br>Challenge: application of fungus cell suspension on skin | $2^{nd}$ injection of solvent: intra-muscular 1 ml<br>Assessment of clinical symptoms of *Trichophyton mentagrophytes* infection | | | |

| | | TREATMENT SCHEME 3 | | | |
|---|---|---|---|---|---|
| Group | Day 1<br>Vaccination<br>Challenge | Day 15<br>Vaccination<br>$1^{st}$ observation | Day 22<br>$2^{nd}$<br>observation | Day 29<br>$3^{rd}$<br>observation | Day 36<br>$4^{th}$<br>observation |
| Example 48 | $1^{st}$ injection of vaccine: intra-muscular 1 ml<br>Challenge: application of fungus cell suspension on skin | $2^{nd}$ injection of vaccine: intra-muscular 1 ml<br>Assessment of clinical symptoms of *Trichophyton Microsporum canis* infection | | | |
| Example 49 | $1^{st}$ injection of vaccine: intra-muscular 1 ml<br>Challenge: application of fungus cell suspension on skin | $2^{nd}$ injection of vaccine: intra-muscular 1 ml<br>Assessment of clinical symptoms of *Microsporum canis* infection | | | |
| Example 50 | $1^{st}$ injection of vaccine: intra-muscular 1 ml<br>Challenge: application of fungus cell suspension on skin | $2^{nd}$ injection of vaccine: intra-muscular 1 ml<br>Assessment of clinical symptoms of *Microsporum canis* infection | | | |
| Control | $1^{st}$ injection of solvent: intra-muscular 1 ml<br>Challenge: application of fungus cell suspension on skin | $2^{nd}$ injection of solvent: intra-muscular 1 ml<br>Assessment of clinical symptoms of *Microsporum canis* infection | | | |

TABLE 17

Clinical symptoms of Trichophyton verrucosum disease in guinea pigs

| Vaccine prepared according to | | Date of observation | | | |
|---|---|---|---|---|---|
| | | Day 15 | Day 22 | Day 29 | Day 36 |
| Example 38 | mean | 2.2 | 3.4 | 1.4 | 0 |
| Example 39 | mean | 3.0 | 3.2 | 1.0 | 0 |
| Untreated control | mean | 2.4 | 4.0 | 4.0 | 2.2 |

The severity of clinical symptoms of *Trichophyton verrucosum* infection in challenged guinea pigs is shown after different observation periods. Compared with vaccinated animals unvaccinated control animals had more severe clinical symptoms in 29 and 36 day.

TABLE 18

Number of guinea pigs with clinical symptoms of Trichophyton verrucosum disease

| Group | Complex/Vaccine | Date of observation | | | |
|---|---|---|---|---|---|
| | | Day 15 | Day 22 | Day 29 | Day 36 |
| 1 | Example 38 | 3/5 | 5/5 | 3/5 | 0/5 |
| 2 | Example 39 | 3/5 | 5/5 | 1/5 | 0/5 |
| 3 | Untreated control | 4/5 | 5/5 | 5/5 | 4/5 |

Note:
number of animals with clinical symptoms/number of challenged

Compared with the control group the less vaccinated animals had clinical symptoms on days 29 and 36.

TABLE 19

Clinical symptoms of Trichophyton mentagrophytes disease in guinea pigs

| Vaccine prepared according to | | Date of observation | | | |
|---|---|---|---|---|---|
| | | Day 15 | Day 22 | Day 29 | Day 36 |
| Example 46 | mean | 3.0 | 3.2 | 1.6 | 0 |
| Example 47 | mean | 3.0 | 3.6 | 1.2 | 0 |
| Untreated control | mean | 4.0 | 4.8 | 3.8 | 2.0 |

The severity of clinical symptoms of *Trichophyton mentagrophytes* infection in challenged guinea pigs is shown after different observation periods. Compared with vaccinated animals unvaccinated control animals had more severe clinical symptoms in 29 and 36 day.

TABLE 20

Number of guinea pigs with clinical symptoms of Trichophyton mentagrophytes disease

| Group | Complex/Vaccine | Date of observation | | | |
|---|---|---|---|---|---|
| | | Day 15 | Day 22 | Day 29 | Day 36 |
| 1 | Example 46 | 5/5 | 5/5 | 5/5 | 0/5 |
| 2 | Example 47 | 5/5 | 5/5 | 3/5 | 0/5 |
| 3 | Untreated control | 5/5 | 5/5 | 5/5 | 4/4 |

(Note: number of animals with clinical symptoms/number of challenged)

Compared with the control group the less vaccinated animals had clinical symptoms on days 29 and 36.

TABLE 21

Clinical symptoms of Microsporum canis disease in guinea pigs

| Vaccine prepared according to | | Date of observation | | | |
|---|---|---|---|---|---|
| | | Day 15 | Day 22 | Day 29 | Day 36 |
| Example 46 | mean | 3.2 | 3.8 | 2.0 | 0.2 |
| Example 47 | mean | 3.2 | 3.4 | 1.8 | 0 |
| Untreated control | mean | 3.4 | 4.2 | 2.2 | 2.0 |

The severity of clinical symptoms of *Microsporum canis* infection in challenged guinea pigs is shown after different observation periods. Compared with vaccinated animals unvaccinated control animals had more severe clinical symptoms on day 36.

TABLE 22

Number of guinea pigs with clinical symptoms of Microsporum canis disease

| Group | Complex/Vaccine | Date of observation | | | |
|---|---|---|---|---|---|
| | | Day 15 | Day 22 | Day 29 | Day 36 |
| 1 | Example 46 | 5/5 | 5/5 | 4/5 | 1/5 |
| 2 | Example 47 | 5/5 | 5/5 | 4/5 | 0/5 |
| 3 | Untreated control | 5/5 | 5/5 | 4/5 | 4/5 |

(Note: number of animals with clinical symptoms/number of challenged)

Compared with the control group the less vaccinated animals had clinical symptoms on day 36.

TABLE 23

Clinical symptoms of Microsporum canis disease in guinea pigs

| Vaccine prepared according to | | Date of observation | | | |
|---|---|---|---|---|---|
| | | Day 15 | Day 22 | Day 29 | Day 36 |
| Example 48 | mean | 3.4 | 3.6 | 1.0 | 0 |
| Example 49 | mean | 3.0 | 3.2 | 1.6 | 0 |
| Untreated control | mean | 3.6 | 4.2 | 2.2 | 2.2 |

The severity of clinical symptoms of *Microsporum canis* infection in challenged guinea pigs is shown after different observation periods. Compared with vaccinated animals unvaccinated control animals had more severe clinical symptoms in 29 day and 36 day.

TABLE 24

Number of guinea pigs with clinical symptoms of Microsporum canis disease

| Group | Complex/Vaccine | Date of observation | | | |
|---|---|---|---|---|---|
| | | Day 15 | Day 22 | Day 29 | Day 36 |
| 1 | Example 48 | 4/5 | 5/5 | 3/5 | 0/5 |
| 2 | Example 49 | 4/5 | 5/5 | 4/5 | 0/5 |
| 3 | Untreated control | 5/5 | 5/5 | 4/5 | 4/5 |

(Note: number of animals with clinical symptoms/number of challenged)

Compared with the control group the less vaccinated animals had clinical symptoms on day 29 and 36.

TABLE 25

Clinical symptoms of Trichophyton verrucosum disease in guinea pigs

| Vaccine prepared according to | | Date of observation | | | |
|---|---|---|---|---|---|
| | | Day 15 | Day 22 | Day 29 | Day 36 |
| Example 50 | mean | 2.2 | 3.6 | 1.6 | 0 |
| Untreated control | mean | 2.2 | 4.2 | 4.0 | 2.0 |

The severity of clinical symptoms of *Trichophyton verrucosum* infection in challenged guinea pigs is shown after different observation periods. Compared with vaccinated animals unvaccinated control animals had more severe clinical symptoms in 29 and 36 day.

TABLE 26

Number of guinea pigs with clinical symptoms of Trichophyton verrucosum disease

| Group | Complex/Vaccine | Date of observation | | | |
|---|---|---|---|---|---|
| | | Day 15 | Day 22 | Day 29 | Day 36 |
| 1 | Example 50 | 3/5 | 5/5 | 2/5 | 0/5 |
| 2 | Untreated control | 4/5 | 5/5 | 5/5 | 3/5 |

(Note: number of animals with clinical symptoms/number of challenged)

Compared with the control group the less vaccinated animals had clinical symptoms on days 29 and 36.

TABLE 27

Clinical symptoms of Trichophyton mentagrophytes disease in guinea pigs

| Vaccine prepared according to | | Date of observation | | | |
|---|---|---|---|---|---|
| | | Day 15 | Day 22 | Day 29 | Day 36 |
| Example 50 | mean | 3.0 | 3.4 | 2.0 | 0 |
| Untreated control | mean | 4.0 | 4.8 | 4.0 | 2.0 |

The severity of clinical symptoms of *Trichophyton mentagrophytes* infection in challenged guinea pigs is shown after different observation periods. Compared with vaccinated animals unvaccinated control animals had more severe clinical symptoms on days 29 and 36.

TABLE 28

Number of guinea pigs with clinical symptoms of Trichophyton mentagrophytes disease

| Group | Complex/Vaccine | Date of observation | | | |
|---|---|---|---|---|---|
| | | Day 15 | Day 22 | Day 29 | Day 36 |
| 1 | Example 50 | 3/5 | 5/5 | 5/5 | 0/5 |
| 2 | Untreated control | 4/5 | 5/5 | 5/5 | 4/5 |

(Note: number of animals with clinical symptoms/number of challenged)

Compared with the control group the less vaccinated animals had clinical symptoms on days 29 and 36.

TABLE 29

Clinical symptoms of Microsporum canis disease in guinea pigs

| Vaccine prepared according to | | Date of observation | | | |
|---|---|---|---|---|---|
| | | Day 15 | Day 22 | Day 29 | Day 36 |
| Example 50 | mean | 3.2 | 3.4 | 1.0 | 0 |
| Untreated control | mean | 3.8 | 4.0 | 2.4 | 2.0 |

The severity of clinical symptoms of *Microsporum canis* infection in challenged guinea pigs is shown after different observation periods. Compared with vaccinated animals unvaccinated control animals had more severe clinical symptoms on day 29 and 36.

TABLE 30

Number of guinea pigs with clinical symptoms of Microsporum canis disease

| Group | Complex/Vaccine | Date of observation | | | |
|---|---|---|---|---|---|
| | | Day 15 | Day 22 | Day 29 | Day 36 |
| 1 | Example 50 | 4/5 | 5/5 | 3/5 | 0/5 |
| 2 | Untreated control | 4/5 | 5/5 | 4/5 | 4/5 |

(Note: number of animals with clinical symptoms/number of challenged)

Compared with the control group the less vaccinated animals had clinical symptoms on day 29 and 36.

EXAMPLE 72

Efficacy of the Treatment of Allergic Diseases

TABLE 31

The dynamics of the intensity of the clinical symptoms of allergic bronchitis in horses after application of the vaccine prepared according to example 41 (experimental group) and without vaccination (control group). The vaccine was injected intramuscular 3 times with an interval of 4 days with a dose of 1.0 ml.

| Group of animals | No. | Day 1 | Day 15 | Day 22 | Day 29 | Day 36 | Day 50 |
|---|---|---|---|---|---|---|---|
| Application of vaccine (n = 10) | 1 | 3 | 2 | 0 | 0 | 1 | 1 |
| | 2 | 2 | 1 | 0 | 0 | 0 | 1 |
| | 3 | 3 | 2 | 0 | 0 | 0 | 1 |
| | 4 | 2 | 1 | 0 | 0 | 0 | 0 |
| | 5 | 3 | 1 | 0 | 0 | 0 | 0 |
| | 6 | 4 | 2 | 1 | 0 | 0 | 0 |
| | 7 | 3 | 1 | 0 | 0 | 0 | 0 |
| | 8 | 4 | 3 | 2 | 0 | 0 | 0 |
| | 9 | 2 | 1 | 0 | 0 | 0 | 0 |
| | 10 | 2 | 1 | 0 | 0 | 0 | 0 |
| | Mean | 2.8 | 1.5 | 0.3 | 0 | 0.1 | 0.3 |
| | Deviation | 0.79 | 0.71 | 0.67 | 0.0 | 0.32 | 0.48 |
| Control (n = 5) | 11 | 3 | 2 | 2 | 2 | 2 | 3 |
| | 12 | 4 | 2 | 1 | 1 | 1 | 2 |
| | 13 | 4 | 2 | 1 | 1 | 2 | 2 |
| | 14 | 2 | 1 | 1 | 0 | 1 | 1 |
| | 15 | 2 | 1 | 1 | 0 | 0 | 0 |
| | Mean | 3.0 | 1.6 | 1.2 | 0.8 | 1.2 | 1.6 |
| | Deviation | 1.0 | 0.55 | 0.45 | 0.84 | 0.84 | 1.14 |

Score of Clinical Symptoms
0=no symptoms
1=weak wheeze, without coughing
2=weak wheeze, with coughing
3=expressed wheeze
4=expressed wheeze with clinical symptoms of depression The dynamics of the intensity of the clinical symptoms of allergic bronchitis in horses are shown in FIG. 2.

TABLE 32

The dynamics of the intensity of the clinical symptoms of chronic obstructive pulmonary disease in horses after application of the vaccine prepared according to example 41 (experimental group) and without vaccination (control group). The vaccine was injected 3 times intramuscular with an interval of 4 days in a dose of 1.0 ml. The results are also shown in FIG. 3.

| Group of animals | No. | Day 1 | Day 15 | Day 22 | Day 29 | Day 36 | Day 50 |
|---|---|---|---|---|---|---|---|
| Application | 1 | 3 | 1 | 0 | 1 | 1 | 1 |
| of | 2 | 2 | 1 | 0 | 0 | 0 | 1 |
| vaccine | 3 | 3 | 2 | 1 | 0 | 0 | 0 |
| (n = 10) | 4 | 2 | 1 | 1 | 0 | 0 | 0 |
|  | 5 | 3 | 1 | 0 | 0 | 0 | 0 |
|  | 6 | 4 | 2 | 1 | 0 | 1 | 1 |
|  | 7 | 3 | 1 | 0 | 0 | 0 | 0 |
|  | 8 | 4 | 1 | 2 | 0 | 0 | 0 |
|  | 9 | 2 | 1 | 0 | 0 | 0 | 0 |
|  | 10 | 2 | 1 | 0 | 0 | 0 | 0 |
|  | Mean | 2.8 | 1.2 | 0.5 | 0.1 | 0.2 | 0.3 |
|  | Deviation | 0.79 | 0.42 | 0.71 | 0.32 | 0.42 | 0.48 |
| Control | 11 | 3 | 2 | 0 | 0 | 0 | 0 |
| (n = 5) | 12 | 4 | 1 | 2 | 1 | 1 | 1 |
|  | 13 | 4 | 1 | 1 | 1 | 1 | 1 |
|  | 14 | 2 | 1 | 1 | 0 | 1 | 1 |
|  | 15 | 2 | 1 | 1 | 0 | 0 | 0 |
|  | Mean | 3.0 | 1.2 | 1.0 | 0.4 | 0.6 | 0.6 |
|  | Deviation | 1.0 | 0.45 | 0.71 | 0.55 | 0.55 | 0.55 |

Score of Clinical Symptoms

0=no symptoms

1=weak wheeze, without coughing

2=weak wheeze, with coughing

3=expressed wheeze

4=expressed wheeze with clinical symptoms of depression

TABLE 33

Dynamics of clinical signs of skin diseases in dogs immunized with vaccine according to Example 42 in doses of 0.5 ml and 1.0 ml (Mean score of clinical symptoms in each group was shown; n = 10). The vaccine was injected intramuscular 3 times with an interval of 7 days in a dose of 1.0 ml. The dynamics are also shown in FIG. 4.

| Groups | Dose in ml | Day 1 (1) | Day 7 (2) | Day 15 (3) | Day 21 (4) | Day 30 (5) |
|---|---|---|---|---|---|---|
| 1 | 0.5 | 3.6 | 2.6 | 1.2 | 0 | 0 |
| 2 | 1.0 | 3.9 | 2.0 | 1.2 | 0 | 0 |
| 3 | Control | 3.8 | 3.8 | 3.6 | 3.6 | 3.4 |

Score of Clinical Symptoms

0=no symptoms

1=hair growth, active rejection of crusts or excessive flaking

2=alopecia, no hair growth, rejection of crusts

3=desquamation, swelling or swelling with crust, crust not rejected

4=desquamation or swelling, pain on palpation

5=inflammatory response, necrotic crust

TABLE 34

Dynamics of clinical signs of skin diseases in dogs immunized with vaccine according to Example 50 intramuscular in doses of 0.5 ml (Mean score of clinical symptoms in each group was shown; in vaccinators n = 15 and in control group n = 15). The vaccine was injected 3 times with an interval of 3 to 4 days. The results are also shown in FIG. 5.

| Groups | | Day 1 | Day 7 | Day 15 | Day 21 | Day 30 |
|---|---|---|---|---|---|---|
| 1 Vaccinators | Mean | 3.5 | 2.8 | 1.6 | 0.67 | 0 |
|  | Deviation | 0.83 | 1.01 | 0.99 | 0.72 | 0.0 |
| 2 Control | Mean | 3.8 | 3.8 | 3.6 | 3.6 | 3.4 |
|  | Deviation | 0.84 | 0.84 | 0.55 | 0.89 | 0.55 |

Score of Clinical Symptoms

0=no symptoms

1=hair growth, active rejection of crusts or excessive flaking

2=alopecia, no hair growth, rejection of crusts

3=desquamation, swelling or swelling with crust, crust not rejected

4=desquamation or swelling, pain on palpation

5=inflammatory response, necrotic crust

TABLE 35

Ear swelling test of mice.
The reaction to the provocation in mice vaccinated subcutaneously with product according to Example 41 compere to treated with Hostacortin ® H (corticosteroid)

| Medicine | Dose (ml) | Σ Ear thickness after 2 hours post challenge (μm) | | Σ Ear thickness after 24 hours post challenge (μm) | | Σ Ear thickness after 48 hours post challenge (μm) | |
|---|---|---|---|---|---|---|---|
|  |  | Left | Right | Left | Right | Left | Right |
| Example 41 | 0.1 | 322 | 330 | 315 | 335 | 315 | 325 |
| Hostacortin ® H | 0.1 | 335 | 345 | 330 | 360 | 326 | 355 |
| Control | 0.1 | 320 | 375 | 320 | 405 | 325 | 387 |

TABLE 36

Antiallergic activity of vaccine prepared according to Example 41.

| Medicine | Dose (ml) | Antiallergic activity in Ear swelling test (%) | | |
|---|---|---|---|---|
|  |  | after 2 hours post challenge | after 24 hours post challenge | after 48 hours post challenge |
| Example 41 | 0.1 | 14.7 | 20.3 | 16.5 |
| Hostacortin ® H | 0.1 | 14.2 | 17.5 | 10.7 |

Ear erythema was determined by visual inspection and detection of presence (+) or absence (−) signs.

The thickness of the control and experimental ear in all animals was measured with a micrometer. Performance measurements were summed (Σ) separately the right and left ears in groups. The percentage of ear swelling and activity series is calculated using the following formulas:

1. % Ear swelling (control group) =
$$\frac{\Sigma \text{ Ear thickness after challenge with allergen}}{\Sigma \text{ Ear thickness after challenge with solvent}} \times 100$$

2. % Ear swelling (vaccinators) =
$$\frac{\Sigma \text{ Ear thickness after challenge with allergen}}{\Sigma \text{ Ear thickness after challenge with solvent}} \times 100$$

3. Activity of vaccine % =
% Ear swelling in control group − % Ear swelling in vaccinators In all stages of the experiment the positive dynamics of reducing inflammatory response after vaccination and use of prednisolone-21-acetyl in challenged mice was observed. The most expressed inhibition of inflammation reaction was 24 hours after the provocation. It should be noted that all of the control animals' erythema with injection of vessels on the right ear (allergen provocation site) were reacted. In the vaccinated animals the immediate type allergic reaction was not expressed. Intensive erythema on the ear after applying the allergen was not observed. The intensity of the ear oedema was significantly higher in the control animals than in the vaccinated mice and greater than threshold of 10%. Also, it should be noted that a stronger inhibition provocations was in vaccinated animals than in the treated with prednisolone-21-acetate. The amount of unreacted animals in control and test groups ranged from 56 to 80%, which is permitted by the method.

TABLE 37

Ear swelling test of mice.
The reaction to the provocation in mice vaccinated subcutaneously with different doses product according to Example 41.

| Medicine | Dose (ml) | Σ Ear thickness after 2 hours post challenge (μm) | | Σ Ear thickness after 24 hours post challenge (μm) | | Σ Ear thickness after 48 hours post challenge (μm) | |
|---|---|---|---|---|---|---|---|
| | | Left | Right | Left | Right | Left | Right |
| Example (diluted 5 times) | 0.1 | 352 | 394 | 346 | 415 | 344 | 397 |
| Example | 0.1 | 346 | 375 | 349 | 367 | 345 | 358 |
| Example | 0.5 | 340 | 368 | 338 | 351 | 340 | 352 |
| Example | 1.0 | 332 | 375 | 329 | 389 | 325 | 386 |
| Control | 1.0 | 338 | 379 | 341 | 408 | 342 | 410 |

TABLE 38

Antiallergic activity of vaccine prepared according to Example 41.

| Medicine | Dose (ml) | Antiallergic activity in Ear swelling test (%) | | |
|---|---|---|---|---|
| | | after 2 hours post challenge | after 24 hours post challenge | after 48 hours post challenge |
| Example (diluted 5 times) | 0.1 | 0.2 | −0.3 | 4.5 |
| Example | 0.1 | 3.7 | 14.4 | 17.0 |
| Example | 0.5 | 3.9 | 15.8 | 16.4 |
| Example | 1.0 | −0.9 | 1.4 | 1.1 |

It should be noted that despite the small difference in thickness of the ear of the control and vaccinated mice at a dose of 0.1 ml and 0.5 ml 2 hours after challenge, but all control animals showed erythema with injection vessels on the right ear (the allergen provocation). In the vaccinated animals immediate type of allergic reaction was not expressed.

Allergic reaction 24 and 48 hours was observed as the results of provocation in the control and vaccinated at a dose of 0.1 ml of diluted vaccine and undiluted vaccine with dose of 1.0 ml. The reaction after provocation of allergic reaction in mice vaccinated with a dose of 0.1 ml and 0.5 ml absent or weakly expressed. The intensity of the ear oedema was significantly higher in the control animals and in groups vaccinated with diluted vaccine and vaccine in dose of 1.0 ml, than in other vaccinators. The amount of unreacted animals in control and test groups ranged from 65 to 81%, which is permitted by the method.

TABLE 39

Dynamics of clinical signs of skin diseases in dogs immunized intramuscularly with vaccine according to Examples 41 and 43 in a dose of 0.5 ml (Mean score of clinical symptoms in each group was shown; n = 10). The vaccine was injected 3 times with an interval of 7 days.

| Groups | Example | Day 1 (1) | Day 7 (2) | Day 15 (3) | Day 21 (4) | Day 30 (5) |
|---|---|---|---|---|---|---|
| 1 | | 4.0 | 2.2 | 1.4 | 0 | 0 |
| 2 | | 4.0 | 2.6 | 1.6 | 0 | 0 |
| 3 | Control | 3.8 | 3.8 | 3.8 | 3.6 | 3.4 |

Score of Clinical Symptoms
0=no symptoms
1=hair growth, active rejection of crusts or excessive flaking
2=alopecia, no hair growth, rejection of crusts
3=desquamation, swelling or swelling with crust, crust not rejected
4=desquamation or swelling, pain on palpation
5=inflammatory response, necrotic crust

TABLE 40

Dynamics of clinical signs of rhinitis in cats treated with vaccine prepared according to Example 42. The animals were treated by instillation of the nose the vaccine for five days at a dose of 1-2 drops into each nasal passage 1-2 times a day, other animals from control group were treated by the same way but with physiological sodium chloride solution (placebo). The animals were examined with a description of the clinical manifestations of the disease before treatment and on day 5, 10 20 and 30 after first application. In the case of aggravation of allergic rhinitis the second course of treatment for five days was done. The results are also shown in FIG. 7.

| No. | Name | Day 1 | Day 5 | Day 10 | Day 20 | Day 30 |
|---|---|---|---|---|---|---|
| 1 | Bars | 4 | 0 | 1 | 0 | 0 |
| 2 | Vens | 4 | 0 | 3 | 0 | 0 |
| 3 | Masha | 4 | 2 | 0 | 0 | 0 |
| 4 | Mica | 3 | 0 | 2 | 0 | 0 |
| 5 | Nica | 4 | 0 | 0 | 0 | 0 |
| 6 | Nels | 4 | 2 | 0 | 0 | 0 |
| 7 | Roma | 4 | 0 | 2 | 0 | 0 |
| 8 | Timosha | 4 | 0 | 2 | 0 | 0 |
| 9 | Tomka | 4 | 2 | 0 | 0 | 0 |
| 10 | Niusha | 4 | 0 | 0 | 0 | 0 |
| | Mean | 3.9 | 0.6 | 1.0 | 0 | 0 |
| | Deviation | 0.28 | 1.8 | 1.0 | 0.0 | 0.0 |
| 11 | Dusia | 4 | 4 | 4 | 4 | — |
| 12 | Max | 4 | 3 | 4 | 3 | — |
| 13 | Pushok | 4 | 3 | 4 | 4 | — |
| 14 | Filka | 4 | 4 | 3 | 3 | — |
| 15 | Rudy | 4 | 4 | 4 | 4 | — |

TABLE 40-continued

Dynamics of clinical signs of rhinitis in cats treated with vaccine prepared according to Example 42. The animals were treated by instillation of the nose the vaccine for five days at a dose of 1-2 drops into each nasal passage 1-2 times a day, other animals from control group were treated by the same way but with physiological sodium chloride solution (placebo). The animals were examined with a description of the clinical manifestations of the disease before treatment and on day 5, 10 20 and 30 after first application. In the case of aggravation of allergic rhinitis the second course of treatment for five days was done. The results are also shown in FIG. 7.

| No. | Name | Day 1 | Day 5 | Day 10 | Day 20 | Day 30 |
|---|---|---|---|---|---|---|
| | Mean | 4.0 | 3.6 | 3.8 | 3.6 | — |
| | Deviation | 0.0 | 0.3 | 0.5 | 0.3 | — |

0=no symptoms

1=hyperemia and/or swelling of the mucous membranes of the nasal passages

2=slight discharge from the nose

3=hyperemia and/or swelling of the mucous membranes of the nasal passages discharge from the nose 4=difficulty breathing, hyperemia and swelling of the mucous membranes of the nasal passages, heavy discharge from the nose 5=death of animals

TABLE 41

Dynamics of clinical signs of rhinitis in dogs treated with vaccine prepared according to Example 43. The animals were treated by instillation of the nose the vaccine for five days at a dose of 1-2 drops into each nasal passage 1-2 times a day, other animals from control group were treated by the same way but with physiological sodium chloride solution (placebo). The animals were examined with a description of the clinical manifestations of the disease before treatment and on day 5, 10 20 and 30 after first application. In the case of aggravation of allergic rhinitis the second course of treatment for five days was done. The results are also shown in FIG. 8.

| No. | Name | Day 1 | Day 5 | Day 10 | Day 20 | Day 30 |
|---|---|---|---|---|---|---|
| 1 | Mara | 4 | 1 | 0 | 0 | 0 |
| 2 | Paramon | 4 | 0 | 2 | 0 | 0 |
| 3 | Zoran | 3 | 0 | 0 | 0 | 0 |
| 4 | Bred | 3 | 0 | 2 | 0 | 0 |
| 5 | Rembo | 4 | 0 | 0 | 0 | 0 |
| 6 | Tornado | 3 | 0 | 1 | 0 | 0 |
| 7 | Tropka | 3 | 0 | 2 | 0 | 0 |
| 8 | Ataman | 3 | 2 | 0 | 0 | 0 |
| 9 | Arkan | 4 | 0 | 0 | 0 | 0 |
| 10 | Barbos | 4 | 0 | 0 | 0 | 0 |
| | Mean | 3.5 | 0.3 | 0.7 | 0 | 0 |
| | Deviation | 0.28 | 0.98 | 0.87 | 0.0 | 0.0 |
| 11 | Seras | 4 | 4 | 4 | 4 | — |
| 12 | Bingo | 3 | 3 | 3 | 3 | — |
| 13 | Drujok | 3 | 2 | 3 | 3 | — |
| 14 | Racket | 4 | 3 | 3 | 3 | — |
| 15 | Bernt | 4 | 4 | 4 | 4 | — |
| | Mean | 3.6 | 3.2 | 3.4 | 3.4 | — |
| | Deviation | 0.3 | 0.63 | 0.55 | 0.68 | — |

Score of Symptoms:

0=no symptoms

1=hyperemia and/or swelling of the mucous membranes of the nasal passages

2=slight discharge from the nose

3=hyperemia and/or swelling of the mucous membranes of the nasal passages discharge from the nose 4=difficulty breathing, hyperemia and swelling of the mucous membranes of the nasal passages, heavy discharge from the nose 5=death of animals

TABLE 42

Dynamics of clinical signs of conjunctivitis in cats treated with vaccine prepared according to Example 54. Ten cats were treated by instillation of the vaccine for three-five days at a dose of 1-2 drops into each eye 2-3 times per day. In the absence of clinical signs of treatment was discontinued. The other 5 animals were treated with a physiological sodium chloride solution (placebo) as well as experimental animals of the experimental group. The animals were examined with a description of the clinical manifestations of the disease before treatment and every day during the treatment. Then the animals were examined on day 10. The results are also shown in FIG. 9.

| No. | Name | Day 1 | Day 2 | Day 3 | Day 4 | Day 5 | Day 10 |
|---|---|---|---|---|---|---|---|
| 1 | Dark | 4 | 2 | 1 | 1 | 0 | 0 |
| 2 | Felix | 4 | 1 | 0 | 0 | 0 | 2 |
| 3 | Barsa | 3 | 2 | 1 | 0 | 0 | 0 |
| 4 | My | 4 | 2 | 2 | 0 | 0 | 1 |
| 5 | Rudy | 4 | 0 | 0 | 0 | 0 | 0 |
| 6 | Boris | 4 | 2 | 1 | 0 | 0 | 0 |
| 7 | Zanika | 4 | 2 | 1 | 1 | 1 | 0 |
| 8 | Plaksa | 4 | 1 | 0 | 0 | 0 | 0 |
| 9 | Gray | 4 | 2 | 0 | 0 | 0 | 2 |
| 10 | Markisa | 4 | 2 | 1 | 0 | 0 | 0 |
| | Mean | 3.9 | 1.6 | 0.7 | 0.2 | 0.1 | 0.3 |
| | Deviation | 0.28 | 1.2 | 0.5 | 0.5 | 0.8 | 0.9 |
| 11 | Zadira | 4 | 4 | 4 | 4 | — | — |
| 12 | Visy | 4 | 4 | 4 | 4 | — | — |
| 13 | Trindy | 4 | 4 | 4 | 4 | — | — |
| 14 | Riny | 4 | 4 | 4 | 4 | — | — |
| 15 | Fily | 4 | 4 | 4 | 4 | — | — |
| | Mean | 4.0 | 4.0 | 4.0 | 4.0 | — | — |
| | Deviation | 0.0 | 0.0 | 0.0 | 0.0 | — | — |

Score of Symptoms:

0=no symptoms

1=hyperemia and/or swelling of the conjunctiva

2=slight lacrimation, discharge from the eyes

3=hyperemia and/or swelling of the conjunctiva, discharge from the eyes

4=hyperemia and swelling of the conjunctiva, intensive discharge from the eyes

5=destruction of eyeball

EXAMPLE 73. EFFICACY OF THE TREATMENT OF COMMON WARTS

Case 1. The efficacy of a vaccine prepared as described in Example 38 was demonstrated by the vaccination of 16 year old girl with Common warts (Verucae vulgares and paronychial warts). The vaccine was applied 5 times at an interval of 24 hours topically with plaster and drops under affected nail, resulting in a significant reduction of the amount of warts after the last application and the warts disappeared about two weeks after the last treatment. No severe side effects were observed.

Case 2. The efficacy of a vaccine prepared as described in Example 39 was demonstrated by the vaccination of 12 year old girl with Common warts (Verucae vulgares). The vaccine was applied 7 times at an interval of 24 hours topically with plaster, resulting in a significant reduction of the amount of warts after the last application and the warts disappeared about two weeks after the last treatment. No severe side effects were observed.

Case 3. The efficacy of a vaccine prepared as described in Example 40 was demonstrated by the vaccination of 6 year old boy with Common warts (Verucae vulgares). The vaccine was applied 6 times at an interval of 24 hours topically with plaster, resulting in a significant reduction of the amount of warts after the last application and the warts disappeared about two weeks after the last treatment. No severe side effects were observed.

EXAMPLE 74. HYDRO-COLLOIDS

Chemical nomenclature: Chitosan-Valeric acid-Hydro-Colloid
Subtitle: Polyaminosugar-Valeric acid-Hydrocomplex
Structural Formula:

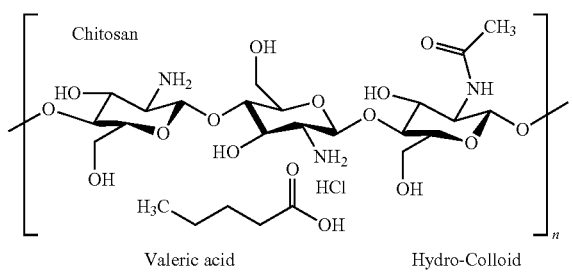

Valeric acid            Hydro-Colloid

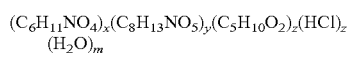
Chemical formula:

General Properties
Molecular weight: x*(161)+y*(203)+z*(102)+z*(36.5)+m*(18)
Appearance: natural white to yellowish viscous liquid with typical odor
Solubility: soluble in: Water
Odor: typical, similar to Valeric acid
Density: 1.002
pH-value: 5.5
Storage: Keep protected from light; store in a container protected from air in a refrigerator at 4°-8° C.
Stability: 36 months under conditions described above
Chemical nomenclature: Chitosan-4-Aminobenzoic acid-Hydro-Colloid
Subtitle: Polyaminosugar-p-Aminobenzoic acid-Hydrocomplex
Structural Formula:

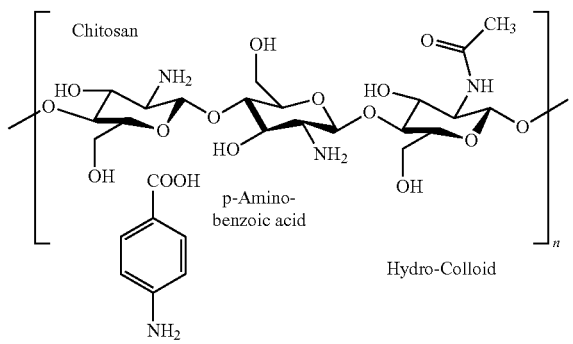

Hydro-Colloid

Chemical formula:

General Properties
Molecular weight: x*(161)+y*(203)+z*(137.14)+m*(18)
Appearance: Yellowish to yellow viscous liquid Chemical nomenclature: Chitosan-Glucuronic acid-Hydro-Colloid
Subtitle: Polyaminosugar-Glucuronic acid-Hydrocomplex
Structural Formula:

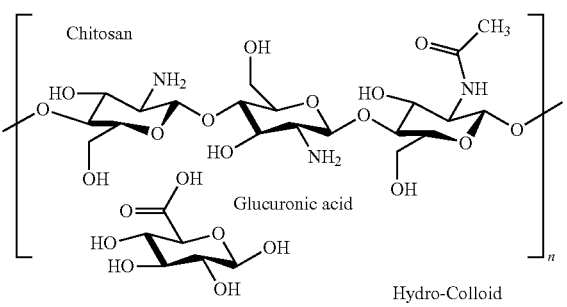

Hydro-Colloid

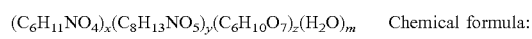
Chemical formula:

General Properties
Molecular weight: x*(161)+y*(203)+z*(194.14)+m*(18)
Appearance: Yellowish to yellow viscous liquid

EXAMPLE 75. MANUFACTURING OF CHITOSAN-VALERIC ACID-HYDRO-COLLOID

Purification of Chitosan 80/100 and 80/200, AS-No.: 9012-76-4, Amino-N-acetyl-D-glucosamine is sterilized in a separate vessel and is carried out to obtain Chitosan in pharmaceutical quality.
Reagent Solution
Sterile Amino-N-acetyl-D-glucosamine is resuspended under stirring for 15 minutes in this sterile water. 400 ml of Acetic acid is added to suspension under stirring (24 h) until a clear solution is obtained.
Purification Step
To this solution the 4 N Sodium hydroxide solution is added drop by drop (carefully) to obtain a pH 8.0 to 8.5. The resulting solution precipitates to a white mass. The obtained suspension is stirred not less than 30 minutes. The residue is separated from the liquid phase by filtration.
Resuspension
The precipitate is resuspended in an equal amount of purified (sterile) water (water for injection (Pharm. Eur.)) (40l, initial amount). 80 ml of Pentanoyl chloride is measured. Under stirring conditions the Pentanoyl chloride is added drop by drop to the suspension. The obtained suspension is stirred until the solution is clear. 1.6 g Thiomersal is added (40 µg/mL). The clear solution is the active ingredient (Hydro-Colloid). The obtained polysaccharide colloid (CVHC) is stored under 4° C. to 8° C. For an end product a aqueous solution is done with defined biological activity.
Overview of the Reaction Steps of Manufacturing
1. Chitosan+water→suspension
suspension+HAc (24 h)→Chitosan-HAc-solution
2. Purification step
2.1. Chitosan-HAc-solution+4N NaOH→(pH 8-8.5)Chitosan+NaAc+H$_2$O
2.2. Chitosan+NaAc+H$_2$O→H$_2$O+NaAc
→Chitosan (solid, purified)
3. Production
Chitosan (solid)+H$_2$O+Pentanoylchlorid→

Chitosan+Valeric acid+$H_2O$+HCl→CVHC (Chitosan-Valeric acid-Hydro-Colloid)

The production is a combination of a purification step of the basic material Chitosan and in process reaction with the second reagent Pentanoyl chloride.

This first critical step is the precipitation of Chitosan to obtain the total amount of the purified chitosan in pharmaceutical quality.

In process control: The reaction time and the pH-value are monitored to get a quantitative precipitation.

Test for the Pharmaceutical Quality of Chitosan:
Test for the Quality of the Intermediate (Chitosan Pharm Quality)

Solubility in water: A sample of about 250 mg of the precipitate of Chitosan is resuspended in 1 ml of purified water Target: No solubility can be obtained
Quality: is fulfilled if no reduction of the amount of the solid material can be detected.

Solubility in stronger acids: In parallel same amount of precipitate is suspended in 1 ml HCl (3N)

Target: Total solution
Quality: is fulfilled if a solution of the total amount of the solid material can be detected.

The second critical step is the dissolution process to the active ingredient. The control is done visually: The total amount of the precipitate should be solubilized.

EXAMPLE 76. EXAMINATION ON IDENTITY BY USING UV/VIS-SPECTROSCOPY

Test method according to EUROPEAN PHARMACOPOEIA 2.2.25 was used.
  Apparatus: Spectrophotometer Jasco 7800
  Conditions of measurement: Bandwidth 2 nm
  Range 200-600 nm
  Blank correction with solvent
  Temperature: 25° C.
  UV-Cell: 12.5×45 mm semi-micro, 10 mm path length UV-grade silica
  Solvent: $H_2O$
  Test solution: An adequate sample of Chitosan HCl, Chitosan-HAc, Chitosan, Chitosan-Valeric acid-Hydro Colloid and valeric acid, respectively was dissolved in the solvent above. This mixture was shacked and afterwards sonified in an ultrasonic bath for 5 min.

The absorption maxima according to the general fundamentals of spectroscopy and the chemical structure with specific chromophore groups and substituents can be expected at: 200 nm for Chitosan HCl, Chitosan-HAc, Chitosan-Valeric acid-Hydro Colloid and valeric acid, respectively

| UV-Maximum | Chitosan HCl | Chitosan HAc | Chitosan | CVHC | Valeric acid |
|---|---|---|---|---|---|
| nm | 200 | 200 | — | 200 | 211 |

The absorption maxima of Chitosan could not be analysed since Chitosan is a water insoluble solid, which can also not be solubilized in typical organic solvents.

The comparison of all spectra show no significance or structural modification like aromatic bonds etc. Based on the measured spectra and literature data of the raw materials the measured spectrum corresponds to prospected spectra. Thus, the measured data above confirm the identity of the prospected structure.

EXAMPLE 77. IR-ABSORPTION SPECTROPHOTOMETRY

Test method according to EUROPEAN PHARMACOPOEIA 2.2.24 was used.

For identification of the active principle Chitosan-Valeric acid-Hydro-Colloid a series of IR-spectra of different Chitosan-Derivates are compared with the spectrum of the product and of Valerie acid.

1. Method and Parameters
Apparatus Infrared-Spectrometer FT/IR 410 Jasco
Range: 4000 $cm^{-1}$ to 600 $cm^{-1}$
Test sample: A mixture of 4.8 mg of Chitosan, or a mixture of 4 mg of Chitosan-HCl or a mixture of 3.8 mg of Chitosan Acetate and 100 mg KBr is carefully grinded and pressed to a suitable potassium bromide disk, or a film of Chitosan-Valeric acid-Hydro Colloid or NaCl plate for valeric acid Conditions of Measurement:
Background correction: actual
Temperature 20° C.

The measured spectrum corresponds directly to the literature spectra from database.

Result: The measured data above confirms the identity of the tested substances.

2. Data of the Different IR-Spectra

| Chitosan-Base | Chitosan-HCl | Chitosan-HAc | Dried Chitosan-valeric acid Colloid | Valeric acid |
|---|---|---|---|---|
| 3398 | 3365 | 3424 | 3426 | |
| 2919/2875 | 2887 | 2926/ | 2960-2872 | 2960-2875 |
| | | | | 2673 |
| | 2018 | 2092 | 2130 | |
| | | 1708 | | 1717 |
| 1665 | | | | |
| 1596 | 1606 | | | |
| 1562 | | 1561 | 1569 | |
| | 1509 | | | |
| | | | | 1467/1456 |
| 1421 | 1410 | 1408 | 1424 | 1413 |
| 1377 | 1380 | | | 1381 |
| 1320 | 1320 | 1336 | 1315 | |
| | | | | 1279 |
| 1256 | 1246 | 1254 | 1236 | 1215 |
| 1154 | 1155 | 1155 | 1154 | |
| 1079/1032 | 1084 | 1089 | 1076-1013 | 1109 |
| 897 | 896 | 890 | 926 | 940 |

The IR signals of Valeric acid in the active principle are very small to not visible. Comparison to literature data: Based on the measured spectra and literature data of the raw materials, the measured spectrum of CVHC corresponds to prospected spectrum.

Result: The measured data above confirm the identity of the proposed structure.

EXAMPLE 78. $^{13}$C-NMR-SPECTROSCOPY ANALYSIS

Test method according to EUROPEAN PHARMACOPOEIA 2.2.33 was used.
a) 13C-NMR-Spectrum of Chitosan
1. Method and Parameters
Apparatus Bruker AMX 500 AVANCE Conditions of Measurement Scan frequency: 125 MHz for Chitosan, Chitosan HCl, Chitosan HAc, Glucosamin HCl, N-Acetylglucosamin, Chitosan-Valeric acid-Hydro-Colloid, Valerie acid Temperature: 300 K for Chitosan, Chitosan HCl, Chitosan HAc, Chitosan-Valeric acid-Hydro-Colloid, Valeric acid; 301 K for Glucosamin HCl and N-Acetylglucosamin Solvent: $D_2O$ for Chitosan, Chitosan HCl, Chitosan HAc, Glucosamin HCl, N-Acetylglucosamin;
DMSO-D6 for Chitosan-Valeric acid-Hydro-Colloid
$CDCl_3$ for Valeric acid Concentration:—for Chitosan, Chitosan HCl, Chitosan HAc, Chitosan-Valeric acid-Hydro-Colloid;
approx. 15 mg/0.5 ml for Glucosamin HCl, N-Acetylglucosamin and Valerie acid Calibration:—for Chitosan, Chitosan HCl, Chitosan HAc, Glucosamin HCl, N-Acetylglucosamin
DMSO-D6 for Chitosan-Valeric acid-Hydro-Colloid
$CDCl_3$ for Valeric acid 1. Results a) $^{13}$C-NMR-Spectroscopy Analysis of Chitosan Measurement in solution: According to the missing solubility in neutral solvents a measurement in solution is not possible.

Measurement in solid state: A measurement in solid state was not possible. Also after long measurement conditions (time) no acceptable signals appeared.

Result: NMR-Identification of Chitosan is not possible.

b) $^{13}$C-NMR-Spectroscopy Analysis of Chitosan HCl

| Results | [d] | Classification (Carbon number) |
|---|---|---|
|  | 97.67 | C1 |
|  | 76.41/74.80 | C5 |
|  | 70.28 | C3 |
|  | 64.41 | C4 |
|  | 60.11 | C6 |
|  | 56.06 | C2 |
| Target | The following characteristic chemical shifts according to the general fundamentals of spectroscopy and the chemical skeleton with substituents can be expected at: | [ppm] 100 70 56 |

General Literature: Hesse, Meier, Zeeh Spektr. Methoden Thieme Verlag 5. Auflage 1995

Result: The measured data above confirms the identity of the tested substance.

c) $^{13}$C-NMR-Spectroscopy Analysis of Chitosan HAc

| Results | [d] | Classification (Carbon number) |
|---|---|---|
| Glucosamine skeleton | 98.39 | C1 |
|  | 74.79 | C5 |
|  | — | C3 |
|  | — | C4 |
|  | — | C6 |
|  | — | C2 |
| Acetic Acid | 23.82 | $CH_3$ |
|  | 180.31 | >C=O |
| Target | The following characteristic chemical shifts according to the general fundamentals of spe spectroscopy and the chemical skeleton with substituents can be expected at: | [ppm] 98.39 23.82 180.31 |

General Literature: Hesse, Meier, Zeeh Spektr. Methoden Thieme Verlag 5. Auflage 1995

Result: The measured data above confirms the identity of the tested substance.

d) $^{13}$C-NMR-Spectroscopy Analysis of Glucosamin HCl

| Results | [d] | Classification (Carbon number) |
|---|---|---|
|  | 92.94/89.34 | C1 |
|  | 76.25 | C5 |
|  | 72.28/71.69 | C3 |
|  | 69.85/69.77 | C4 |
|  | 60.66/60.51 | C6 |
|  | 54.62/57.08 | C2 |
| Target | The following characteristic chemical shifts according to the general fundamentals of spectroscopy and the chemical skeleton with substituents can be expected at: | [ppm] 92.94/89.34 60.66/60.51 54.62/57.08 |

General Literature: Hesse, Meier, Zeeh Spektr. Methoden Thieme Verlag 5. Auflage 1995

Comparison to literature data: The measured spectrum corresponds directly to the literature spectra from database.

Result: The measured data above confirms the identity of the tested substance.

e) $^{13}$C-NMR-Spectroscopy Analysis of N-Acetylglucosamin

| Results | [d] | Classification |
|---|---|---|
|  | 95.06/90.95 | C1 |
|  | 76.01/74.08 | C5 |
|  | 71.64/70.86 | C3 |
|  | 70.22/69.99 | C4 |
|  | 60.89/60.74 | C6 |
|  | 56.90/54.26 | C2 |
|  | 22.29/22.03 | $CH_3$ |
|  | 174.85/174.59 | >C=O |
| Target | The following characteristic chemical shifts according to the general fundamentals of spectroscopy and the chemical skeleton with substituents can be expected at: | 95.06/90.95 22.29/22.03 174.85/174.59 |

General Literature: Hesse, Meier, Zeeh Spektr. Methoden Thieme Verlag 5. Auflage 1995

Result: The measured data above confirms the identity of the tested substance.

f) $^{13}$C-NMR-Spectroscopy Analysis of Chitosan-Valeric Acid-Hydro-Colloid

| Results | [d] | Classification |
|---|---|---|
| Glucosamine skeleton | 100.95 | C1 |
|  | 78.57 | C5 |
|  | 76.10 | C3 |
|  | 73.10 | C4 |
|  | 61.40 | C6 |
|  | 57.57 | C2 |
| Valeric acid | 180.66 | C5' |
|  | 29.23 | C4' |
|  | 24.85 | C3' |
|  | 23.37 | C2' |
|  | 14.87 | C1' |
| Target | The following characteristic chemical shifts according to the general fundamentals of spectroscopy and the chemical skeleton with substituents can be expected at: | [ppm] 100.95 61.40 57.57 180.66 14.87 |

General Literature: Hesse, Meier, Zeeh Spektr. Methoden Thieme Verlag 5. Auflage 1995

Result: The measured data above confirms the identity of the proposed structure.

g) $^{13}$C-NMR-Spectroscopy Analysis of Valeric Acid

| Results | [d] | Classification (Carbon number) |
|---|---|---|
| | 180.5 | C5 |
| | 33.8 | C4 |
| | 26.7 | C3 |
| | 22.2 | C2 |
| | 10.6 | C1 |
| Target | The following characteristic chemical shifts according to the general fundamentals of spectroscopy and the chemical skeleton with substituents can be expected at: | [ppm] 180 10.6 |

General Literature: Hesse, Meier, Zeeh Spektr. Methoden Thieme Verlag 5. Auflage 1995

Comparison to literature data: The measured spectrum corresponds directly to the literature spectra from database.

Result: The measured data above confirms the identity of the tested substance.

3. Comparison of the NMR Spectra

| Chitosan HCl | Chitosan HAc | Glucosamin HCl | N-Acetyl-glucosamin | Chitosan-Valeric acid-Hydro- | Valeric acid | Classification (Carbon number) |
|---|---|---|---|---|---|---|
| 97.7 | 98.4 | 92.9/89.3 | 95.0/91.0 | 101.0 | | C1 |
| 56.1 | | 54.6/57.1 | 54.3/56.9 | 57.6 | | C2 |
| 70.3 | | 71.7/72.3 | 71.6/70.9 | 76.1 | | C3 |
| 64.4 | | 69.9/69.8 | 70.2/70.0 | 73.1 | | C4 |
| 76.4/74.8 | 74.8 | 7 | 76.0/74.1 | 78.6 | | C5 |
| 60.1 | | 60.5/60.7 | 60.9/60.7 | 61.4 | | C6 |
| | 22.7 | | | | | |
| | 23.8 | | | | | |
| | 180.3 | | | | | |
| | | | 174.9/174.6 | | | |
| | | | | 14.9 | 13.06 | |
| | | | | 23.4 | 22.02 | |
| | | | | 24.9 | 26.07 | |
| | | | | 29.2 | 33.8 | |
| | | | | 108.7 | 180.5 | |
| Literature | — | — | X | — | — | X |

Comparison to literature data: Not available or Based on the measured spectra and literature data of the raw materials, the measured spectrum corresponds directly to prospected spectra. Result: The measured data above confirm the identity of the proposed structure.

EXAMPLE 79. TLC-METHOD FOR THE ANALYSIS OF CHITOSAN AND IMPURITIES IN THE NEW PRODUCT CHITOSAN-VALERIC ACID-HYDRO-COLLOID (CVHC)

Test method according to EUROPEAN PHARMACOPOEIA 2.2.27 was used.

This part presents the procedures and data of thin layer chromatography for the identification of CVHC along with the Rf values in the used solvent mixtures and spot colors when detected under UV-light (365 nm and 254 nm), visible light and with typical visualisation reagents.

The original based raw material for any kind of glucosamines is the natural material Chitin from insects or crabs. The monomeric structure of these biopolymers is N-Acetyl-Glucosamine.

For pharmaceutical and other use in most cases deacetylated Chitin is typical. This resulting biopolymer is the so called Chitosan, which can be modified into water soluble ionic compounds. The monomeric structure of this Chitosan should be theoretically Glucosamine. Because the deacetylation step does not run totally, Chitosan has a mixed structure of N-Acetyglucosamine (acetylated) and Glucosamine (deacetylated) units. Chitosan-Valeric acid-Hydro-Colloid is a new Polyaminosugar-valeric acid hydrocomplex. Therefore no positive analytical test results for N-Acetyl-Glucosamine and Glucosamine should be possible. If monomeric fragments are embedded as residual impurities, it should be possible to identify Chitosan in form of its water soluble ionic compounds Chitosan HCl and Chitosan HAc.

1. Method

| Apparatus | Camag Chromatographic Tank System |
|---|---|
| TLC-plate | Merck Si 60 F 254 precoated plates |
| Conditions | Protected from sunlight and with chamber saturation |
| Temperature | 20-25° C. |
| Development: | Vertical development |

Chromatographic Conditions

| Sample-solution Application | See the single analytes 30 μl |
|---|---|
| Drying | Min. 2 minutes in an air-stream |
| Motion range | 80 mm |

| Solvents | Acetone | Water | 25% aq. Ammonia | — |
|---|---|---|---|---|
| Mixture | 20 | 10 | 5 | — |

2. Analysis and Results a) Chitosan

Sample Preparation

Sample: Chitosan suspended in water

1) Apparatus: reflux condenser
Conditions: heating for about 30 minutes under reflux (145° C.)
2) Apparatus: Ultra sonic bath
Conditions: Sonification for about 30 minutes at 45° C.
3) Apparatus: reflux condenser
Conditions: heating for about 30 minutes under reflux (145° C.)
4) Filtration: 0.45 μm filter
The clear filtrate was used for analysis.
Detection with UV-Fluorescence and VIS

|  | Fluorescence wavelength | | |
| --- | --- | --- | --- |
|  | 254 nm | 365 nm | VIS |
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
| --- | --- | --- | --- | --- |
| Compound signal | No | No | No | No |
| Impurities | No | No | No | No |

Group specific reagent 1: Naturstoff-Reagent/DT/366 nm
Group specific reagent 2: 5% Ninhydrine/EtOH

| Rf-value | No signal for chitosan can be identified | — |
| --- | --- | --- |
|  | Non specified impurities: | Not detected |

Alternative: Solubilization in organic solvents show equal results because of the missing solubility of Chitosan.

Result: An acceptable solution of Chitosan in waterish or organic solvents like Methanol etc. is not possible. A suitable solubilization of Chitosan is only possible in stronger acids like HCl or HAc under production of Chitosan HCl or Chitosan HAc.

b) Chitosan HCl 5 mg Chitosan HCl/ml $H_2O$ was used for analysis.

Detection with UV-fluorescence and VIS

|  | Fluorescence wavelength | | |
| --- | --- | --- | --- |
|  | 254 nm | 365 nm | VIS |
| Compound signal | No | No | No |
| Impurities | No | No | No |

Detection with visualisation reagents

| Visible light | Group specific reagent 1 | Group specific reagent 2 | Anisaldehyde-Sulfuric acid reagent | Iodine |
| --- | --- | --- | --- | --- |
| Compound signal | No | No | Grey spot | Brown spot |
| Impurities | No | No | No | No |

Group specific reagent 1: Naturstoff-Reagent/DT/366 nm
Group specific reagent 2: 5% Ninhydrine/EtOH

| Rf-value | Chitosan HCl | 0.0 |
| --- | --- | --- |
|  | Non specified impurities: | Not detected |
| Target | Compound purity | One main spot |
|  | Anisaldehyd-Sulfuric acid-reagent respectively Iodine as non-selective reagents for detection of non-specified impurities should show no greater impurities A relative retardation factor (Rf) of this compound according to the chemical skeleton under this described chromatographic conditions for such an polymer can be expected at: | |
|  | 0.0 | — — |

Result: Compound purity; One main spot.

c) Chitosan HAc 5 mg Chitosan HAc/ml $H_2O$ was used for analysis.

Detection with UV-Fluorescence and VIS

|  | Fluorescence wavelength | | |
| --- | --- | --- | --- |
|  | 254 nm | 365 nm | VIS |
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
| --- | --- | --- | --- | --- |
| Compound signal | No | No | Grey spot | Brown spot |
| Impurities | No | No | No | No |

Group specific reagent 1: Naturstoff-Reagent/DT/366 nm
Group specific reagent 2: 5% Ninhydrine/EtOH

| Rf-value | Chitosan HAc | 0.0 |
| --- | --- | --- |
|  | Non specified impurities: | Not detected |
| Literature Value | Not available data from | — |
| Target | Compound purity | One main spot |
|  | Anisaldehyd-Sulfuric acid-reagent respectively Iodine as non-selective reagents for detection of non-specified impurities should show no greater impurities A relative retardation factor (Rf) of this compound according to the chemical skeleton under this described chromatographic conditions for such an polymer can be expected at: | |
|  | 0.0 | — — |

Result: Compound purity; One main spot.

d) Glucosamine HCl 5 mg Glucosamine Ha/ml $H_2O$ was used for analysis.

Detection with UV-fluorescence and VIS

|  | Fluorescence wavelength | | |
| --- | --- | --- | --- |
|  | 254 nm | 365 nm | VIS |
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
| --- | --- | --- | --- | --- |
| Compound signal | Blue spot | Red spot | Grey spot | Brown spot |
| Impurities | No | No | No | No |

Group specific reagent 1: Naturstoff-Reagent/DT/366 nm
Group specific reagent 2: 5% Ninhydrine/EtOH

| Rf-value | Glucosamine HCl | 0.67 |
| --- | --- | --- |
|  | Non specified impurities: | Not detected |
| Literature Value | Not available data from | — |
| Target | Compound purity | One main spot |
|  | Anisaldehyd-Sulfuric acid-reagent respectively Iodine as non-selective reagents for detection of non-specified impurities should show no greater impurities A relative retardation factor (Rf) of this compound according to the chemical skeleton under this described chromatographic conditions can be expected between | |
|  | 0.6 and | 0.8 |

Result: Compound purity; One main spot.
e) N-Acetylglucosamine
5 mg N-Acetylglucosamine/ml $H_2O$ was used for analysis
Detection with UV-Fluorescence and VIS

|  | Fluorescence wavelength | | |
| --- | --- | --- | --- |
|  | 254 nm | 365 nm | VIS |
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
| --- | --- | --- | --- | --- |
| Compound signal | Blue spot | No | Grey spot | Brown spot |
| Impurities | No | No | No | No |

Group specific reagent 1: Naturstoff-Reagent/DT/366 nm
Group specific reagent 2: 5% Ninhydrine/EtOH

| Rf-value | N-Acetylglucosamine | 0.72 |
| --- | --- | --- |
|  | Non specified impurities: | Not detected |
| Target | Compound purity | One main spot |
|  | Anisaldehyd-Sulfuric acid-reagent respectively Iodine as non-selective reagents for detection of non-specified impurities should show no greater impurities A relative retardation factor (Rf) of this compound according to the chemical skeleton under this described chromatographic conditions can be expected between | |
|  | 0.6   and   0.8 | |

Result: Compound purity; One main spot.
f) Chitosan-Valeric acid-Hydro-Colloid (CVHC)
CVHC is a high viscous waterish gel. Two drops of CVHC was used for analysis.
Detection with UV-Fluorescence and VIS

|  | Fluorescence wavelength | | |
| --- | --- | --- | --- |
|  | 254 nm | 365 nm | VIS |
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
| --- | --- | --- | --- | --- |
| Compound signal | No | No | Grey spot | Brown spot |
| Impurities | No | No | No | No |

Group specific reagent 1: Naturstoff-Reagent/DT/366 nm
Group specific reagent 2: 5% Ninhydrine/EtOH

| Rf-value | Chitosan-Valeric acid-Hydro-Colloid | 0.0 |
| --- | --- | --- |
|  | Non specified impurities: | Not detected |
| Literature Value | Not available    data from | — |
| Target | Compound purity     One main spot | |
|  | Anisaldehyd-Sulfuric acid-reagent respectively Iodine as non-selective reagents for detection of non-specified impurities should show no greater impurities A relative retardation factor (Rf) of this compound according to the chemical skeleton under this described chromatographic conditions for such an polymer can be expected at: | |
|  | 0.0    —    — | |

Result: Compound purity; One main spot.
g) Valeric acid
1 μl Valeric acid (pure) was used for analysis.
Detection with UV-Fluorescence and VIS

|  | Fluorescence wavelength | | |
| --- | --- | --- | --- |
|  | 254 nm | 365 nm | VIS |
| Compound signal | No | No | No |
| Impurities | No | No | No |

Detection with Visualisation Reagents

| Visible light | Group specific reagent 1 | Group specific reagent 2 | Anisaldehyde-Sulfuric acid reagent | Iodine |
| --- | --- | --- | --- | --- |
| Compound signal | No | No | No | Yellow spot |
| Impurities | No | No | No | No |

Group specific reagent 1: Naturstoff-Reagent/DT/366 nm
Group specific reagent 2: 5% Ninhydrine/EtOH

| Rf-value | Valeric acid | 0.0 |
| --- | --- | --- |
|  | Non specified impurities: | Not detected |
| Literature Value | Not available    data from | — |
| Target | Compound purity     One main spot | |
|  | Anisaldehyd-Sulfuric acid-reagent respectively Iodine as non-selective reagents for detection of non-specified impurities should show no greater impurities A relative retardation factor (Rf) of this compound according to the chemical skeleton under this described chromatographic conditions can be expected between | |
|  | 0.0    —    — | |

Result: Compound purity; One main spot.
3. Comparison of the Results of the TLC Analysis

|  | Chitosan | Chitosan HCl | Chitosan HAc | Glucosamine HCl | N-Acetyl-glucoamine HCl | Chitosan-Valeric colloid | Valeric acid |
| --- | --- | --- | --- | --- | --- | --- | --- |
| Rf-value | Not possible | 0 | 0 | 0.67 | 0.72 | 0 | 0 |
| Detection | Compound signal | | | | | | |
| UV 254 nm | — | — | — | — | — | — | — |
| UV 365 nm | — | — | — | — | — | — | — |
| Visible light | — | — | — | — | — | — | — |
| Naturstoff-Reagent | — | — | — | Blue spot | Blue spot | — | — |

-continued

|  | Chitosan | Chitosan HCl | Chitosan HAc | Glucosamine HCl | N-Acetyl-glucoamine HCl | Chitosan-Valeric colloid | Valeric acid |
|---|---|---|---|---|---|---|---|
| Ninhydrine Reagent | — | — | — | Red spot | — | — | — |
| Anisaldehyde-Sulfuric acid reagent | — | Grey spot | Grey spot | Grey spot | Grey spot | Grey spot | — |
| Iodine Reagent | — | Brown spot | Brown spot | Brown spot | Brown spot | Brown spot | Yellow Spot |

The results above from TLC show that there is no evidence of monomeric or dimeric structure which could be detected with the specific derivation reagents tested above. The detection and the Rf value of "0" show the similarity of Chitosan-Valeric acid-Hydro-Colloid to the related compounds Chitosan HCl and Chitosan HAc. A specific identification of Valerie acid with this TLC-System failed. Chitosan-Valeric acid-Hydro-Colloid can only be a Poly-Amino-sugar-colloid, but not a solution of Chitosan or a Chitosan derivate with Valerie acid in water.

EXAMPLE 80. TLC-METHOD FOR THE ANALYTICAL DETECTION OF VALERIE ACID IN CHITOSAN-VALERIE ACID-HYDRO-COLLOID

1. Method and Parameters

A new TLC system was established for an identification and purity testing of the constituent Valerie acid.

| | |
|---|---|
| Apparatus | Camag Chromatographic Tank System |
| TLC-plate | Merck Si 60 F 254 precoated plates |
| Conditions | Protected from sunlight and with chamber saturation |
| Temperature | 20-25° C. |
| Development: | Vertical development |

Chromatographic Conditions

| | |
|---|---|
| Drying | Min. 2 minutes in an air-stream |
| Motion range | 80 mm |

Mobile Phase.

| Solvents | Ethyl Acetate | — | — | — |
|---|---|---|---|---|
| Mixture | 100 | — | — | — |

2. Results a) Valeric Acid (Pure)

2 µl of Valeric acid (pure) was used for analysis.
Detection with UV-Fluorescence and VIS

| | Fluorescence wavelength | | |
|---|---|---|---|
| | 254 nm | 365 nm | VIS |
| Compound signal | No | No | No |
| Impurities | No | No | No |

Detection with Visualisation Reagents

| Visible light | Group specific reagent | Anisaldehyde-Sulfuric acid reagent | Iodine |
|---|---|---|---|
| Compound signal | Yellow spot/blue background | Pink spot | Yellowish spot |
| Impurities | No | No | No |

Group specific reagent: Bromcresol Green/Bromphenol Blue/Potassium Permanganate Reagent [Jork et al.]

| | | | |
|---|---|---|---|
| Rf-value | Valeric acid | | 0.56 |
| | Non specified impurities: | | Not detected |
| Literature Value | Not available | data from | — |

Detection limit: of valeric acid with this visualisation reagent after TLC-chromatography: 0.03 µg b) Chitosan-Valeric Acid-Hydro-Colloid (CVHV)

45 µl Chitosan-Valeric acid-Hydro-Colloid, pure (this is an about 850 times higher amount of valeric acid, compared with the tests before) was used for analysis.

Detection with UV-Fluorescence and VIS

| | Fluorescence wavelength | | |
|---|---|---|---|
| | 254 nm | 365 nm | VIS |
| Compound signal | No | No | No |
| Impurities | No | No | No |

Detection with Visualisation Reagents

| Visible light | Group specific reagent | Anisaldehyde-Sulfuric acid reagent | Iodine |
|---|---|---|---|
| Compound signal | Blue spot/blue background | Grey spot | Brown spot |
| Impurities | No | No | No |

Group specific reagent: Bromcresol Green/Bromphenol Blue/Potassium Permanganate Reagent [Jork et al.]

| | |
|---|---|
| Target | Compound purity         One main spot |
| | Anisaldehyd-Sulfuric acid-reagent respectively Iodine as non-selective reagents for detection of non-specified impurities should show no greater impurities |
| | The Group specific reagent Bromcresol Green/Bromphenol Blue/Potassium Permanganate Reagent should show typical results for the compounds |
| | A relative retardation factor (Rf) of this compound according to the chemical skeleton under this described chromatographic conditions can be expected at |
| | 0.0                   for Chitosan-derivatives |
| | appr. 0.6             for valeric acid if available |
| Rf-value | Chitosan-Valeric acid-Hydro-Colloid         0.0 |
| | Non specified impurities:         Not detected |

| Rf-value   | Valeric acid            | Not detected |
|------------|-------------------------|--------------|
|            | Non specified impurities: | Not detected |
| Literature | Not available  data from | —            |
| Value      |                         |              |

Detection limit of valeric acid with this visualisation reagent after TLC-chroma-tography: 0.03 μg Pure Valeric acid can be identified with this TLC-System. Colloidal integrated Valeric acid can not be detected in the pure compound Chitosan-Valeric acid-Hydro-Colloid. The detection and the Rf value of "0" show the similarity of Chitosan-Valeric acid-Hydro-Colloid to other related Chitosan compounds. Chitosan-Valeric acid-Hydro-Colloid can only be a Poly-Amino-sugar colloid, but not a solution of Chitosan or a Chitosan derivate with Valeric acid in water. The results above confirm the identity of the proposed structure.

EXAMPLE 81. ELIMINATION OF VALERIE ACID FROM CHITOSAN-VALERIC ACID-HYDRO-COLLOID WITH HIGH VACUUM AND HIGHER TEMPERATURE

Method: Estimation of the loss on drying (special method)
Apparatus: Speed circulating vacuum concentrator
Conditions: 5 mbar
Temperature: 60° C.
Time: 1 week
End point: Constant mass
Appearance: Glassy mass
Result Odor: No typical odor from valeric acid
Sample Preparation
Redissolution Partly with Water
Appearance: High viscous gel
TLC-Analysis
Apparatus: Camag Chromatographic Tank System
TLC-plate: Merck Si 60 F 254 precoated plates
Conditions: Protected from sunlight and with chamber saturation
Temperature: 20-25° C.
Development: Vertical development
Chromatographic Conditions
Sample-Solution See Above
Application: 5 μl
Drying: Min. 2 minutes in an air-stream
Motion range: 80 mm
Mobile Phase

| Solvents | Ethyl Acetate | — | — | — |
|----------|---------------|---|---|---|
| Mixture  | 100           | — | — | — |

Detection with UV-Fluorescence and VIS

|  | Fluorescence wavelength | | |
|--|---|---|---|
|  | 254 nm | 365 nm | VIS |
| Compound signal | No | No | No |
| Impurities | No | No | No |

Detection with Visualisation Reagents

| Visible light | Group specific reagent | Anisaldehyde-Sulfuric acid reagent | Iodine |
|---|---|---|---|
| Compound signal | Blue spot/blue background | grey spot | brown spot |
| Impurities | No | No | No |
| Rf value | spot | | 0 |

Group specific reagent: Bromcresol Green/Bromphenol Blue/Potassium Permanganate Reagent [Jork et al.]

Detection limit: of Valerie acid with this visualization reagent after TLC-chromatography: 0.03 μg Result: With high vacuum and higher temperature a disproportion of Chitosan-Valeric acid-Hydro-Colloid takes place. The elimination of Valerie acid can be shown by absolutely no typical odor from Valerie acid. The elimination of Valerie acid can be shown by TLC analysis: no typical spot of free valeric acid at Rf-value 0.56. Chitosan or Chitosan compounds can be identified at Rf-value 0. Chitosan-Valeric acid-Hydro-Colloid can only be a Poly-Amino-sugar-colloid, but not a solution of Chitosan or a Chitosan derivate with valeric acid in water.

EXAMPLE 82. DISPROPORTION OF CHITOSAN-VALERIC ACID-HYDRO-COLLOID WITH SOLVENTS

The structure of Chitosan-Valeric acid-Hydro-Colloid is decomposed in Ethyl acetate to Valerie acid and a Chitosan compound.
Sample Preparation
Apparatus: separating funnel, evaporator
Liquid-liquid distribution: 20 ml Chitosan-Valeric acid-Hydro-Colloid and 10 ml Ethyl acetate
Conditions: Shaking for about 5 minutes and wait for phase separation
Separation of phases: The ethyl acetate phase was collected
Concentration step: The about 10 ml were concentrated to liquid residue (waterish) with an evaporator
Resolubilization: in 1 ml Methanol
Homogenization: Centrifugation step about 5 min 12.000 rpm
Phase separation: Upper phase: clear methanolic solution
  Lower phase: high viscous gel
  TLC Analysis of Upper and Lower Phase (See Above)
  a) Analysis of Upper Phase (Clear Methanolic Solution)
  TLC-Analysis
  Apparatus: Camag Chromatographic Tank System
  TLC-plate: Merck Si 60 F 254 precoated plates
  Conditions: Protected from sunlight and with chamber saturation
  Temperature: 20-25° C.
  Development: Vertical development
  Chromatographic Conditions
  Sample-solution: clear methanolic solution
  Application: 5 μl
  Drying: Min. 2 minutes in an air-stream
  Motion range: 80 mm
  Mobile Phase

| Solvents | Ethyl Acetate | — | — | — |
|----------|---------------|---|---|---|
| Mixture  | 100           | — | — | — |

Detection with UV-Fluorescence and VIS

|  | Fluorescence wavelength | | |
|---|---|---|---|
|  | 254 nm | 365 nm | VIS |
| Compound signal | No | No | No |
| Impurities | No | No | No |

Detection with Visualisation Reagents

| Visible light | Group specific reagent | Anisaldehyde-Sulfuric acid reagent | Iodine |
|---|---|---|---|
| Compound signal | Yellow spot/blue background | No | Light yellowish spot |
| Impurities | No | No | No |
| Rf-value | Valeric acid Non specified impurities: | | 0.57 — |

Group specific reagent: Bromcresol Green/Bromphenol Blue/Potassium Permanganate Reagent [Jork et al.]

Detection limit with visualisation reagent: 0.03 μg

Result: The upper phase is a clear methanolic solution. Valeric acid can be identified after decomposition of the Hydro-Colloid in this solution with TLC. No Chitosan or Chitosan compound can be detected with TLC.

b) Analysis of Lower Phase (High Viscous Gel)
TLC-Analysis
Apparatus: Camag Chromatographic Tank System
TLC-plate: Merck Si 60 F 254 precoated plates
Conditions: Protected from sunlight and with chamber
Temperature: 20-25° C.
Development: Vertical development
Chromatographic Conditions
Sample-solution: high viscous gel, totally redissolved in water
Application: 30 μl
Drying: Min. 2 minutes in an air-stream
Motion range: 80 mm
Mobile Phase

| Solvents Mixture | Ethyl Acetate 100 | — — | — — | — — |
|---|---|---|---|---|

Detection with UV-Fluorescence and VIS

|  | Fluorescence wavelength | | |
|---|---|---|---|
|  | 254 nm | 365 nm | VIS |
| Compound signal | No | No | No |
| Impurities | No | No | No |

Detection with Visualisation Reagents

| Visible light | Group specific reagent | Anisaldehyde-Sulfuric acid reagent | Iodine |
|---|---|---|---|
| Compound signal | Blue spot/blue background | Grey spot | Brown spot |
| Impurities | No | No | No |
| Rf-value | Spot Non specified impurities: | | 0 — |

Group specific reagent: Bromcresol Green/Bromphenol Blue/Potassium Permanganate Reagent [Jork et al.]

Detection limit with visualisation reagent: 0.03 μg

Results: The lower phase is a high viscous gel, soluble in water. No Valeric acid can be detected in this phase by TLC. Chitosan or a Chitosan compound can be identified in the lower phase (gel) by TLC.

| Results from TLC analysis | A disproportion of Chitosan-Valeric acid-Hydro-Colloid is possible with typical solvents like Ethyl acetate and afterwards with Methanol A re-solubilization of from disproportioned Chitosan-Valeric acid-Hydro-Colloid can be realized with Methanol The decomposition of Chitosan-Valeric acid-Hydro-Colloid in Ethyl acetate shows two phases |
|---|---|
| | Upper phase — Ethyl acetate phase |
| | Lower phase — Aqueous Colloid residue |
| | After concentration the Ethyl acetate phase was redissolved in Methanol and results also two phases |
| | Upper phase — clear methanolic solution |
| | Lower phase — high viscous gel This gel can be re-dissolved totally in water |
| | can be identified — No Chitosan or Chitosan compound can be detected |
| | No can be identified — Chitosan or a Chitosan compound can be detected |

Summary of the Results

|  |  | Valeric acid pure | Chitosan-Valeric acid-Hydro-Colloid (pure CVHC) | Elimination of from CVHC with high vacuum | Chitosan-Valeric acid-Hydro-Colloid (decomposed with Ethyl acetate) | |
|---|---|---|---|---|---|---|
|  |  |  |  |  | Upper phase (Methanol) | Lower phase (Water) |
| Rf-value | 0.56 | + | − | − | + | − |
| Rf-value | 0 | − | + | + | − | + |
| Detection | | | Compound signal | | | |
| UV 254 nm | | — | — | — | — | — |
| UV 365 nm | | — | — | — | — | — |
| Visible light | | — | — | — | — | — |
| Anisaldehyde-Sulfuric acid reagent | | Pink spot | Grey spot | Grey spot | — | Grey spot |
| Iodine reagent | | Yellowish spot | Brown spot | Brown spot | Light yellowish spot | Brown spot |

-continued

|  | Valeric acid pure | Chitosan-Valeric acid-Hydro-Colloid (pure CVHC) | Elimination of from CVHC with high vacuum | Chitosan-Valeric acid-Hydro-Colloid (decomposed with Ethyl acetate) | |
|---|---|---|---|---|---|
|  |  |  |  | Upper phase (Methanol) | Lower phase (Water) |
| Bromcresol Green Bromphenol Blue reagent | Yellow spot | Blue spot | Blue spot | Yellow spot | Blue spot |

Result: Chitosan-Valeric acid-Hydro-Colloid can only be a Poly-Amino-sugar-colloid, but not a solution of Chitosan or a Chitosan derivate with valeric acid in water. The results above confirm the identity of the proposed structure.

EXAMPLE 83. ESTIMATION OF THE RELATIVE DENSITY

Because of the high viscosity of Chitosan-Valeric acid-Hydro-Colloid the estimation of the density is not possible with a density bottle/pycnometer according to Test method according to EUROPEAN PHARMACOPOEIA 2.2.5.

1. Test Method by Weighing
Apparatus: 250 ml volumetric flask
Balance: Sartorius MC 1 LC 2200S
Thermometer: Thermometer with graduation (min 0.5° C.) and a range not more than 60° C.
Results 1.001 $[d_{20}^{20}]$
The active principle is a hydrogel, so the theoretical density should be higher than 1.0. The measured data confirms the identity of the proposed substance.

2. Test Method with Hydrometer
Test method according to EUROPEAN PHARMACOPOEIA 2.2.5 was used.
Apparatus: 250 ml volumetric flask
Hydrometer: Widder 1573°, 20° C.-M100-DIN 12791 Klasse H
Thermometer Thermometer with graduation (min 0.5° C.) and a range not more than 60° C.
Conditions of measurement: Temperature 20+/–0.5° C. with electronic thermostate
Results 1.002 $[d_{20}^{20}]$
The active principle is a hydrogel, so the theoretical density should be higher than 1.0. The measured data confirms the identify of the proposed substance.

EXAMPLE 84. SULPHATED ASH

The Test method according to EUROPEAN PHARMACOPOEIA 2.4.14 was used.
Testing

| Apparatus | Suitable crucible (porcelain or platinum) were ignited at 600 +/– 50° C. for 30 min in a „Muffer"-oven allow to cool in a desiccator over silica gel or other suitable desiccant Estimation of crucible weight |
|---|---|
| Weight | Weight of crucible 1: 52.0120 [g] Weight of crucible 2: 57.6055 [g] |
| Method 2 (acid insoluble ash) | Additional for this Hydrogel a concentration step to dryness was done by drying at 105° C. in an normal oven |

-continued

| | Sample: 25 ml_ of Hydrogel CVHC Usually 1-2 g Sample weight: usually 1-2 g or sufficient amount to obtain a residue of minimum 1 g. Moisten the sample with a small amount of sulfuric acid R [95-97% m/m] (usuallyl ml_) and heat at as low temperature as practicable until the residue is charred. After cooling, moisten the residue with a small amount of sulfuric acid R [95-97% m/m] (usuallyl ml_) Heat until white fumes are no longer evolved Ignite at 600 +/– 50° C. for 30 min until the residue is completely incinerated. Flames are not allowed to be produced at any time during the procedure allow to cool in a desiccator over silica gel or other suitable desiccant Weigh and calculate the percentage of residue |
|---|---|
| Weighting of total weight | Total Weight of crucible 1: 52.0668 g Total Weight of crucible 2: 57.6612 g |
| Sulphated ash content | Value 1: 0.0548 g Value 2: 0.0557 g Average: 0.05525 g/25 ml |
| Calculation of content of sulphated ash | 0.05525 g/25.05 g = 0.0022055g/g = 2.2055 mg/g 0.22 % |

EXAMPLE 85. LOSS ON DRYING

Based on this Phytochem® established appropriate methods for the determination of loss on drying.

1. Method and Parameter for Test of Chitosan HCl, Chitosan and Chitosan HAc
Sample Preparation
Pretreatment of container: The substance is placed in a suitable weighing bottle, previously dried under the conditions used afterwords
Filling: the material is filled not higher than 5 millimeter
Transport: The weighing bottle is closed with a suitable cover
PC-method: A "under higher vacuum"
modified Pharmacopoeia-method 2.2.32 (EP) "in vacuum in a desiccator"
Apparatus: desiccator
Drying time: to constant weight
Drying temperature: 25° C.±2° C.
Vacuum: permanent 4-8 mbar with specific pumps
Drying reagent: Diphosporuspentoxide (freshly)

2. Estimation of the Loss on Drying of Chitosan in Chitosan-Valeric Acid-Hydro-Colloid (Special Method)
The content of Chitosan in Chitosan-Valeric acid-Hydro-Colloid is estimated with a gravimetric measurement.
Apparatus: Speed circulating vacuum concentrator
Method: Estimation of the loss on drying (special method)

Conditions of Measurement
Pressure: 5 mbar
Temperature: 60° C.
Time: 1 week
End point: Constant mass
Appearance: Glassy mass
Measurement: Test solution 4 ml Chitosan-Valeric acid-Hydro-Colloid
Repetition: 10 times
Result Odor: No typical odor from valeric acid
Weighing

| 1  | 40.20 mg |
|----|----------|
| 2  | 39.80 mg |
| 3  | 40.20 mg |
| 4  | 39.90 mg |
| 5  | 40.10 mg |
| 6  | 40.10 mg |
| 7  | 39.90 mg |
| 8  | 39.60 mg |
| 9  | 40.20 mg |
| 10 | 40.40 mg |

Average 40.04 mg
Standard deviation 0.236643191
Relative standard deviation 0.591016961
Variance 0.056
Results: The weighing of the dried substance shows good similarity. Based on this measurements the content of Chitosan in Chitosan-Valeric acid-Hydro-Colloid is 1%.
Comparison of the Results

|  | Chitsoan solid | Chitsoan HCI solid | Chitsoan HAc solid | Chitosan-Valerie acid-Hydro-Colloid |
|---|---|---|---|---|
| Loss on drying | 7.2% | 7.9% | 20.3% | — |
| Residue from drying | — | — | — | 1% |
| Target EP | — | <10% | — | — |

The active principle should be a Hydro Colloid gel. The measured data confirm the structure of compound.

EXAMPLE 86. ESTIMATION OF THE OSMOLARITY

The estimation of the Osmolarity can be done was an indirect measurement of the decrease of the melting point of a solution.
Apparatus: Halbmicro Osmometer Knauer
Conditions of measurement: External cooling system
Range: 0-1600 mOsmol
Method: Freezing
Test Procedure
Calibration with Standard solution 400 mOsmol/Kg: 12,687 g NaCl in 1 l Wasser at 20° C.
Repetition: 2 times
Vessel: Specific glass vial
Sample: Chitosan-Valeric acid-Hydro-Colloid
Test solution: 1 without dilution
2 Dilution of 1:5
Quantity 150 µl each
Calibration

| Sample | Spezification | Setpoint | Measured value |
|---|---|---|---|
| Calibration 1 | Bidest. water | 0 mOsmol | 0 mOsmol |
| Calibration 2 | 400 m Osmol/kg | 400 mOsmol | 400 mOsmol |

Measurement

| Number | Sample | Measured value |
|---|---|---|
| 1a | Chitosan-Valeric acid-Hydro-Colloid | 100 mOsmol |
| 1b | Chitosan-Valeric acid-Hydro-Colloid | 110 mOsmol |
| 2a | Chitosan-Valeric acid-Hydro-Colloid | 1:5 20 mOsmol |
| 2b | Chitosan-Valeric acid-Hydro-Colloid | 1:5 20 mOsmol |

Results: The measurement of the Osmorarity of Chitosan-Valeric acid-Hydro-Colloid show a relatively low content. The measured content of osmolar reacting components can only be so low, if there is no solution or suspension of chitosans and valeric acid. The high viscous gelling compound can only be a Hydro-Colloid.
Result: The measured data above confirms the identity of the proposed substance.

The invention claimed is:
1. A method comprising the step of:
   (i) dissolving chitosan in an aqueous solution of an acid,
   (ii) increasing the pH value of the solution obtained in step (i) until the chitosan is precipitated, thereby creating a suspension,
   (iii) centrifuging the suspension of step (ii) and recovering the precipitated chitosan, and
   (iv) incubating the precipitated chitosan in an aqueous solution of an organic carboxylic acid or a salt thereof, wherein the organic carboxylic is selected form the group consisting of valeric acid, para-aminobenzoic acid, glucuronic acid or a salt of any of said acids, in particular a valeric acid chloride.
2. The method of claim 1, wherein the chitosan used for step (i) has a degree of deacetylation of about 62% to about 98%, and/or wherein the chitosan has a molecular weight or average molecular weight of about 80 kDa to about 700 kDa.
3. The method according to claim 1, wherein step (iv) additionally comprises the addition of a mineral acid or an organic acid.
4. A modified chitosan obtainable by the method of claim 1.
5. A hydro colloid comprising:
   (i) 0.1% to 5% (w/v) chitosan and 0.001% to 5% (w/v) valeric acid, or a salt thereof, or
   (ii) 0.1% to 5% (w/w) chitosan and 0.001% to 5% (w/w) glucuronic acid or p-aminobenzoic acid or a salt thereof.
6. A compound of formula [X]n, in which n represents an integer of about 1 to about 5000, in particular an integer of about 300 to about 4000, and X has the following formula (1):

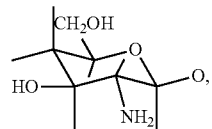

wherein about 2% to about 38%, of the X residues constituting said compound are modified by acetylation and wherein all or part of the X residues constituting said compound are modified by the organic carboxylic acid selected from the group consisting of valeric acid, para-aminobenzoic acid, glucuronic acid or a salt of any of said acids.

7. A composition comprising the modified chitosan according to claim 4, in particular wherein the composition is a pharmaceutical composition and comprises a pharmaceutical acceptable diluent, excipient and/or carrier.

8. The composition according to claim 7, wherein the composition comprises additionally antigenic material from microorganisms and/or enzymes, in particular antigenic material of keratinophilic fungi and/or keratinophilic yeasts, preservatives and/or antibiotics.

9. The composition of claim 8, wherein the antigenic material comprises antigens of one or more of *Candida*, in particular *Candida albicans*, *Trichophyton*, in particular *Trichophyton verrucosum*, *Trichophyton mentagrophytes*, *Trichophyton equinum*, *Trichophyton sarkisovii*, *Trichophyton rubrum* and/or *Trichophyton mentagrophytes*, *Microsporum*, in particular *Microsporum canis* such as *Microsporum canis* var. *obesum* and/or *Microsporum canis* var. *distortum*, and/or *Microsporum gypseum*, and/or Chrisporium, in particular Chrisporium *tropicum*.

10. The composition of claim 9, wherein the antigenic material is from one or more of the following strains: *Trichophyton mentagrophytes* DSM-7279, *Trichophyton verrucosum* DSM-28406, *Trichophyton rubrum* DSM-9469, *Trichophyton rubrum* DSM-9470, *Trichophyton rubrum* DSM-9471, *Trichophyton rubrum* DSM-9472, *Candida albicans* DSM-9456, *Candida albicans* DSM-9457, *Candida albicans* DSM-9458, *Candida albicans* DSM-9459, Chrisporium *tropicum* DSM-28405, and *Microsporum canis* DSM-32271.

11. The composition according to claim 7, wherein the modified chitosan; is present in a concentration of about 0.1 to about 2.0% (w/v), in particular of about 0.1 to about 1.4% (w/v), more particularly of about 0.1% to about 0.3% (w/v).

12. A method of vaccinating a human or veterinary subject comprising administering the modified chitosan according to claim 4 to said subject.

13. The method of claim 12, wherein vaccinating treats or prevents mastitis, preferably latent mastitis and/or acute mastitis, endometritis, preferably chronic, acute and/or purulent-catarrhal endometritis, hoof- and claw diseases, lameness, lesions in the interdigital space, digital dermatitis, interdigital dermatitis, interdigital phlegmon, trichophytosis, microsporosis, mycosis of skin, allergies, as well as diseases complicated by allergies, in particular allergic obstructive pulmonary disease, allergic skin diseases, allergic ear erythema, allergic rhinitis, allergic conjunctivitis, acute allergic contact dermatitis, chronic allergic contact eczema or atopic eczema, obstructive pulmonary disease, in particular chronic obstructive pulmonary disease, skin diseases, in particular dermatitis, ear erythema, rhinitis, conjunctivitis, dermatophytosis or warts, in particular Common warts, in a subject and for modulating the immune response in a subject and/or for enhancing reproduction efficiency, preferably reproduction efficiency in animal breeding.

14. The method of claim 2, wherein the chitosan has a degree of deacetylation of about 80% to about 95%.

15. The method according to claim 1, wherein the aqueous solution of an acid of step (i) is an aqueous solution of an acetic acid, and/or wherein increasing the pH value is increasing to a pH value of about 8.0 to about 8.5.

16. The method according to claim 3, wherein the mineral acid is HCl or $H_2SO_4$, or the organic acid is lactic acid, para-aminobenzoic acid or glucuronic acid.

17. The hydro colloid of claim 5, wherein the valeric acid, or a salt thereof, is a chloride of valeric acid.

18. The compound of claim 6, wherein about 5% to about 20% of the X residues constituting said compound are modified by acetylation.

19. The compound of claim 6, wherein the organic carboxylic acid is a valeric acid chloride.

20. The compound according to claim 6, wherein the compound is present in a concentration of about 0.1% to about 2.0% (w/v), in particular of about 0.1% to about 1.4% (w/v), more particularly of about 0.1% to about 0.3% (w/v).

* * * * *